(12) United States Patent
Civan et al.

(10) Patent No.: US 6,528,516 B1
(45) Date of Patent: Mar. 4, 2003

(54) METHODS FOR REDUCING INTRAOCULAR PRESSURE USING A3 ADENOSINE RECEPTOR ANTAGONISTS

(75) Inventors: Mortimer M. Civan, Wynnewood, PA (US); Richard A. Stone, Havertown, PA (US); Claire H. Mitchell, Philadelphia, PA (US); Kenneth A. Jacobson, Silver Springs, MD (US)

(73) Assignee: Trustees of the University of Pennsylvania, The Center for Technology Transfer, Philadelphia, PA (US)

( * ) Notice: Subject to any disclaimer, the term of this patent is extended or adjusted under 35 U.S.C. 154(b) by 0 days.

(21) Appl. No.: 09/743,744

(22) PCT Filed: Jul. 15, 1999

(86) PCT No.: PCT/US99/16211

§ 371 (c)(1),
(2), (4) Date: May 4, 2001

(87) PCT Pub. No.: WO00/03741

PCT Pub. Date: Jan. 27, 2000

Related U.S. Application Data

(60) Provisional application No. 60/122,965, filed on Mar. 3, 1999, and provisional application No. 60/093,097, filed on Jul. 16, 1998.

(51) Int. Cl.$^7$ ............................................. A61K 31/435
(52) U.S. Cl. ........................................ 514/277; 514/913
(58) Field of Search ................................ 514/277, 913

(56) References Cited

U.S. PATENT DOCUMENTS

| | | | | |
|---|---|---|---|---|
| 4,937,242 A | * | 6/1990 | Matsui et al. | ............. 514/235.8 |
| 5,952,330 A | * | 9/1999 | Rupniak et al. | ......... 514/234.5 |

FOREIGN PATENT DOCUMENTS

WO    WO97/27177    7/1997

OTHER PUBLICATIONS

Alunlakshana et al., "Some Quantitative Uses of Drug Antagonists," *Brit. J. Pharmacol.* 14:48–59 (1959).

Ben–Baruch et al., "Cooperativity Pattern in the Interaction of the Antiestrogen Drug Clomiphene with the Muscarinic Receptors," *Mol. Pharmacol.*, 21:287–293 (1981).

Bodor et al., "Improved Delivery through Biological Membranes," *J. Med. Chem.* 26:528–534 (1983).

Brandes et al., "New Evidence that the Antiestrogen Binding Site may be a Novel Growth–Promoting Histamine Receptor (?H$_3$) which Mediates the Antiestrogen and Antiproliferative Effects of Tamoxefin," *Biochem. Biophys. Res. Commun.*, 134:601–608 (1986).

Cabantchik et al., "Chemical Probes for Anion Transporters of Mammalian Cell Membranes," *Am. J. Physiol.* 262:C803–C827 (1992).

Carre et al., "Adenosine Stimulates Cl$^-$ Channels of Non–pigmented Ciliary Epithelial Cells," *Am. J. Physiol. (Cell Physiol.* 42) 273:C1354–C1361 (1997).

Carre, et al., "cGMP Modulates Transport across the Ciliary Epithelium," *J. Membr. Biol.* 146:293–305 (1995).

Cheng et al., "Relationship Between the Inhibition Constant (K$_1$) and the Concentration of Inhibitor which Causes 50 per cent Inhibition (I$_{50}$) of an Enzymatic Reaction," *Biochem. Pharmacol.* 22:3099–3108 (1973).

Civan et al., "Regulatory Volume Decrease by Cultured Non–pigmented Ciliary Epithelial Cells," *Exp. Eye Res.* 54:181–191 (1992).

Civan et al., "Pathways Signaling the Regulatory Volume Decrease of Cultured Nonpigmented Ciliary Epithelial Cells," *Invest. Ophthalmol. Vis. Sci.*, 35:2876–2886 (1994).

Civan, "Transport Components of Net Secretion of the Aqueous Humor and Their Integrated Regulation," *Current Topics in Membranes* 45: 1–24 (1998).

Civan, "Transport by the Ciliary Epithelium of the Eye," *News Physiol. Sci.* 12: 158–162 (1997).

Coca–Prados, et al., "PKC–sensitive Cl$^-$ Channels Associated with Ciliary Epithelial Homologue of pI$_{Cln}$," *Am. J. Physiol.* 268: C572–C579 (1995).

Cole, "Secretion of the Aqueous Humour," *Exp. Eye Res.* 25 (Suppl.) 161–176 (1977).

Crosson et al., "Characterization of Ocular Hypertension Induced by Adenosine Agonists," *Invest. Ophthalmol. Vis. Sci.* 37: 1833–1839 (1996).

Crosson, "Adenosine Receptor Activation Modulates Intraocular Pressure in Rabbits," *J. Pharmacol. Exp. Ther.* 273:320–326 (1995).

Farahbakhsh et al., "Synergistic Increase in Ca$^{2+}$ Produced by A$_1$ Adenosine and Muscarinic Receptor Activation via a Pertussis–Toxin–Sensitive Pathway in Epithelial Cells of the Rabbit Ciliary Body," *Exp. Eye Res.* 64:173–179 (1997).

Fredholm et al., "Nomenclature and Classification of Purinoceptors," *Pharmacol. Rev.*, 46:143–156 (1994).

Fredholm et al., "Towards a Revised Nomenclature for P1 and P2 Receptors," *Trends Pharmacol. Sci.* 18:79–82 (1997).

Gallo–Rodriguez et al., "Structure–Activity Relationships of N$^6$–Benzyladenosine–5'–uronamides as A$_3$–Selective Adenosine Agonists," *J. Med. Chem.*, 37:636–646 (1994).

Green et al., "An Electrophysiologic Study of Rabbit Ciliary Epithlium," *Invest. Ophthalmol. Vis. Sci.* 26:371–381 (1985).

(List continued on next page.)

*Primary Examiner*—Zohreh Fay

(57) ABSTRACT

This invention relates to a method of decreasing intraocular pressure by administrating an A3 subtype adenosine receptor antagonist, a calmodulin antagonist or an antiestrogen such as tamoxifen.

17 Claims, 18 Drawing Sheets

OTHER PUBLICATIONS

Grynkiewicz et al., "A New Generation of $Ca^{2+}$ Indicators with Greatly Improved Fluorescence Properties," *J. Biol. Chem.* 260:3440–3450 (1985).

Hardy et al., "Novel Plasma Membrane Action of Estrogen and Antiestrogens Revealed by their Regulation of a Large Conductance Chloride Channel," *FASEB J.* 8: 760–765 (1994).

Hoffman et al., *Interaction of Cell Volume and Cell Function*, Lang, et al., eds., Springer, Heidelberg, Germany, pp. 188–248, (ACEP Series 14), (1993).

Hutchison et al., "CGS 21680C, an $A_2$ Selective Adenosine Receptor Agonist with Preferential Hypotensive Activity," *J. Pharmacol. Exp. Ther.* 251:47–55 (1989).

Jacob "Two Outward K+ Currents in Bovine Pigmented Ciliary Epithelial Cells: $1_{k(Ca)}$ and $1_{K(Ca)}$," *Am. J. Physiol.* 261:C1055–C1061 (1991).

Jacobson, "Adenosine $A_3$ Receptors: Novel Ligands and Paradoxical Effects," *Trends Pharmacol. Sci.* 19:184–191 (1998).

Jacobson et al., "A Role for Central $A_3$–Adenosine Receptors Mediation of Behavioral Depressant Effects," *FEBS Lett.* 336:57–60 (1993).

Jacobson et al., "Pharmacological Characterization of Novel $A_3$ Adenosine Receptor–Selective Antagonistics," *Neuropharmacol.* 36:1157–1165 (1997).

Jacobson, et al., "$A_3$–Adenosine Receptors: Design of Selective Ligands and Therapeutic Prospects," *Drugs of Future* 20(7):689–699 (1995).

Jarvis et al., "[$^3$H] CGS 21680, A Selective $A_2$ Adenosine Receptor Agonist Directly Labels $A_2$ Receptors in Rat Brain," *J. Pharmacol. Exp. Ther.*, 251:888–893 (1989).

Jiang et al., "Structure–Activity Relationships of 4–(Phenylethynyl)–6–phenyl–1,4–dihydropyridines as Highly Selective $A_3$ Adenosine Receptor Antagonists," *J. Med. Chem.* 40:2596–2608 (1997).

Jiang et al., "6–phenyl–1,4–dihydropyridine Derivatives as Potent and Selective $A_3$ Adenosine Receptor Antagonists," *J. Med. Chem.* 39:4667–4675 (1996).

Klinge et al., "What Differentiates Antiestrogen–Liganded vs Estradiol–Liganded Estrogen Receptor Action?," *Oncology Research*, 4;145–150 (1992).

Klotz et al., "Comparative Pharmacology of Human Adenosine Receptor Subtypes—Characterization of Stably Transfected Receptors in CHO Cells," *Naunyn–Schmiedeberg's Arch. Pharmacol.* 357:1–9 (1998).

Kohno et al., "Activation of $A_3$ Adenosine Receptors on Human Eosinophils Elevates Intracellular Calcium," *Blood,* 88:3569–3574 (1996).

Kvanta et al., "Localization of Adenosine Receptor Messenger RNAs in the Rat Eye," *Exp. Eye Res.* 65:595–602 (1997).

Lam, "Tamoxifen is a Calmodulin Antagonist in the Activation of cAMP Phosphodiesterase," *Biochem. Biophys. Res. Commun.* 118:27–32 (1984).

Lee et al., "Aquaporin Water Channels in Eye and Other Tissues," *Current Topics in Membranes* 45:105–134 (1998).

Li et al., "Synthesis, CoMFA Analysis, and Receptor Docking of 3,5–Diacyl–2–4–Dialkylpyridine Derivatives as Selective $A_3$ Adenosine Receptor Antagonists," *J. Med Chem.* 42(4):706–721 (1999).

Li et al., "Structure–Activity Relationships and Molecular Modeling of 3,5–Diacyl–2,4–dialkylpyridine Derivatives as Selective $A_3$ Adenosine Receptor Antogonists," *J. Med. Chem.* 41:3186–3201 (1998).

Meinild, et al. "The Human $Na^+$–glucose Contransporter is a Molecular Water Pump," *J. Physiol.* 508.1: 15–21 (1998).

Mitchell, et al., "$A_3$ Adenosine Receptors Regulate $Cl^-$ Channels of Nonpigmented Ciliary Epithelial Cells," *Am. J. Physiol.* 276 (Cell Physiol. 45):C659–C666 (1999).

Mitchell et al., "Tamoxifen Accelerates the ATP–Activated Regulatory Volume Decrease of Bovine Pigmented Ciliary Epithelial Cells," *Invest. Ophthalmol. Vis. Sci.*38 (Suppl.) S1042 (1997).

Mitchell, et al., "A Release Mechanism for Stored ATP in Oculary Ciliary Epithelial Cells," *Proc. Natl. Acad. Sci U.S.A.* 95: 7174–7178 (1998).

Negalescu et al., "[4] Intracellular Ion Activities and Membrane Transport in Parietal Cells Measured with Fluorescent Dyes," *Meth. Enzymol.* 192:38–81 (1990).

Nilius, et al., "Volume–activated $Cl^-$ Currents in Different Mammalian Non–excitable Cell Types," *Pflügers Archiv.* 428: 364–371 (1994).

Olah et al. "$^{125}$1–4–Aminobenzyl–5'–N–methylcarboxamidoadenosine, a High Affinity Radioligand for the Rat $A_3$ Adenosine Receptor," *Mol. Pharmacol.* 45:978–982 (1994).

O'Brian et al., "Inhibition of Protein Kinase C by Tamoxifen," *Cancer Res.* 45:2462–2465 (1985).

Salomon et al., "A Highly Sensitive Adenylate Cyclase Assay," *Anal Biochem.* 58:541–548 (1974).

Salvatore et al., "Molecular Cloning and Characterization of the Human $A_3$ Adenosine Receptor," *Proc. Natl. Acad. Sci. U.S.A.* 90:10365–10369, (1993).

Schwabe et al., "Characterization of Adenosine Receptors in Rat Brain by (-)[$^3$H]$N^6$–Phenylisopropyladenosine," *Naunyn–Schmiedeberg's Arch. Pharmacol.* 313:179–187 (1980).

Shahidullah et al., "Mobilisation of Intracellular Calcium by $P2Y_2$ Receptors in Cultured, Non–Transformed Bovine Ciliary Epithelial Cells," *Curr. Eye Res.* 16:1006–1016 (1997).

Stambaugh et al., "A Novel Cardioprotective Function of Adenosine–$A_1$ and $A_3$ Receptors During Prolonged Simulated Ischemia," *Am. J. Physiol.* 273 (*Heart Circ. Physiol* 42):H501–H505 (1997).

Stamer et al., "Localization of Aquaporin CHIP in the Human Eye: Implications in the Pathogenesis of Glaucoma and Other Disorders of Ocular Fluid Balance," *Invest. Ophthalmol. Vis. Sci.* 35: 3867–3872 (1994).

Stuart et al., "High–Dose Tamoxifen as an Enhancer of Etoposide Cytotoxicity. Clinical Effects and In Vitro Assessment in p–Glycoprotein Expressing Cell Lines," *Br. J. Cancer,* 66, 833–839 (1992).

Tian, et al., "Effects of Adenosine Agonists on Intraocular Pressure Aqueous Humor Dynamics in Cynomolgus Monkeys," *Exp. Eye Res.* 64:979–989 (1997).

Valverde et al., "Differential Effects of Tamoxefin and $I^-$ on Three Distinguishable Chloride Currents Activated in T84 Intestinal Cells," *Pflügers Archiv.* 425:552–554 (1993).

Wangemann et al., "$Cl^-$Channel Blockers in the Thick Ascending Limb of the Loop of Henle. Structure Activity Relationship." *Pflügers Archiv.* 407(Suppl.2):S128–S141 (1986).

Wax et al., "Purinergic Receptors in Ocular Ciliary Epithelial Cells," *Exp. Eye Res.* 57:89–95 (1993).

Wax et al., "Immunoprecipitation of $A_1$ Adenosine Receptors–GTP–Binding Protein Complexes in Ciliary Epithelial Cells," *Invest. Ophthalmol. Vis. Sci.,* 35:3057–3063 (1994).

Wu et al., "P–glycoprotein Regulates a Volume–Activated Chloride Current in Bovine Non–pigmented Ciliary Epithelial Cells," *J. Physiol.* 491.3:743–755 (1996).

Wu, et al., "Brain–Specified Chemical Delivery System of β–Lactam Antibiotics. In Vitro and In Vivo Studies of Some Dihydropyridine and Dihydroisoquinoline Derivatives of Benzylpenicillin in Rats," *J. Med. Chem.* 32:1782–1788 (1989).

Yantorno et al., "Volume Regulation of Cultured, Transformed, Non–Pigmented Epithelial Cells from Human Ciliary Body," *Exp. Eye Res.* 49:423–437 (1989).

Zhang, et al., "Tomoxifen Blocks Chloride Channels. A Possible Mechanism for Cataract Information," *J. Clin. Invest.* 94(4):1690–1697 (1997).

Zhou et al., "Molecular Cloning and Characterization of an Adenosine Receptor: The A3 Adenosine Receptor," *Proc. Natl. Acad. Sci. U.S.A.* 89:7432–7436 (1992).

* cited by examiner

METHODS FOR REDUCING INTRAOCULAR PRESSURE USING A3 ADENOSINE RECEPTOR ANTAGONISTS

This application is a 371 of PCT/US99/16211 filed on Jul. 15, 1999, which claims the benefit of provisional applications Nos. 60/093,097 filed Jul. 16, 1998 and 60/122,965 filed Mar. 3, 1999.

FIELD OF THE INVENTION

The present invention relates to the use of A3 subtype adenosine receptor antagonists, calmodulin antagonists and antiestrogens for reduction of intraocular pressure.

BACKGROUND OF THE INVENTION

The aqueous humor of the eye is formed by the ciliary epithelium, which comprises two cell layers: the outer pigmented epithelial (PE) cells facing the stroma and the inner nonpigmented epithelial (NPE) cells in contact with the aqueous humor. Secretion is generally thought to reflect a primary transfer of solute, largely NaCl, from the stroma to the aqueous humour, providing an osmotic driving force for the secondary osmotic transfer of water down its chemical gradient (Cole,. *Exp. Eye Res.* 25 (Suppl.), 161–176, 1977), although a more direct coupling between water and solute may also proceed across epithelia (Meinild et al. *J. Physiol.* 508: 15–21, 1998). One major factor governing the rate of secretion is the rate of chloride ion ($Cl^-$) release from the NPE cells into the aqueous humor (Civan, *News Physiol. Sci.* 12:158–162, 1997). The activity of $C^-$ channels is likely to be a rate-limiting factor in aqueous humour secretion, given the low baseline level of channel activity and the predominance of the chloride anion in the fluid transferred (Coca-Prados et al., *Am. J. Physiol.* 268: C572–C579, 1995). The secretion of aqueous humor into the eye is believed to result as a consequence of two opposing physiological processes: fluid secretion into the eye by the NPE cells and fluid reabsorption (secretion out of the eye) by the PE cells. Thus, both release of $C^-$ by the nonpigmented ciliary epithelial (NPE) cells into the adjacent aqueous humour would enhance secretion, and $C^-$ release by the pigmented ciliary epithelial (PE) cells into the neighboring stroma would reduce net secretion (Civan, *Current Topics in Membranes* 45: 1–24, 1998).

Recently, adenosine has been found to activate NPE $Cl^-$ channels which subserve this release (Carre et al., *Am. J. Physiol.* (Cell Physiol. 42) 273:C1354C–C1361, 1997). Purines, a class of chemical compounds which includes adenosine, ATP and related compounds, may regulate aqueous humour secretion, in part through modifying $Cl^-$-channel activity. Both NPE and PE cells have been reported to release ATP to the extracellular surface, where ATP can be metabolized to adenosine by ecto-enzymes (Mitchell et al. *Proc. Natl. Acad. Sci U.S.A.* 95: 7174–7178, 1998), and both cell types possess adenosine receptors (Wax et al., *Exp. Eye Res.* 57:89–95, 1993; Wax et al, *Invest. Ophthalmol. Vis. Sci.*, 35:3057–3063, 1994; Kvanta et al., *Exp. Eye Res.* 65:595–602, 1997) and ATP receptors (Wax et al., supra., 1993; Shahidullah et al., *Curr. Eye Res.* 16:1006–1016, 1997). Furthermore, in vitro studies of rabbits have associated $A_2$-adenosine receptors with increased secretion and elevated intraocular pressure (Crosson et al., *Invest. Ophthalmol. Vis. Sci.* 37:1833–1839, 1996) and $A_1$-adenosine receptors with the converse (Crosson, *J. Pharmacol. Exp. Ther.* 273:320–326, 1995). Qualitatively similar associations with intraocular pressure, but not with secretion, have been observed in cynomologus monkeys (Tain et al., *Exp. Eye Res.*, 64: 979–989, 1997). A particular role for $Cl^-$ channels has been suggested by the observations that adenosine agonists stimulate $Cl^-$ channels of immortalized human and freshly-dissected bovine NPE cells and of aqueous-oriented $Cl^-$ channels of the intact rabbit iris-ciliary body (Carré et al., supra., 19971. Adenosine triggered isotonic shrinkage of cultured human cells from the HCE cell line. The contribution of $Cl^-$ channels to this shrinkage was identified by performing the experiments in the presence of the cation ionophore gramicidin. In addition, adenosine produced a $Cl^-$ dependent increase in short-circuit current across rabbit iris-ciliary body while the non-metabolizable adenosine analogue 2-Cl-adenosine was shown to activate $Cl^-$ currents in HCE cells using the whole cell patch-clamp technique. Although this study clearly established that adenosine could activate $Cl^-$ channels on NPE cells, the concentrations of agonist used were capable of stimulating all four known adenosine receptor sub-types: $A_1$, $A_{2A}$, $A_{2B}$ and $A_3$ (Fredholm et al., *Pharmacol Rev.*, 46:143–156, 1994; Fredholm et al., *Trends Pharmacol, Sci.*, 18:79–82, 1997; Klotz et al., *Naunyn Schmiedebergs Arch. Pharmacol.*, 357:1–9., 1998). Ciliary epithelial cells are known to possess $A_1$ $A_{2A}$ and $A_{2B}$ adenosine receptors (Kohno et al., *Blood*, 88:3569–3574, 1996, Stambaugh et al., *Am. J. Physiol.* 273 (Heart Circ. Physiol. 42):H501–H505, 1997; Wax et al., supra., 1994). Although stimulation of these receptors can be associated with specific changes in the levels of second messengers cAMP (Crosson, supra.; Stambaugh et al., supra.; Wax et al., supra., 1994) and $Ca^{2+}$ (Farahbakhsh et al., *Exp. Eye Res.*, 64:173–179, 1997), the effect of these receptors upon $Cl^-$ channels of NPE cells was unknown.

Alternatively, the intraocular pressure could be reduced by stimulating reabsorption of aqueous humor. In principle, this could be achieved by activating chloride channels on the basolateral surface of the pigmented cell layer. This would release chloride back into the stroma. One way to accomplish this with the PE cells has been identified using the antiestrogen tamoxifen. Tamoxifen is known to exert multiple actions on biological cells. However, recently, Mitchell et al. (*Invest Ophthalmol. Vis. Sci.* 38(Suppl.):S1042, 1997) have noted that the only known action of tamoxifen which could account for the phenomenon is its antiestrogenic activity, probably on the plasma membrane.

Glaucoma is a disorder characterized by increased intraocular pressure that may cause impaired vision, ranging from slight loss to absolute blindness. The increased intraocular pressure is related to an imbalance between production and outflow of the aqueous humor. Current drugs prescribed for glaucoma, in the form of eyedrops, include pilocarpine, timolol, betaxolol, levobunolol, metipranolol, epinephrine, dipivefrin, latanoprost, carbachol, and potent cholinesterase inhibitors such as echothiophate and carbonic anhydrase inhibitors such as dorzolamidet. Many of these effective approaches to medical therapy of glaucoma involve a reduction in the rate of flow into the eye. However, none of these drugs are satisfactory, in part due to side effects.

Because of side effects of available agents and inconvenient dosing schedule, there is an ongoing need for compounds capable of reducing intraocular pressure for the treatment of glaucoma with improved efficacy, prolonged action and reduced side effects. The present invention addresses this need.

SUMMARY OF THE INVENTION

One embodiment of the present invention is a method for reducing intraocular pressure in an individual, comprising the step of administering to the individual an effective intraocular pressure-reducing amount of a pharmaceutical composition comprising an $A_3$ subtype adenosine receptor antagonist. In one aspect of this preferred embodiment, the $A_3$ receptor antagonist is a dihydropyridine, pyridine, pyridinium salt or triazoloquinazoline. Preferably, the $A_3$ subtype receptor antagonist is selected from the group consisting of MRS-1097, MRS-1191, MRS-1220 and MRS-1523. Advantageously, the pharmaceutical composition is administered topically, systemically or orally. Preferably, the pharmaceutical composition is an ointment, gel or eye drops.

Another embodiment of the present invention is a method for reducing intraocular pressure in an individual, comprising the stop of administering to the individual an effective intraocular pressure-reducing amount of a pharmaceutical composition comprising an antiestrogen. Preferably, the antiestrogen is tamoxifen. Advantageously, the pharmaceutical composition is administered topically, systemically or orally. Preferably, the pharmaceutical composition is ointment, gel or eye drops.

The present invention also provides a method for reducing intraocular pressure in an individual, comprising the step of administering to the individual an effective intraocular pressure-reducing amount of a pharmaceutical composition comprising a calmodulin antagonist. Preferably, the calmodulin antagonist is trifluoperazine. Advantageously, the pharmaceutical composition is administered topically, systemically or orally. Preferably, the pharmaceutical composition is ointment, gel or eye drops.

Another embodiment of the present invention is an $A_3$ subtype adenosine receptor antagonist for use in reduction of intraocular pressure. Preferably, the $A_3$ subtype adenosine receptor antagonist is MRS-1097, MRS-1191 or MRS-1523.

The present invention also provides the use of an antiestrogen in the preparation of a medicament for the reduction of intraocular pressure. Preferably, the antiestrogen is tamoxifen.

The present invention also provides a calmodulin antagonist for use in reduction of intraocular pressure. Preferably, the calmodulin antagonist is trifluoperazine.

BRIEF DESCRIPTION OF THE FIGURES

FIGS. 2–7 relate to the effects of $A_3$ receptors on NPE cells, while FIGS. 8–17 relate primarily to the actions of ATP on PE cells.

In FIGS. 2–5, solid trajectories are least-square fits with monoexponentials, whereas data sets displaying no significant shrinkage are connected by dotted lines.

FIG. 2A:—least-squares fits yielded the following estimated values for data obtained in parallel at concentrations of 30 nM –1 υM IB-MECA (n=4 experiments): 30 nM [steady-state cell volume (V∞)=98.5±0.1%, τ=3.5±1.5 min), and 1 $\mu$M (V∞=95.9±0.3%, τ=2.4±0.7 min). Control and 3 sets of experimental results were significantly different (P<0.01, F-test).

FIG. 2B data obtained over concentration range of 1–10 $\mu$M IB-MECA (n=4): 1 $\mu$M (V∞=97.5±0.1%, τ=7.2±1.0 min), 3 $\mu$M (V∞=96.7±0.3%, τ=10.0±2.3 min), and 10 $\mu$M (V∞=97.9±0.2%, τ=3.2±1.1 min). obtained at 1 $\mu$M and 3 $\mu$M did not significantly deviate from the fit obtained with 10 $\mu$M IB-MECA.

FIG. 2C shows a Lineweaver-Burk plot generated from nonlinear least-square fits of FIGS. 1A and 1B. Change in volume was calculated as (V0–V∞). Variation with passage number was noted for τ and (V0–V∞). For this reason, both experimental sets (FIGS. 1A and 1B) included measurements with one concentration (1 $\mu$M) in common. Ratio (in V0–V∞) obtained at 1 $\mu$M in B to A was used as a scaling factor to accommodate results obtained in B with 3 and 10 $\mu$M. Using this approach, linear least-squares analysis ($r^2$=0.95) led to an estimated value for the apparent $K_d$ of 55±10 nM.

FIG. 2D shows isotonic cell shrinkage stimulated by 100 nM Cl-IB-MECA. Fits for Cl-IB-MECA (V∞=97.9±0.2%, τ=2.5±1.3 min) and IB-MECA (V∞=96.8±0.4%, τ=6.3±2.2 min) are not significantly different (P>0.05).

FIG. 3A shows that the $A_3$-selective antagonist MRS-1097 (300 nM) prevented shrinkage triggered by IB-MECA (P<0.01, F-distribution).

FIG. 3B shows that the $A_3$-selective antagonist MRS-1191 (100 nM) prevented characteristic shrinkage triggered by IB-MECA (n=4, P<0.01 by F-distribution). MRS did not affect cell volume in the absence of IB-MECA, confirming the specificity of the interaction (n=4).

In FIG. 5A, the $A_3$-selective agonist IB-MECA produced prompt shrinkage at 100 nM (n=4, V∞=95.6±0.2%, τ=4.5±0.6 min, P<0.01 by F-distribution). In contrast, the $A_1$-selective agonist $N^6$-cyclopentyladenosine (CPA) had little effect at 100 nM, and none at all at 3 $\mu$M (n=4).

In FIG. 5B, at 100 nM, the $A_2$-selective agonist CGS-21680 exerted no effect, but the $A_3$-selective agonist IB-MECA again produced shrinkage (n=4, P<0.01 by F-distribution).

In FIG. 5C, at high concentration (3 $\mu$M), the $A_2$-selective agonist CGS-21680 also triggered isoosmotic shrinkage. However, preincubation of the cells with the selective $A_3$ receptor antagonist MRS-1191 (100 nM) abolished this effect (n=4, P<0.01, F-distribution).

FIG. 6 shows the effects of IB-MECA on the level of free intracellular calcium of NPE cells. Concentration of intracellular $Ca^{2+}$ increased steadily after application of 100 nM IB-MECA and returned to baseline levels once IB-MECA was removed. Data were obtained at a sampling rate of 1 Hz and smoothed by 21 points. The box indicates the duration of the IB-MECA application.

FIG. 7 shows the effect of IB-MECA on short-circuit current ($I_{SC}$) across intact rabbit ciliary epithelium. As an initial step in data analysis, 20-min period of baseline current just before addition of any agent was fit by linear least-squares analysis. The line generated by that analysis was extrapolated to a point 45 min beyond introduction of that agent. Each current response was subtracted from its respective extrapolated baseline to yield a common initial baseline approximating constant zero current. All recordings were placed in register relative to time of agent introduction (time 0). Records of control (solvent), IB-MECA with solvent, and IB-MECA corrected for solvent were separately averaged. IB-MECA was always added in the presence of 5 mM $Ba^{2+}$ to isolate contribution of $Cl^-$ to the response.

FIGS. 2–7 show that $A_3$-selective adenosine receptors increase chloride channel activity of NPE cells, and that blocking of these receptors reduces chloride channel activity and secretion by the NPE cells into the aqueous humor.

FIGS. 8–17 provide data to support an alternative approach to reducing net aqueous humor secretion and intraocular pressure by enhancing reabsorption by the PE cells.

FIG. 8A shows that in ~15% of the preparations, a concentration-dependent shrinkage was observed with ATP alone (N=4, P<0.01). The values generated by the fits were: $v_\infty$=94.3±0.3% and $\tau$=2.8±0.7 min (10 $\mu$M ATP), and $v_\infty$=94.3±0.3%, $\tau$=2.8±0.7 min (100 $\mu$M ATP).

FIG. 8B shows the combined effect of tamoxifen (TMX) and ATP on suspensions responding to ATP alone. The presence of 10 $\mu$M tamoxifen enhanced the response to both 3 $\mu$M (P<0.01) and 10 $\mu$M ATP (P<0.05). The values of the fits were: $v_\infty$=98.0±0.4%, $\tau$=10.8±4.9 min (3 $\mu$M ATP alone); $v_\infty$=96.7±0.4%, $\tau$=5.8±2.1 min (3 $\mu$M ATP+10 $\mu$M TMX); $v_\infty$=97.2±0.3%, $\tau$=1.6±1.0 min (10 $\mu$M ATP alone); $v_\infty$=95.7±0.3%, $\tau$=1.4±0.7 min (10 $\mu$M ATP+10 $\mu$M TMX).

FIG. 8C shows the dependence of synergistic shrinkage on ATP concentration. Tamoxifen (6 $\mu$M) was present throughout (N=5). Shrinkage was observed in the simultaneous presence of 10 $\mu$M or 1mM ATP (P<0.01), but not at 1 $\mu$M ATP. The data obtained at 10 $\mu$M and 1mM ATP were not significantly different from each another. The fit obtained at 10 $\mu$M ATP was characterized by $v_\infty$=95.7±0.7% and $\tau$=6.6±3.2min.

In FIG. 9A, at a holding potential of −60 mV, 1mM ATP produced reversible and reproducible increases in inward current in the cultured bovine PE cell of the panel.

In FIG. 9B, the negatively-charged chloride-channel blocker NPPB partially inhibited the ATP-stimulated current of the cell of the cell patched, even at −6 mV.

In FIG. 9C, in the freshly-dissociated cell of the panel, increasing concentrations of ATP (10 $\mu$M, 100 $\mu$M and 1mM) elicited increasing large stimulations, partially reversible at 1 mM before losing the seal. These effects of ATP alone were observed only in half of the total cultured and freshly-dissociated cells studied.

In FIG. 10A, neither ATP (10 mM) nor tamoxifen (6 $\mu$M) separately produced substantial shrinkage, whereas even 10 $\mu$M ATP added together with 6 $\mu$M tamoxifen substantially enhanced the baseline shrinkage. The values of the fits were: $v_\infty$=96.2±0.6%, $\tau$=15.9±5.2 min (Control), 97.7±0.2%, $\tau$=2.2±0.8 min (10mM ATP alone); $v_\infty$=97.2±0.3%, $\tau$=1.6±1.0 min (10 $\mu$M ATP alone); and $v_\infty$=92.8±0.8%, $\tau$=11.4±0.3 min (10 $\mu$M ATP+6 $\mu$TMX) (N=6, P<0.01).

Figure 10A:
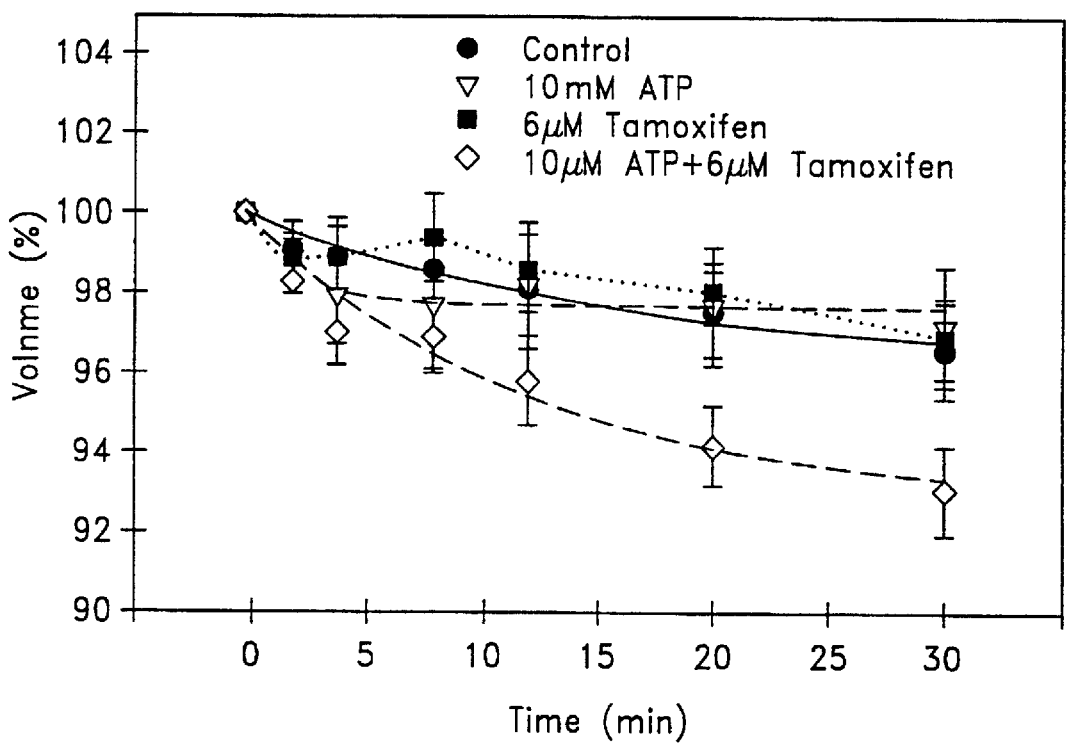
FIGS. 10A–10B. show the synergism between tamoxifen and ATP on isosmotic cell volume of PE cells.
Figure 10B:
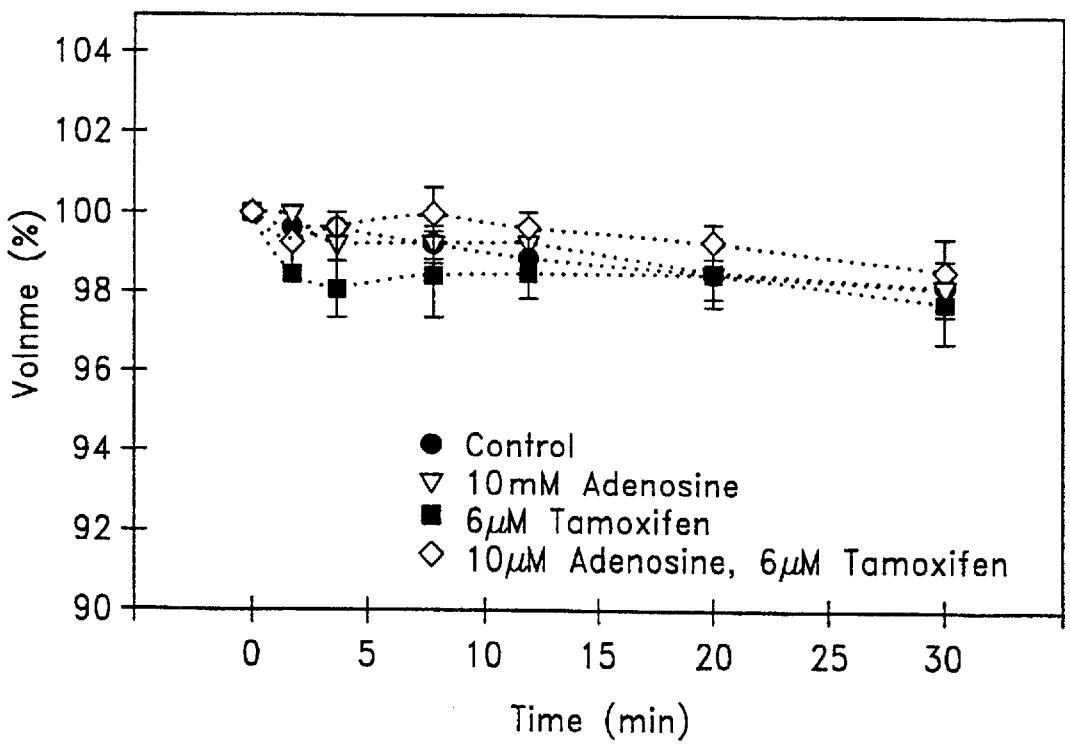

In contrast, in FIG. 10B, no such synergism was noted between tamoxifen (6 $\mu$M) and adenosine (10 $\mu$M) (N=4).

Figure 11:
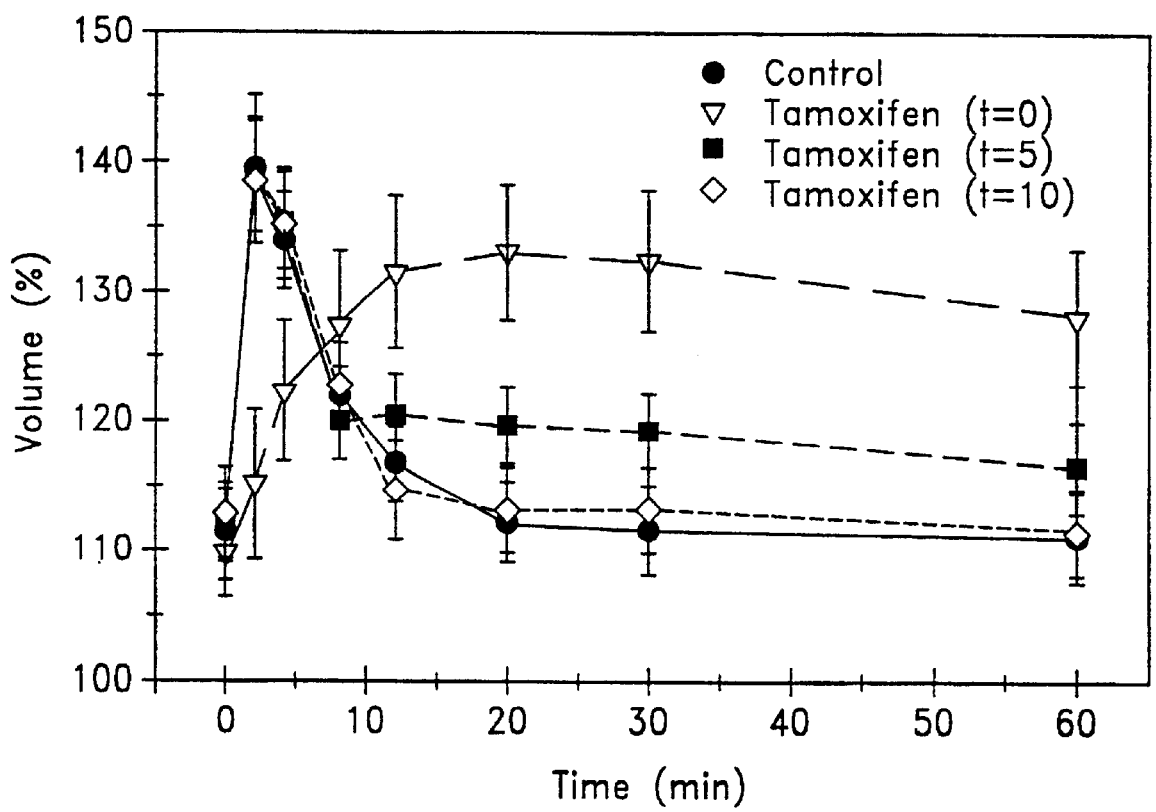

FIG. 11 shows the effect of tamoxifen on the regulatory volume decrease (RVD) of NPE cells. Gramicidin D (5 $\mu$M) was present in all suspensions to provide an exit pathway for $K^+$. In the absence of tamoxifen (TMX), the NPE cells displayed a regulatory volume response to hypotonic swelling with a half-time of ~5 min (N=5). Adding TMX at the conclusion of the RVD (t=10 min) had no effect on cell volume, adding TMX at t=5 min partially inhibited the steady-state response, and adding TMX at the same time as applying the hypotonic stress both slowed the rate of initial slowing and abolished the RVD. This confirms the concept that tamoxifen can inhibit swelling-activated chloride channels of the NPE cells, but selectively enhances the stimulatory effect of ATP on chloride channels by the PE cells.

Figure 12A:
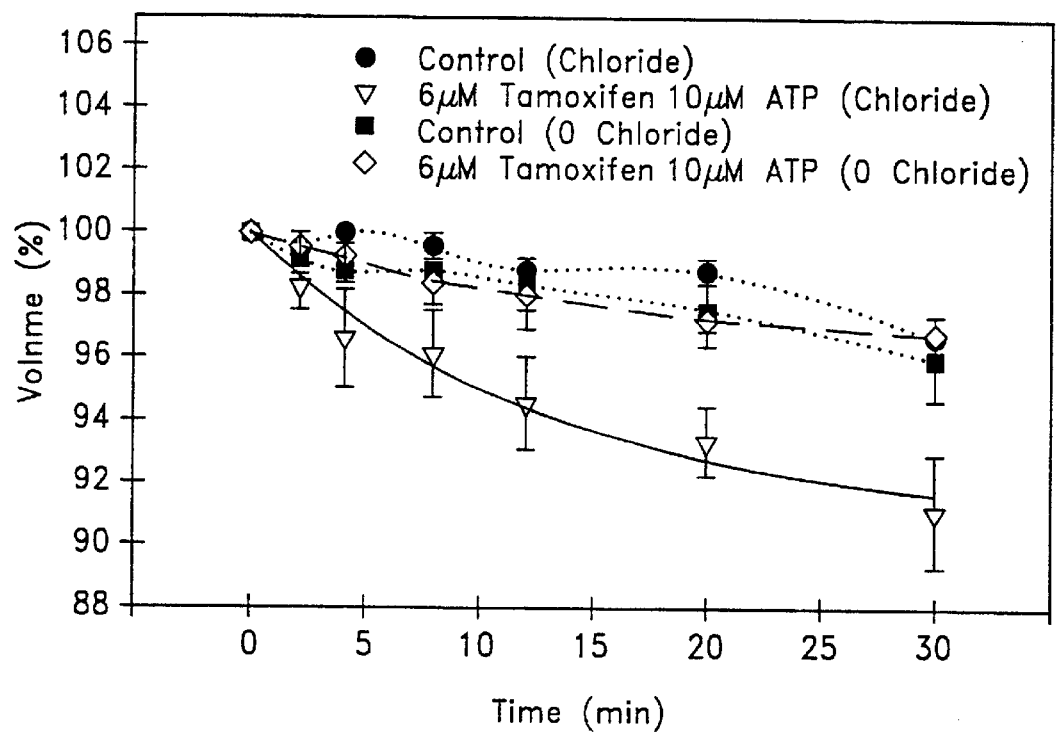
Figure 12B:
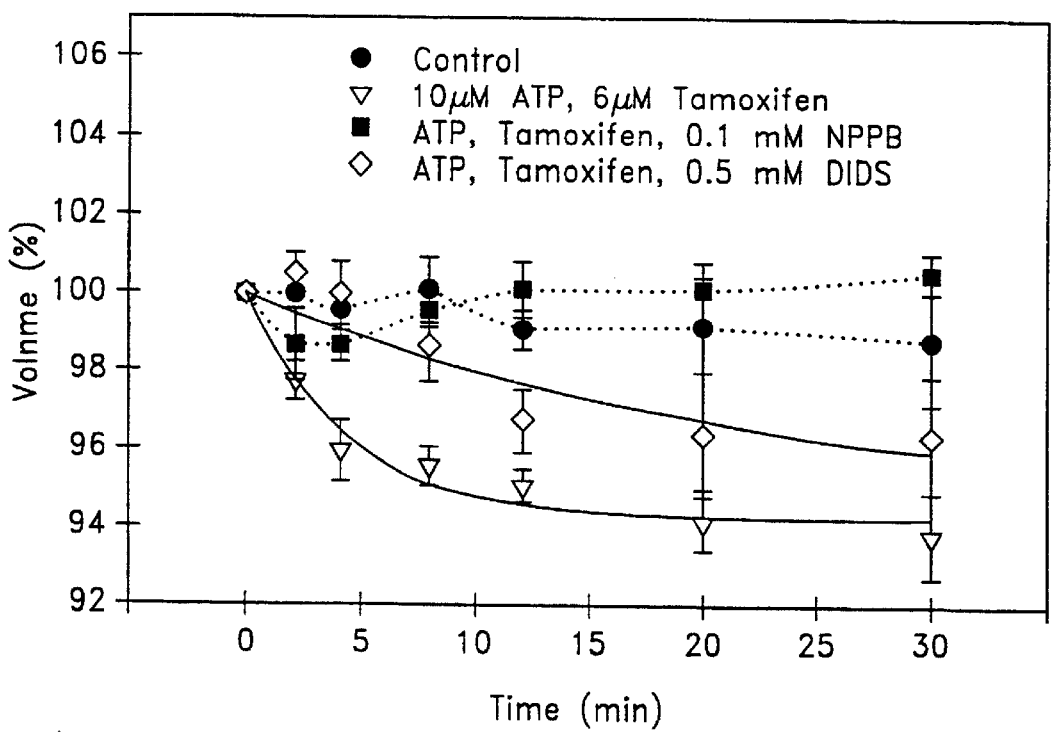

FIGS. 12A–12B show the dependence on $Cl^-$ of the synergistic shrinkage triggered by tamoxifen and ATP in PE cells. Gramicidin D (5 $\mu$M) was present in all suspensions to provide an exit pathway for $K^+$. As shown in FIG. 12A, the simultaneous application of 6 $\mu$M tamoxifen and 10 $\mu$M ATP produced isosmotic shrinkage in the presence of $C^-$ t a steady-state value ($v_\infty$) of 90.6%±1.1% with a time constant ($\tau$) of 13.2±3.2 min (N=4, P<0.01), but not in its absence. FIG. 12B, shows the effect of $Cl^-$ channel blockers on ATP, tamoxifen-activated shrinkage. In the absence of inhibitors, the shrinkage was fit with $v_\infty$=94.2%±0.3% and $\tau$=4.4±0.8min. The $Cl^-$ channel blockers DIDS 500 $\mu$M) reduced and NPPB (100 $\mu$M) each abolished the synergistic shrinkage (N=4, P<0.01).

Figure 13A:
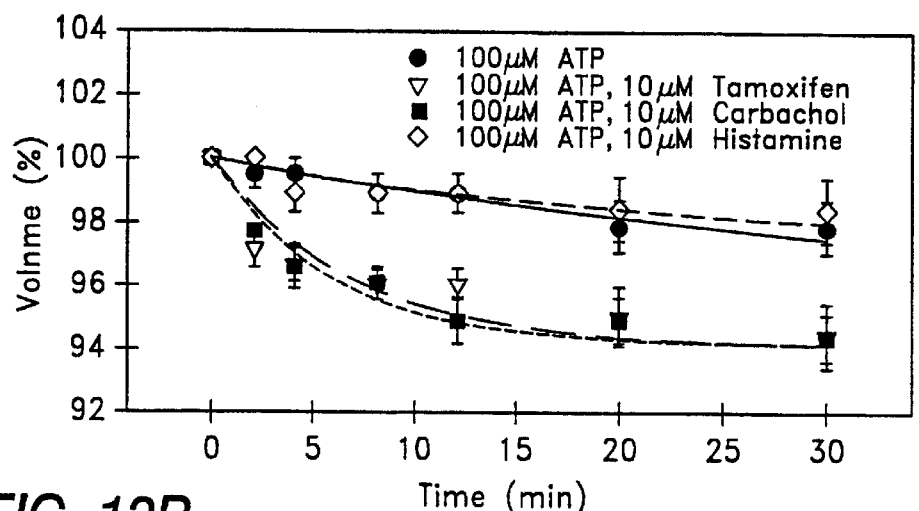
Figure 13B:
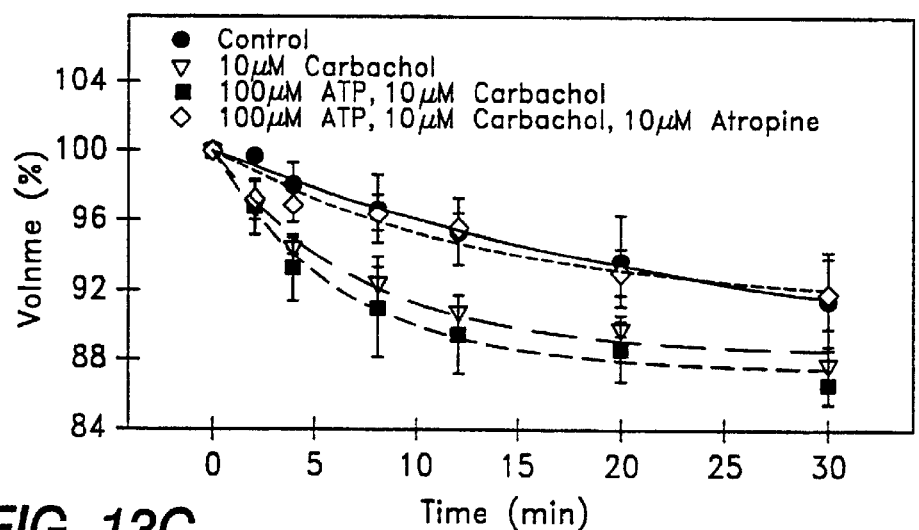
Figure 13C:
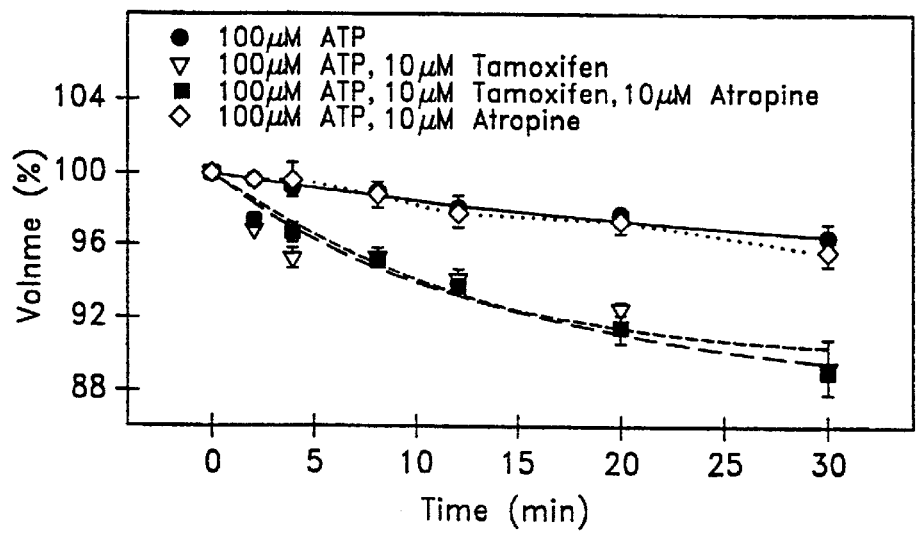

FIGS. 13A–13C. show the potential roles of histamine and muscarinic receptors in PE cells.

As shown in FIG. 13A, in the presence of 100 $\mu$M ATP, either 10 $\mu$M carbachol or 10 $\mu$M tamoxifen, but not 10 $\mu$M histamine, enhanced shrinkage (N=4). The value of the fits were: $v_\infty$=94.9±1.0%, $\tau$=45.2±14.0 min 100 $\mu$M ATP alone); $v_\infty$=94.1±0.6%, $\tau$=6.5±2.3 min (ATP+10 $\mu$M TMX); $v_\infty$=97.4±0.5%, $\tau$=21.0±8.0 min (ATP+10 $\mu$M histamine); $v_\infty$=94.2±0.4%, $\tau$=5.6±1.2 min (ATP+10 $\mu$M carbachol).

In FIG. 13B, carbachol (10 $\mu$M) produced nearly the same degree of shrinkage in the presence or absence of 100 $\mu$M ATP (N=3). This effect was entirely abolished by preincubating for 2 min with 10 $\mu$M atropine and retaining atropine in the test suspension. The fits generated the following values: $v_\infty$=87.5±1.8%, $\tau$=45.2±14.0 min (ATP alone); $v_\infty$=88.4±0.5%, $\tau$=7.2±0.9 min (ATP+TMX); $v_\infty$=87.4±0.5%, $\tau$=6.3±0.8 min (ATP+TMX+atropine); $v_\infty$=91.7±1.6%, $\tau$=13.4±5.2 min (ATP+atropine).

In FIG. 13C, atropine (10 $\mu$M) had no significant effect on the volumetric response to the combined application of 100 $\mu$M ATP and 10 $\mu$M tamoxifen (N=4). The values of the fits were: $v_\infty$==93.9±1.7%, $\tau$=34.8±13.8 min (ATP alone); $v_\infty$=89.6±1.9%, $\tau$=11.3±4.7 min (ATP+TMX); and $v_\infty$=87.8±1.5%, $\tau$=15.1±3.6 min (ATP+TMX+atropine). The cells exposed to ATP and atropine did not display statistically significant shrinkage.

Figure 14A:
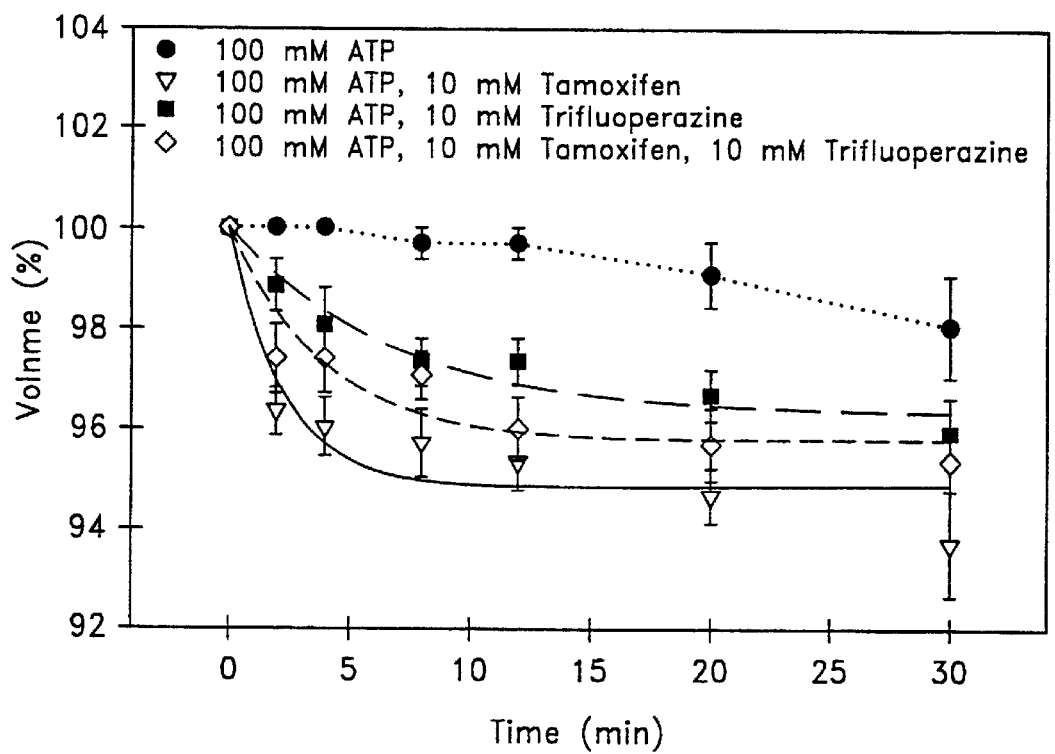
Figure 14B:
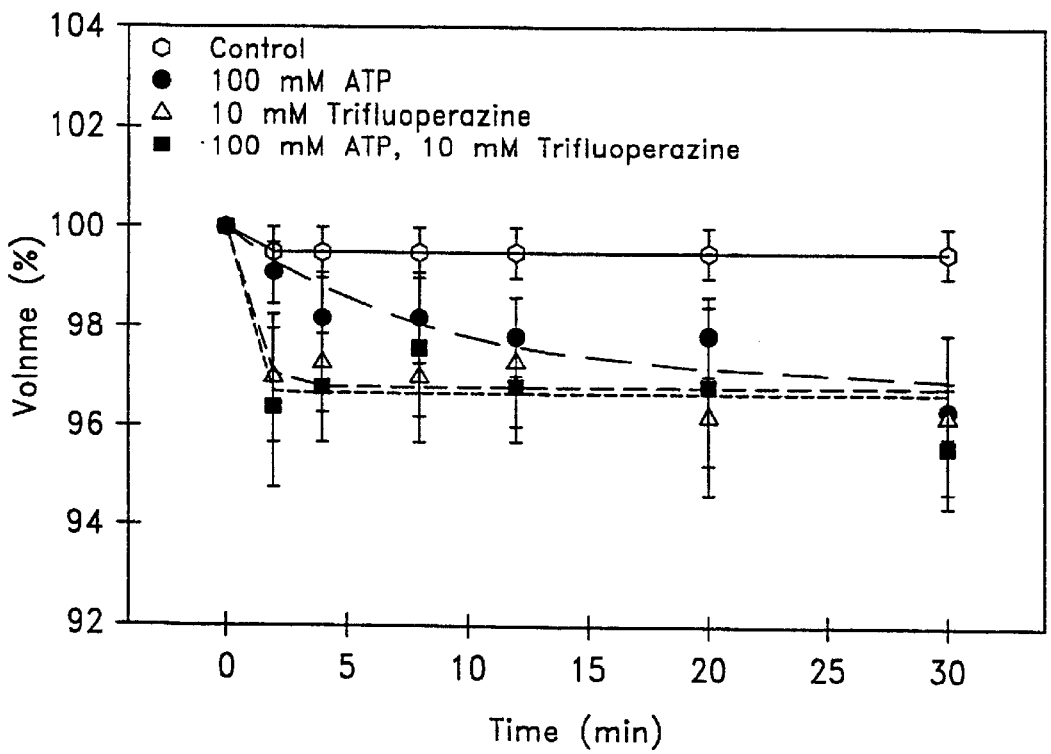

FIGS. 14A–14B show the potential role of calcium/calmodulin in ATP/tamoxifen-mediated cell shrinkage of PE cells.

FIG. 14A shows the interactions of the calcium/calmodulin inhibitor trifluoperazine (10 $\mu$M) with ATP (100 $\mu$M) and tamoxifen (10 $\mu$M) on cell volume (N=6). The presence of trifluoperazine reduced the response to the combined application of ATP and tamoxifen. The trajectories displaying significant shrinkage were fit with: $v_\infty=94.8\pm0.4\%$, $\tau=2.2\pm10.8$ min (ATP+TMX); $v_\infty=96.2\pm0.3\%$, $\tau=6.8\pm1.4$ min (ATP+trifluoperazine); $v_\infty=95.7\pm0.4\%$, $\tau=3.9\pm1.2$ min (ATP+TMX+trifluoperazine). The trifluoperazine enhanced the shrinkage produced by ATP alone (P<0.01), but also significantly reduced the response produced by ATP+TMX (P<0.05).

FIG. 14B shows the effects of trifluoperazine (10 $\mu$M) and ATP (100 $\mu$M) on PE cell volume in the absence of tamoxifen (N=5). The shrinkage triggered by trifluoperazine was the same, whether or not ATP was present (P>0.05). The values of the fits were: $v_\infty=99.5\pm0.002\%$, $\tau=0.5\pm0.06$ min (Control); $v_\infty=96.8\pm0.5\%$, $\tau=8.3\pm3.7$ min (ATP alone); $v_\infty=96.8\pm0.2\%$, $\tau=0.9\pm0.6$ min (trifluoperazine alone); $v_\infty=96.7\pm0.3\%$, $\tau=0.5\pm1.5$ min (ATP+trifluoperazine).

Figure 15:
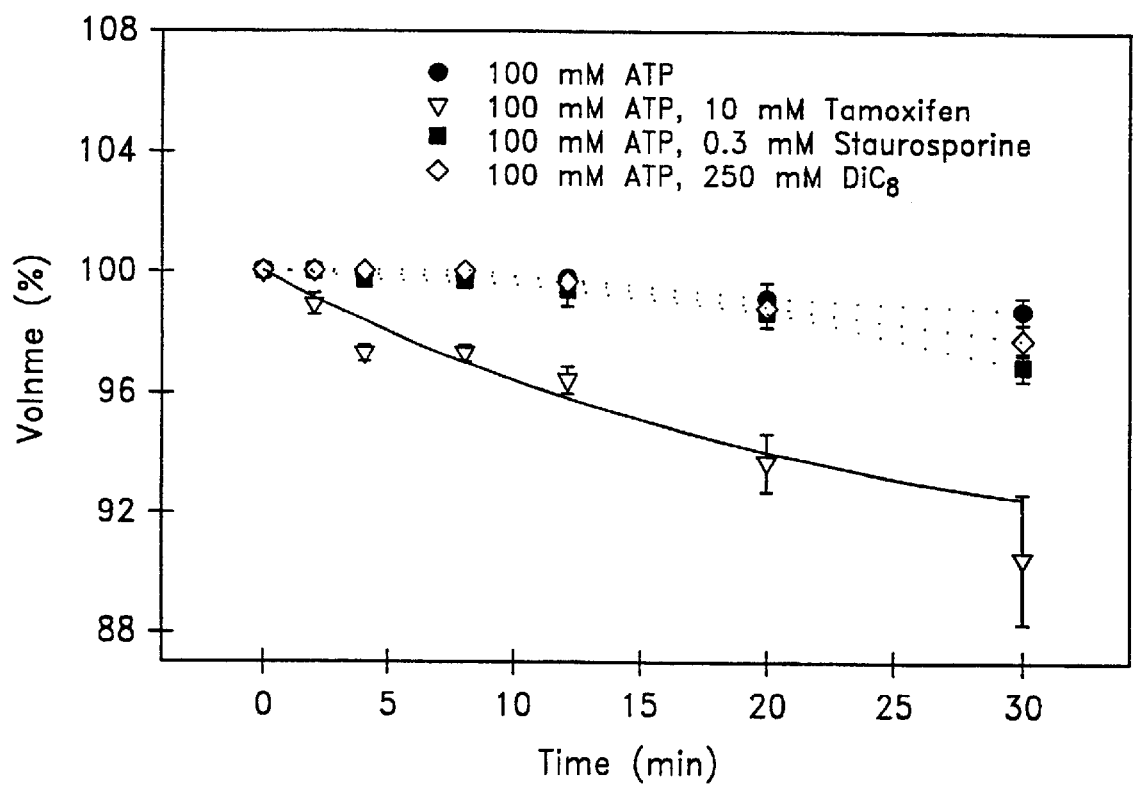

FIG. 15 shows the potential role of protein kinase C on ATP and tamoxifen-mediated PE cell shrinkage. The effect of 250 $\mu$M DiC$_8$ and 0.3 $\mu$M staurosporine with 10 $\mu$M tamoxifen and 100 $\mu$M ATP on cell volume (N=4) was determined. Only the aliquots exposed to tamoxifen and ATP displayed shrinkage ($v_\infty=89.7\pm6.1\%$; $\tau=22.9\pm19.0$ min). The analyses were conducted only with the first 6 time points because of the unusually large shrinkage triggered by ATP+tamoxifen at 30 min.

Figure 16A:
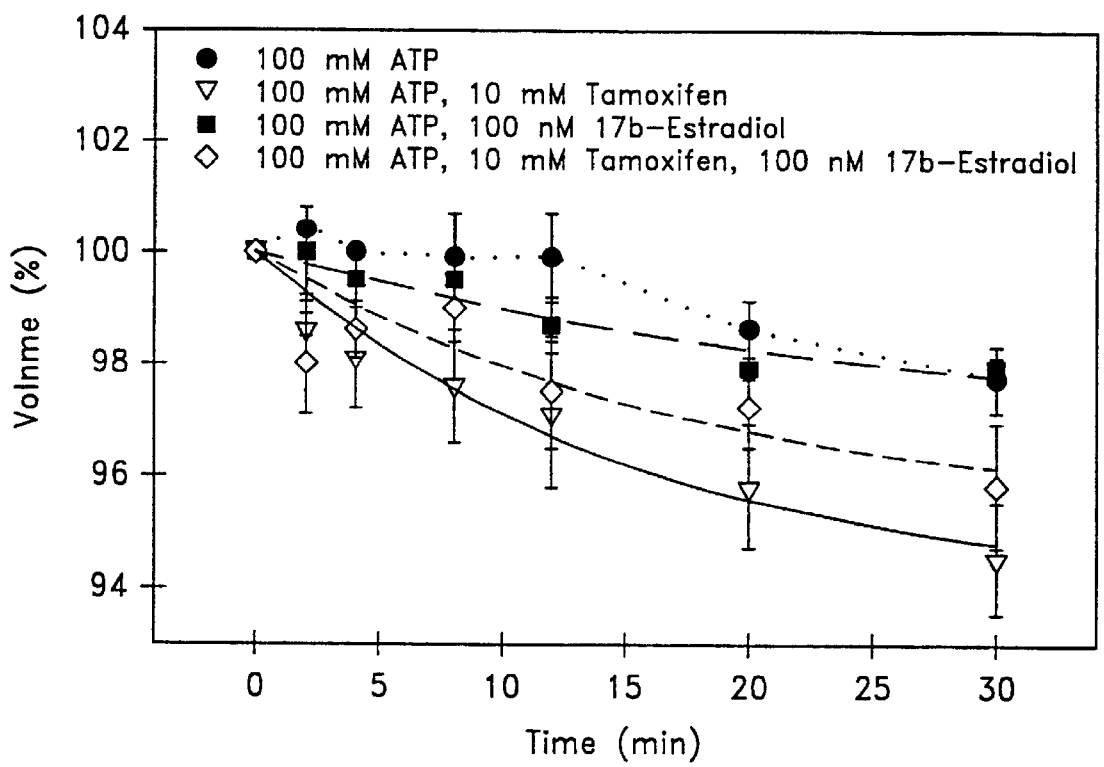
Figure 16B:
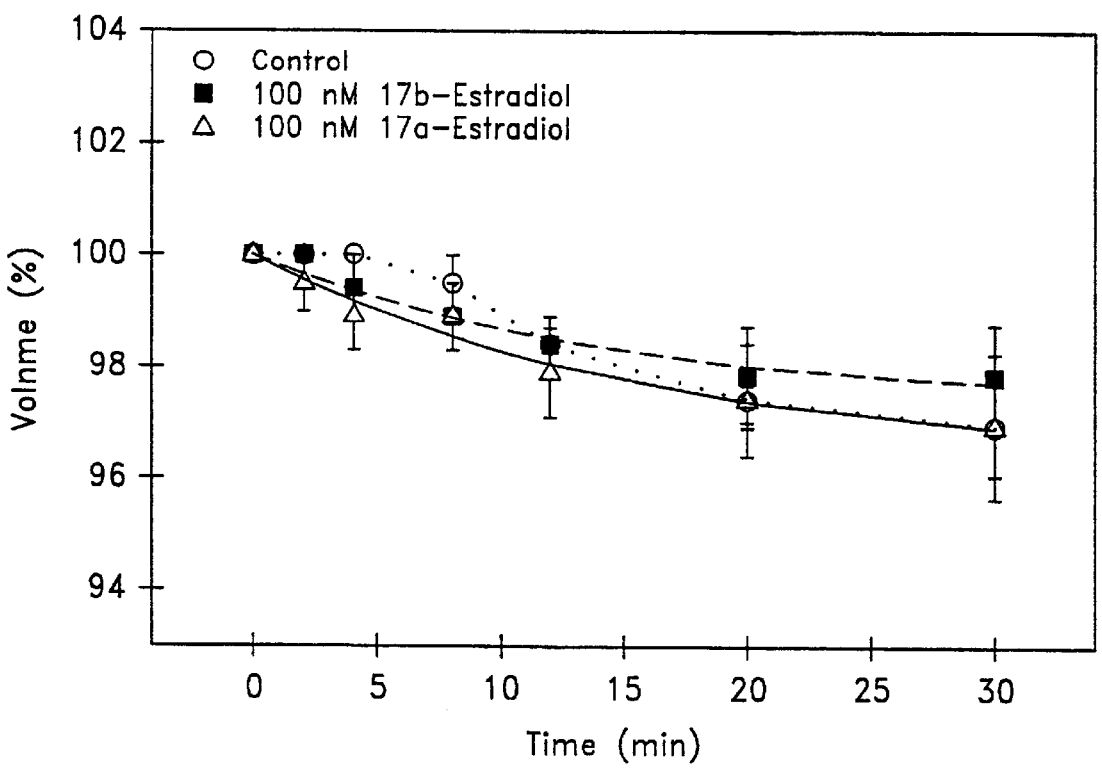

FIGS. 16A–16B show the potential role of estrogen receptors on tamoxifen and ATP-mediated PE cell shrinkage.

FIG. 16A shows the interactions of 17$\beta$-estradiol (100 nM) with ATP (100 $\mu$M) and tamoxifen (10 $\mu$M) on cell volume (N=4). Estradiol together with ATP initiated a small and slow shrinkage, different from the baseline null response to ATP, itself (P<0.05). The maximal response obtained with tamoxifen and ATP ($v_\infty=93.9\pm1.0\%$, $\tau=15.6\pm5.0$ min) was significantly inhibited (P<0.05) by adding estradiol 2 min before initiating the measurements.

FIG. 16B shows the interactions of estradiol and tamoxifen on PE cell volume. At the same 100-nM concentration, the active (17$\beta$-estradiol) and inactive (17$\alpha$-estradiol) forms of the estrogen exerted very small and opposite effects on the time course of cell shrinkage.

Figure 17A:
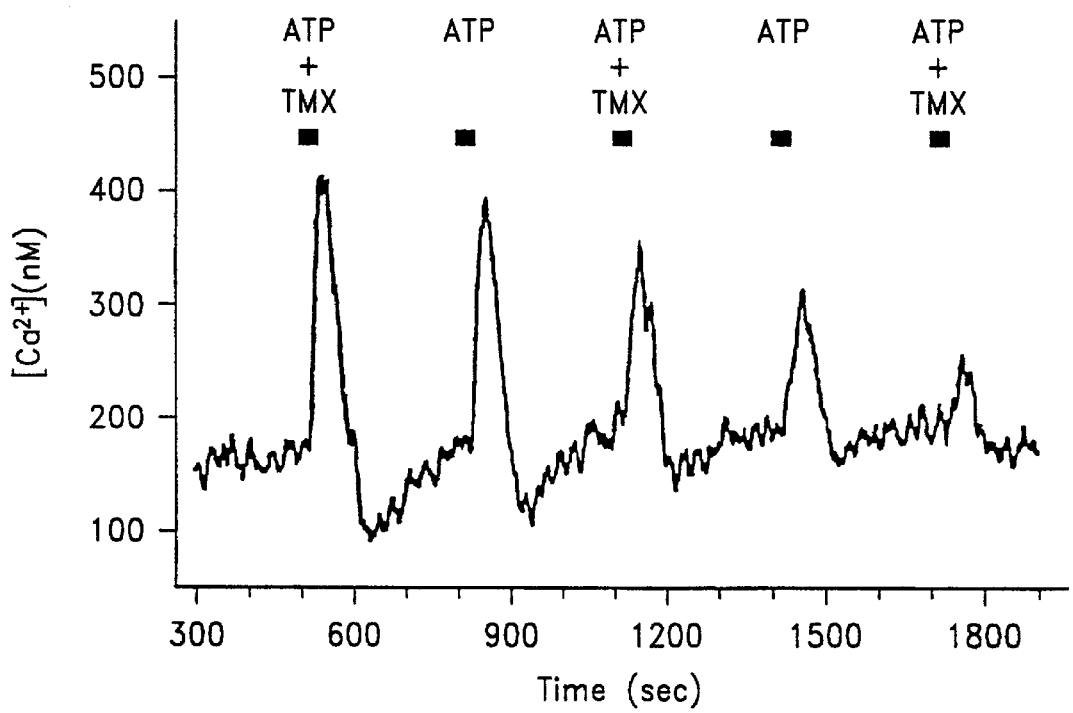
Figure 17B:
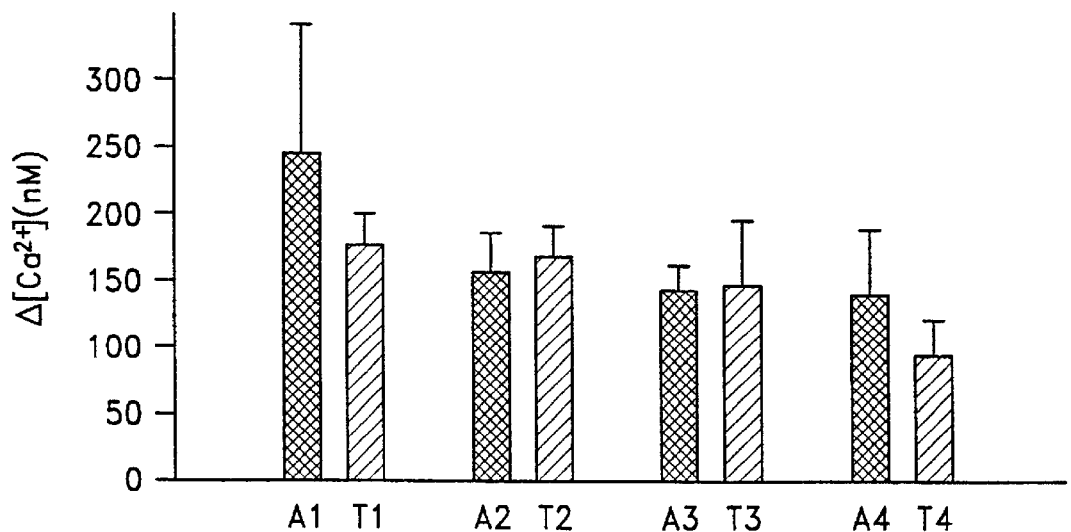

FIGS. 17A–17B show the effects of tamoxifen and ATP on intracellular $Ca^{2+}$ of PE cells.

In FIG. 17A, 100 $\mu$M ATP or 100 $\mu$M ATP+tamoxifen was applied for 20 sec as indicated by the short black bars. The drugs were washed off for 5 min between applications. Although the response attenuates, the presence of tamoxifen does not alter the magnitude of the response. Tamoxifen alone had no significant effect on $Ca^{2+}$ (not shown)

In FIG. 17B, mean results from 7 experiments in which 20-sec applications of 100 $\mu$M ATP were alternated with 20-sec applications of 100 $\mu$M ATP+10 $\mu$M TMX. In order to adjust for the attenuation, two sets of experiments were performed. In the first set illustrated in A, the order of drugs was 1) ATP+TMX, 2) ATP, 3) ATP+TMX and 4) ATP. In the second type of experiment the order was inverted. The magnitude of the $Ca^{2+}$ response when the first application was ATP alone (A1) was compared with experiments in which the first application was with ATP+TMX (T1). Trials in which the second application was with ATP (A2) were compared with trials in which the second application was ATP+TMX (T2), and likewise for the third and fourth applications. There was no significant difference between any of the four pairs (p<0.1, n=3–4)

DETAILED DESCRIPTION OF THE PREFERRED EMBODIMENTS

Figure 1:
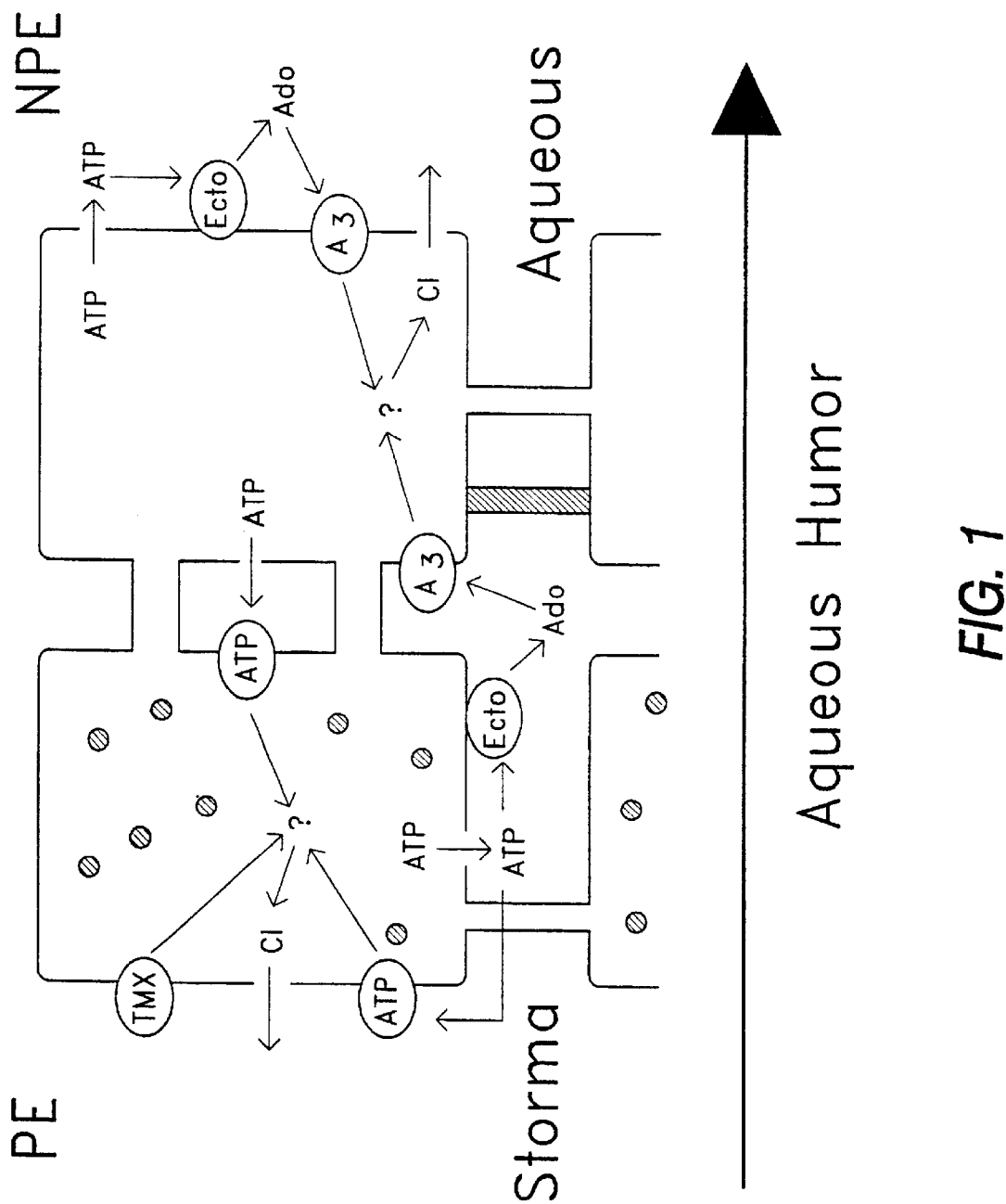
FIG. 1 is a schematic diagram showing the ocular non-pigmented epithelial (NPE) and pigmented epithelial (PE) cells, and the effects of ATP, adenosine (Ado) and tamoxifen (TMX) on the movement of aqueous humor. Ecto=ectoenzymes; $A_3$=$A_3$ subtype adenosine receptor.

The ciliary epithelium of the eye is a bilayer, comprising a deeper layer of pigmented epithelial (PE) cells and a superficial layer of nonpigmented epithelial (NPE) cells (FIG. 1). The proposed mechanism of action of ATP, tamoxifen (TMX) and A3 receptor agonists, such as adenosine (Ado), in influencing aqueous humor secretion is shown in FIG. 1. ATP is released from PE and/or NPE cells. ATP is then converted to adenosine by ecto-enzymes (ecto). The adenosine then binds to A$_3$ receptors on NPE cells, resulting in opening of Cl$^-$ channels. This results in an increase in aqueous humor production and increased intraocular pressure. In addition, simultaneous stimulation by ATP and tamoxifen activates Cl$^-$ efflux from PE cells, leading to a net decrease in aqueous humour formation. ATP acts on P$_2$ receptors of PE cells, promotes opening of Cl$^-$ channels, and a decrease in aqueous humor production resulting in decreased intraocular pressure.

The present invention includes the observation that the A$_3$ subtype adenosine receptor antagonists (referred to herein as A$_3$ antagonists) inhibit shrinkage of NPE cells as determined by measurements of cell volume in isoosmotic solution. This inhibition of cell shrinkage implies a net reduction of secretion of aqueous humor through the NPE cell membrane which would result in a reduction of intraocular pressure (FIG. 1). These A$_3$ receptors are present on human and rabbit NPE cells and underlie the activation of NPE chloride (Cl$^-$) channels by adenosine. In addition, it was found that the antiestrogen tamoxifen, the calcium/calmodulin inhibitor trifluoperazine and the muscarinic agonist carbachol all promoted cell shrinkage in PE cells. The shrinkage of PE cells implies a stimulation of a net reabsorption of aqueous humor through the PE cell membrane towards the stroma, which would result in a net reduction in aqueous humor formation and a reduction in intraocular pressure (FIG. 1). Thus, these compounds, or related compounds, can be used to lower intraocular pressure as a treatment for glaucoma and other ocular conditions in which it is desirable to lower intraocular pressure.

Measurements of short-circuit current across intact rabbit ciliary epithelium, of cell volume in suspended cultured human NPE cells, and of whole-cell currents from patch-clamped cultured human and fresh bovine NPE cells have indicated that adenosine-receptor occupancy stimulates Cl$^-$ secretion in mammalian NPE cells (Carre et al., supra., 1997). As evidenced by the data presented in the examples below, these effects are mediated by A$_3$ receptors. A$_3$ receptors are present in both human HCE cells (a cell line of human NPE cells) and rabbit ciliary body. The A$_3$-selective agonist IB-MECA increased the short circuit current across rabbit iris-ciliary body in the presence of $Ba^{2+}$, a change consistent with an increased efflux of Cl$^-$ from NPE cells. In the presence of gramicidin to isolate the Cl$^-$ conductance, IB-MECA caused human HCE cells to shrink in a dose-dependent manner; the K$_d$ of ~55 nM is consistent with a maximal stimulation of A$_3$ receptors in cardiac myocytes at 100 nM IB-MECA (Shahidullah et al., *Curr. Eye Res.*, 16:1006–1016, 1997). The highly specific A$_3$ agonist Cl-IB-MECA also produced shrinkage of HCE cells in the presence of gramicidin. Gramicidin readily partitions into plasma membranes to form a cation-selective pore and is widely used for studying volume regulation (Hoffmann et al., *Interaction of Cell Volume and Cell Function*, Lang et al., ads., Springer, Heidelberg, Germany, p. 188–248, ACEP Series 14). Under these conditions, release of cell Cl$^-$ becomes the rate-limiting factor in both hypo. (Civan et al., *Invest. Ophthalmol. Vis. Sci.*, 35:2876–2886, 1994) and isosmotic cell shrinkage (Carre et al., supra., 1997).

The A$_3$ antagonists MRS 1097 and MRS 1191 were able to prevent the shrinkage induced by IB-MECA at concentrations far below their $K_i$ for $A_1$ and $A_{2A}$ receptors. The $A_1$ agonist CPA did not have a consistent effect upon cell volume. The $A_{2A}$ agonist CGS-21680 had no effect at low concentrations. The effect of CGS-21680 on shrinkage was only detected at a concentration 500 fold higher than the $K_i$ values for the $A_3$ receptor, and this effect was blocked by the $A_3$ antagonist MRS-1191. The $A_3$ antagonists MRS 1097, MRS 1191 and MRS 1523 blocked the shrinkage produced by 10 μM adenosine; at the concentrations used, <20% of the $A_1$ and $A_{2A}$ receptors could have been occupied by MRS 1097 and <1% of those receptors could have been blocked by MRS 1191 and MRS 1523. Together, these observations indicate that the adenosine/stimulated activation of $Cl^-$ release by the HCE line of human NPE cells is primarily mediated by occupancy of an $A_3$-subtype adenosine receptor.

Adenosine but not ATP shrinks nonpigmented ciliary epithelial (NPE) cells by activating $Cl^-$ channels. Although adenosine had no effect on PE cells, PE cell volume was occasionally reduced by ATP, and was always reduced by simultaneous application of ATP with the antiestrogen tamoxifen. Cultured bovine PE cells were studied volumetrically by electronic cell sorting. ATP alone ($\geq 3$ μM) shrank ~15% of the suspensions, but had little/no effect in most suspensions. Whole cell patch clamping indicated that this baseline response reflected activation of $Cl^-$ permeant channels in a heterogeneous population of cells. The antiestrogen tamoxifen (6–10 μM) enhanced the ATP-triggered shrinkage, whether or not a baseline response to ATP was detected. This was unexpected since swelling-activated $Cl^-$ channels are either blocked (in NPE cells) or unaffected (in PE cells) by tamoxifen. Tamoxifen in itself exerted no consistent effect on PE-cell volume. The tamoxifen, ATP-activated shrinkage required $Cl^-$ release since the response was blocked by removing $Cl^-$ and was inhibited by $Cl^-$ channel blockers (NPPB and BIDS). The modulating effect of tamoxifen could have reflected >5 actions of tamoxifen. Our data argue against actions of tamoxifen to inhibit PKC or calcium/calmodulin and on histamine or carbachol receptors. The cooperative interaction between tamoxifen and ATP was not mediated by an enhanced rise in $Ca^{2+}$. The results indicate that tamoxifen interacts synergistically with ATP to activate $Cl^-$ release by the PE cells. Tamoxifen may act in part by occupying plasma-membrane estrogen-binding sites.

The present results demonstrate that tamoxifen markedly enhanced the effects of extracellular ATP on the transport properties of cultured bovine pigmented ciliary epithelial cells. The synergism was particularly clear in those preparations with little or no baseline response to ATP alone and was detected at ATP and tamoxifen concentrations likely to be physiologically and clinically relevant. In the presence of tamoxifen, an approximately half-maximal response was elicited by 3 μM ATP, a concentration likely reached physiologically by ATP release into the constrained space between the PE cells and the underlying basement membrane (Mitchell et al., supra., 1998). Tamoxifen is used clinically as an antiestrogen by occupying nuclear estrogen-receptor sites (Klinge et al., Oncology Research, 4,:145–150, 1992), and the concentrations applied here (6–10 μM) also appear to be clinically relevant (Stuart et al., Br. J. Cancer, 58, 833–839, 1992).

The precise signaling pathway involved in the modulating action of tamoxifen is presently unknown. In addition to binding to nuclear estrogen receptors (Klinge et al., supra.), and blocking plasma-membrane swelling-activated $Cl^-$ channels (Valverde et al., Pflügers Archive. 425:552–554, 1993; Zhang et al., J. Clin. Investi. 94:1690–1697, 1994; Nilius et al., Pflügers Archive. 428:364–371, 1994; Wu et al., J. Physiol. 491.3:743–755, 1996), tamoxifen has been observed to affect: histamine receptors (Brandes et al., Biochem. Biophys. Res. Commun., 134:601–608, 1986), muscarinic receptors (Ben-Baruch et al., Mol. Pharmacol. 21:287–293, 1981), activation by calcium/calmodulin (Lam, Biochem. Biophys. Res. Commun. 118:27–32, 1984), plasma-membrane estrogen receptors (Hardy et al., FASEB J. 8:760–765, 1994), and protein kinase C activity (O'Brian et al., Cancer Res. 45:2462–2465, 1985). The current data indicate that four of these five latter effects play no role in the synergism between tamoxifen and ATP: (1) because histamine does not alter the response of cell volume to ATP, histamine receptors appear to be irrelevant in the present context. (2) Although carbachol itself shrinks cell volume, the response is not synergistic with ATP, and atropine does not affect the tamoxifen/ATP synergistic effect. Thus, muscarinic receptors are not involved. (3) Protein kinase C (PKC) activity cannot be playing a major role since both activation and inhibition of enzymatic activity produced similar small reductions in volume, 1–2 orders of magnitude smaller than that triggered by tamoxifen and ATP together. At the same concentrations used here, the PKC activator $DiC_8$ and the PKC inhibitor or staurosporine exert large and opposing actions on swelling-activated $Cl^-$ channels of nonpigmented ciliary epithelial cells (Civan et al., Invest. Opthalmol. Vis. Sci. 35:2876–2886, 1994). (4) Finally, calcium/calmodulin antagonism is unlikely to mediate the synergistic effect since the shrinkage produced by another such antagonist (trifluoperazine) was independent of the presence of ATP.

It should be emphasized that although tamoxifen is not acting like carbachol or trifluoperazine, both of these compounds did reduce PE cell volume. Both carbachol and trifluoperazine reduced cell volume on their own, in the absence of ATP. Thus, compounds like trifluoperazine, which inhibit calcium/calmodulin, or substances like carbachol, which stimulate muscarinic receptors, could be used to reduce the production of aqueous humor.

The potential role of binding to plasma-membrane estrogen receptors is less clear. Hardy et al. (supra.) have reported that that tamoxifen activates a large-conductance $Cl^-$ channel with an $EC_{50} \sim 15$ μM applied to NIH 3T3 fibroblasts, but only after stable transfection with MDR1 and after growth in colchicine for >24 hrs. In contrast, no consistent effect of tamoxifen on cell volume was observed in the absence of ATP. Both the active (17β-estradiol) and inactive (17α-estradiol) forms of the estrogen had only slight effects on volume, but 17β-estradiol did enhance the ATP-activated shrinkage slightly. Interestingly, the active (but not the inactive) form of the estrogen also reduced the synergistic effect elicited by tamoxifen and ATP. This indicates that tamoxifen and estrogen compete for binding sites and that tamoxifen is more effective than 17β-estradiol in activating these sites. Since the response to tamoxifen was relatively rapid (within 2 min), it is likely that these receptors are located at the plasma membrane.

ATP produced an elevation in the levels on intracellular $Ca^{2+}$ which attenuated with repeated application, but the response was not affected by the inclusion of tamoxifen. This implies that: 1) the cell shrinkage produced synergistically by ATP and tamoxifen is not mediated by a synergistic elevation in $Ca^{2+}$, and 2) the presence of TMX does not affect the attenuation of the $Ca^{2+}$ response to ATP. This attenuation has been reported previously in ciliary epithelial cells, and it has been suggested that the attenuation is mediated by the inhibition of $IP_3$ production by increasingly elevated levels of PKC (Shahidullah et al., 1997). The inability of tamoxifen to modify the rate of attenuation supports the interpretation that tamoxifen does not act by modifying PKC in these cells.

Thus, cells derived from the pigmented ciliary epithelial cell layer can respond to extracellular ATP by releasing $Cl^-$, and this release is strongly modulated by tamoxifen. Using the fluorescent probe quinacrine, intracellular stores of ATP have been identified in NPE and PE cells in the intact epithelium and in culture (Mitchell et al., supra, 19981. The ATP can be released by both cell types (Mitchell et al., supra., 1998) and metabolized to adenosine by ectoenzymes (Mitchell et al., supra., 1998). Adenosine is known to activate $Cl^-$ channels NPE cells (Carré et al., supra., 1997). Taken together with these previous observations, the current information suggests that ATP can enhance fluid movement in both directions across the ciliary epithelium: increasing secretion by stimulating NPE cells (indirectly through adenosine formation) to release $Cl^-$ into the aqueous humor, and increasing reabsorption by directly stimulating PE cells to release $Cl^-$ into the stroma of the ciliary processes. It is likely that one or more additional factors is necessary to coordinate these opposing purinergic actions to permit ATP to regulate net aqueous humor formation.

Figure 4A:
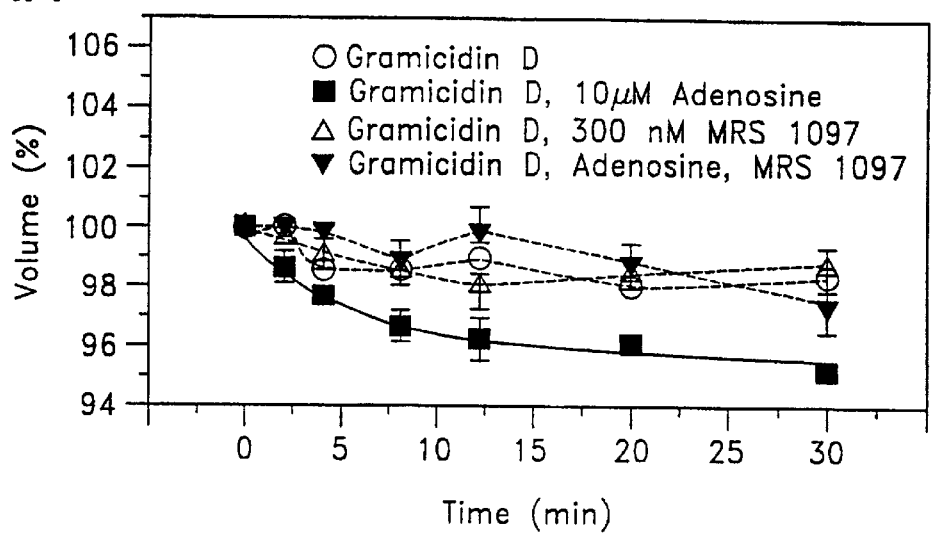
FIGS. 4A–4C shows the effects of selective $A_3$-receptor antagonists on adenosine-stimulated isotonic shrinkage of NPE cells. Application of 300 nM MRS-1097 (FIG. 3A; n=4), 100 nM MRS-1191 (FIG. 3B; n=3) and 100 nM MRS-1523 (FIG. 3C; n=3) all prevented the characteristic shrinkage triggered by nonselective activation of adenosine receptors with 10 $\mu$M adenosine (P<0.01, F-distribution).
Figure 4B:
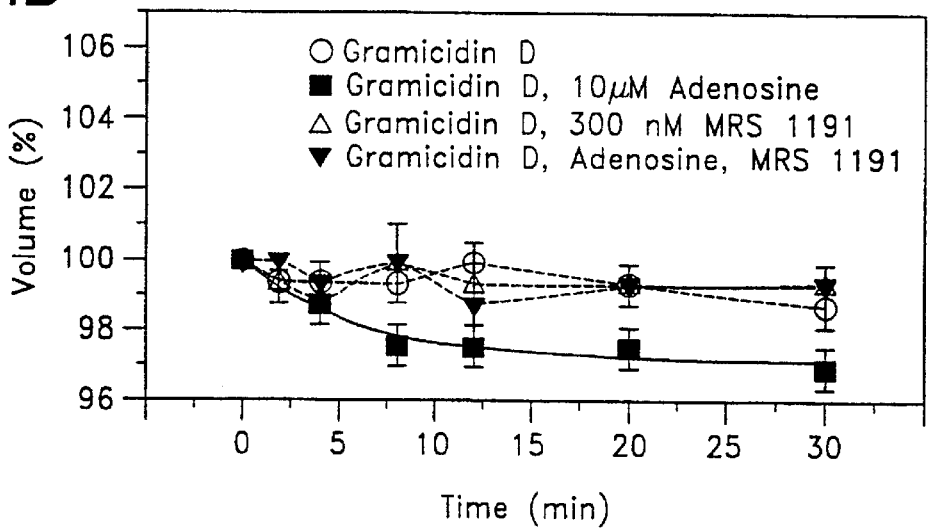
Figure 4C:
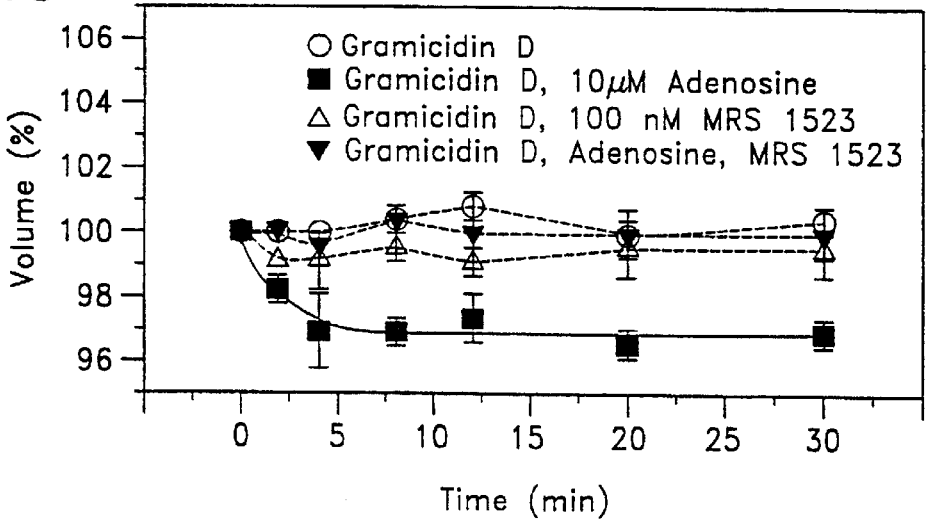

This putative coordination could be provided in at least two ways. In principle, ATP could be released heterogeneously throughout the epithelium. Little information is as yet available on this point, but ATP release triggered by anisosmotic swelling appears to be comparable for NPE and PE cells (Mitchell et al., supra., 1998). An alternative possible mechanism would be for a regulator, like tamoxifen, to modify the effects of purines on $Cl^-$ release at the contralateral surfaces of the ciliary epithelium. In the absence of tamoxifen, physiologic concentrations (~3 $\mu$M) of adenosine stimulate $Cl^-$ release by NPE cells (Carré et al., supra., 1997), whereas even higher concentrations of ATP usually had little effect on release by PE cells . Under these conditions; ATP release would favor secretion. In contrast, in the presence of 6–10 $\mu$M tamoxifen, at least some of the $Cl^-$ channels of the NPE cells are blocked (Wu et al., supra.; FIG. 4), and ATP is far more effective in stimulating $Cl^-$ release from PE cells. Under these latter conditions, ATP release is expected to favor reabsorption.

The data presented below demonstrates the ability of various agents to block shrinkage of NPE cells and to promote shrinkage of PE cells . The net effect of these agents would be to reduce intraocular pressure in vivo. The use of four chemical classes of $A_3$ receptor antagonists for reduction of intraocular pressure is also contemplated: dihydropyridines, pyridines, pyridinium salts and triazoloquinazolines. These generic compounds are shown in Appendix A, along with the possible substituents at each variable position of the compound. These classes of compounds are also described in PCT/WO97/27177.

In addition to the particular $A_3$ receptor antagonists discussed in the examples below: MRS-1097 (3-ethyl 5-benzyl-2-methyl-6-phenyl-4-styryl-1,4-(±)-dihydropyridine-3,5-dicarboxylate), MRS1191 (3-ethyl 5-benzyl-2-methyl-6-phenyl-4-phenylethynyl-1,4-(±)-dihydropyridine-3,5-dicarboxylate) (Jiang et al., *J. Med. Chem.* 40:2596–2608, 1997), and MRS-1523 (Li et al., *J. Med. Chem.* 42:706–721, 1999), the use of any $A_3$ receptor antagonist or analog thereof to reduce intraocular pressure is within the scope of the invention. Other $A_3$ receptor antagonists for use in the present invention are described by Jacobson (*Trends Pharmacol. Sci.* 19:184–191, 1998) and include MRS-1334 (3-ethyl 5-(4-nitrobenzyl) 2-methyl-6-phenyl-4-phenylethynyl-1,4-(±)-dihydropyridine-3,5-dicarboxylate)), MRS-1067 (3,6-dichloro-2'-(isopropoxy)-4'-methylflavone), MRS-1220 (9-chloro-2-(2-furyl)-5-phenylacetylamino[1,2,4]triazolo[1,5-c]quinazoline), L249313 (6-carboxymethyl-5,9-dihydro-9-methyl-2-phenyl-[1,2,4]-triazolo[-5,1-a][2,7]naphthyridine) and L268605 (3-(4-methoxyphenyl)-5-amino-7-oxo-thiazolol[3,2]pyrimidine), VUF8504 (4-methoxy-N-[2-(2-pyridinyl) quinazdin-4-yl]benzamide) and the like.

In a particularly preferred embodiment, the $A_3$ antagonist 2,4-diethyl-1-methyl-3-(ethylsulfanylcarbonyl)-5-ethyloxycarbonyl-6-phenylpyridium iodide (MRS 1649, 11) is used to reduce intraocular pressure. The synthesis of this compound is described in Example 15. This 3,5-diacyl-1,2,4-trialkyl-6-phenylpyridinium derivative displays a unique high water solubility (43 mM) and can be extracted readily into ether. In addition, the prodrug form of this compound, the corresponding 1-methyl-1,4-dihydropyridine, can be oxidized to form compound 11 in vitro in the presence of a tissue homogenate. Thus, it is contemplated that prodrug forms of $A_3$ receptor antagonists (e.g., compounds 24 and 25) can be administered to the eye which will then be converted to the active antagonists which will reduce intraocular pressure.

The determination of whether a compound can act as an $A_3$ receptor antagonist can be determined using standard pharmacological binding assays. Similarly, although the antiestrogen tamoxifen is exemplified herein, other antiestrogens are also contemplated, including, but not limited to, 4-hydroxy tamoxifen, toremifine, icosifene, droloxifene, LY117018, ICl 164,384, ICl182,780, RU 58,668, EM-139, EM-800. EM-652, GW 5638, and the like Lowering of intraocular pressure with a combination of an antiestrogen and ATP, or any compound capable of promoting ATP release from NPE cells, is also contemplated. Finally, although the calcium/calmodulin antagonist trifluoperazine is exemplified herein, the use of any calmodulin antagonist for lowering intraocular pressure is also within the scope of the invention including, but not limited to calmidazolium chloride, calmodulin binding domain, chlorpromazine HCl, melittin, phenoxybenzamine HCl, trifluoperazine dimaleate, W-5, W-7, W-12 and W-13. These compounds are available from Calbiochem, San Diego, Calif. The use of analogs of the above-identified compounds for the reduction of intraocular pressure is also within the scope of the present invention.

These agents can be used to treat ocular disorders resulting associated with or caused by an increase in intraocular pressure, such as glaucoma. The agents can be processed in accordance with conventional methods to produce medicinal agents for administration to mammals, preferably humans. The agents can be employed in admixture with conventional excipients, i.e. pharmaceutically acceptable organic or inorganic carrier substances suitable for parenteral, enteral (e.g. oral) or topical application which do not deleteriously react with the agents. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrollidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampules are convenient unit dosages. For enteral application, particularly suitable are tablets, liquids, drops, suppositories or capsules. A syrup, elixir or the like can be used when a sweetened vehicle is employed. Sustained or directed release compositions can be formulated, e.g. liposomes or those wherein the active compound is protected with differentially degradable coatings, e.g. by microencapsulation, multiple coatings, etc. It is also possible to lyophilize the agents for use in the preparation of products for injection.

Topical administration is preferred. For topical application, there are employed non-sprayable forms, viscous to semi-solid or solid forms comprising a carrier compatible with topical application and having a dynamic viscosity preferably greater than water. Suitable formulations include, but are not limited to, solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, ocular permeability, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g. a freon. In a particularly preferred embodiment, the agent is formulated into a pharmaceutical formulation appropriate for administration to the eye, including eye drops, gels and ointments.

For systemic administration, the dosage of the agents according to this invention generally is between about 0.1 $\mu$g/kg and 10 mg/kg, preferably between about 10 $\mu$g/kg and 1 mg/kg. For topical administration, dosages of between about 0.000001% and 10% of the active ingredient are contemplated., preferably between about 0.1% and 4%. It will be appreciated that the actual preferred amounts of agent will vary according to the specific agent being used, the severity of the disorder, the particular compositions being formulated, the mode of application and the species being treated. Dosages for a given host can be determined using conventional considerations, e.g. ,by customary comparison of the differential activities of the subject compounds and of a known agent, e.g. by means of an appropriate, conventional pharmacologic protocol. The agents are administered from less than once per day (e.g., every other day) to four times per day.

Gramicidin, adenosine, 2-chloroadenosine, tamoxifen, ATP, 17$\alpha$- and $\beta$-estradiol, DiC$_8$, carbachol, atropine, histamine, and trifluoperazine were obtained from the Sigma Chemical Co. (St. Louis, Mo.). CPA (N$^6$-cyclopentyladenosine); CGS-21680, IB-MECA, Cl-IB-MECA and MRS-1191 (3-ethyl 5-benzyl 2-methyl-6-phenyl-4-phenylethynyl-1,4-($\pm$)-dihydropyridine-3,5-dicarboxylate) were obtained from Research Biochemicals International (Natick, Mass.). Fura-2 AM was bought from Molecular Probes (Eugene, Oreg.). MRS 1097, and MRS 1523 were provided by Drs. Kenneth A. Jacobson (National Institutes of Health) and Bruce L. Liang (University of Pennsylvania). The compound Cl-IB-MECA (MH-C-7-08; Lot No. CM-VIII-12) was provided by Research Biochemicals International as part of the Chemical Synthesis Program of the National Institute of Mental Health, Contract N01MH30003. DIDS [4,4'-diisothiocyano-2,2'-disulfonic acid] and fura-2 AM were obtained from Molecular Probes, Inc. (Eugene, Oreg.). NPPB [5-nitro-2-(3-phenylpropylamino)-benzoate] and staurosporine were obtained from Biomol Research Laboratories, Inc. (Plymouth Meeting, Pa.).

Values are presented as the means ±1 SE. The number of experiments is indicated by the symbol N. The null hypothesis, that the experimental and baseline measurements shared the same mean and distribution, was tested with Student's t-test and by the upper significance limits of the F-distribution, as indicated. The t-test was applied to compare the significance between single means or single fit parameters. The F-distribution was applied to test whether the time course of volume measurements in different suspensions could reflect a single population of data points.

EXAMPLE 1

Cell Culture

The HCE (human ciliary epithelial) cell line (Carre et al., supra.), is an immortalized NPE cell line obtained from primary cultures of adult human epithelium. Cells were grown in Dulbecco's modified Eagle's medium (DMEM, #11965-027, Gibco BRL, Grand Island, N.Y.) with 10% fetal bovine serum (FBS, A-1115-L, HyClone Laboratories, Inc., Logan, Utah.) and 50 ug/ml gentamycin (#15750-011, Gibco BRL), at 37° C. in 5% CO$_2$ (Wax et al., Exp. Eye Res. 57:89–95, 1993). The growth medium had an osmolality of 328 mOsm. Cells were passaged every 6–7 days and were studied 8–13 days after passage, after reaching confluence.

For the tamoxifen experiments, The cells used were an immortalized PE-cell line from a primary culture of bovine pigmented ciliary epithelium. Cells were grown in Dulbecco's modified Eagle's medium (DMEM, #11965-027, Gibco BRL, Grand Island, N.Y.; and 51–43150, JRH Biosciences, Lenexa, Kans.) with 10% fetal bovine serum (FBS, A-1115-L, HyClone Laboratories, Inc., Logan, Utah.) and 50 $\mu$g/ml gentamycin (#15750-011, Gibco BRL), at 37° C. in 5% CO$_2$ (Yantorno et al., Exp. Eye Res. 49:423–437, 1989). The medium had an osmolality of 328 mOsm. Cells were passaged every 6–7 days and, after reaching confluence, were suspended in solution for study within 6–10 days after passage.

EXAMPLE 2

Measurement of Cell Volume in Isosmotic Solution

The volume of NPE cells was measured as the movement of fluid that underlies a change in NPE cell volume, this is thought to be the same as the movement of fluid which underlines the secretion of aqueous humor (FIG. 1).

A 0.5-ml aliquot of the HCE cell suspension in DMEM was added to 20 ml of each test solution, which contained (in mM): 110.0 NaCl, 15.0HEPES [4-(2-hydroxyethyl)-1-piperazineethanesulfonic acid], 2.5 CaCl$_2$, 1.2 MgCl$_2$, 4.7 KCl, 1.2 KH$_2$PO$_4$, 30.0 NaHCO$_3$, and 10.0 glucose, at a pH of 7.4 and osmolality of 298–305 mOsm. Parallel aliquots of cells were studied on the same day. One aliquot usually served as a control, and the others were exposed to different experimental conditions at the time of suspension. The same amount of solvent vehicle (dimethylformamide, DMSO or ethanol) was always added to the control and experimental aliquots. The sequence of studying the suspensions was varied to preclude systematic time-dependent artifacts (Civan et al., *Exp. Eye Res.* 54:181–191, 1992).

Cell volumes of isosmotic suspensions were measured with a Coulter Counter (model ZBI-Channelyzer II), using a 100-μm aperture (Civan et al., supra., 1994). As previously described (Wax et al., supra., 1993), the cell volume ($v_C$) of the suspension was taken as the peak of the distribution function. Cell shrinkage was fit as a function of time (t) to a monoexponential function:

$$v_C = v_\infty + (v_0 - v_\infty) \cdot [e^{-(t-t_0)/\tau}] \quad \{1\}$$

where $v_\infty$ is the steady-state cell volume, $v_0$ is the cell volume at the first point ($t_0$) of the time course to be fit, and τ is the time constant of the shrinkage. For purposes of data reduction, the data were normalized to the first time point, taken to be 100% isotonic volume. Fits were obtained by nonlinear least-squares regression analysis, permitting both $v_\infty$ and τ to be variables.

In previous studies demonstrating that adenosine causes isotonic cell shrinkage by activating Cl⁻ channels in NPE cells (Carre et al., supra., 1997), the levels of adenosine used were sufficiently high to activate $A_1$, $A_{2A}$, $A_{2B}$ or $A_3$ adenosine receptor subtypes (Fredholm, et al., *Pharmacol. Rev.* 46:143–156, 1994, Fredholm et al., *Trends Pharmacol. Sci.* 18:79–82, 1997; Klotz et al., *Naunyn Schmiedebergs Arch. Pharmacol.* 357:1–9, 1998). In order to differentiate among these receptors, the experiments were repeated in the present study using a series of agonists and antagonists selective for these receptors. As we wished to identify the effects of these receptors specifically on Cl⁻ channels, 5 μM gramicidin D was included in all solutions to eliminate any potential contribution from K⁺ channels. This ionophore readily partitions into plasma membranes to form a cation-selective pore, and is widely used for studying volume regulation (Hoffmann et al., in *Interaction of Cell Volume and Cell Function*, Lang et al., eds., Springer, Heidelberg, Germany, pp. 188–248, (ACEP Series 14), 1993)). Under these conditions, release of cell Cl⁻ becomes the rate-limiting factor in both hypo-(Civan et al., *Exp. Eye Res.* 54:181–191, 1992) and isoosmotic cell shrinkage (Carre et al., supra., 1997).

Figure 2A:
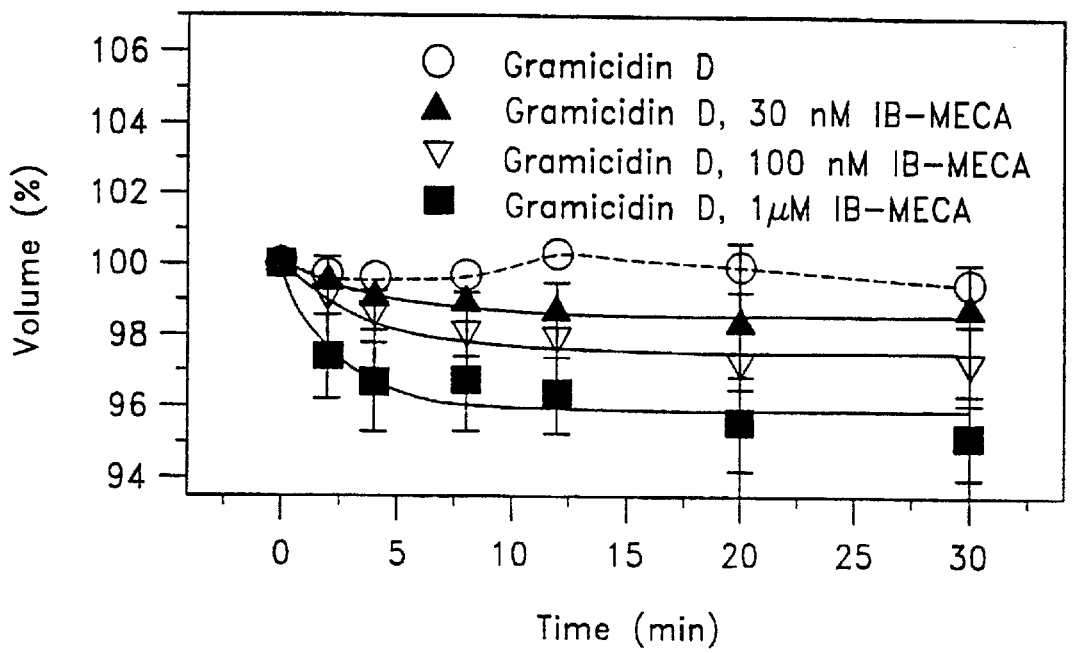
FIGS. 2A–2D show the concentration-response relationship for the $A_3$-selective agonist $N^6$-(3-iodobenzyl)-adenosine-5'-N-methyluronamide (IB-MECA)-stimulated isotonic shrinkage of NPE cells in the presence of 5 $\mu$M gramicidin.
Figure 2B:
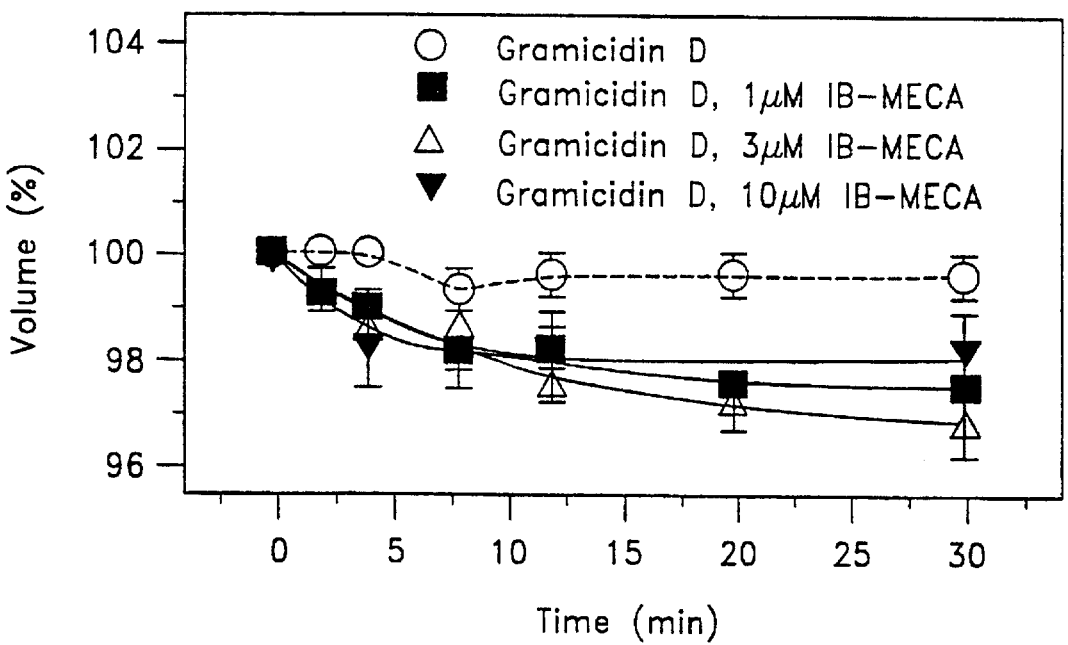
Figure 2C:
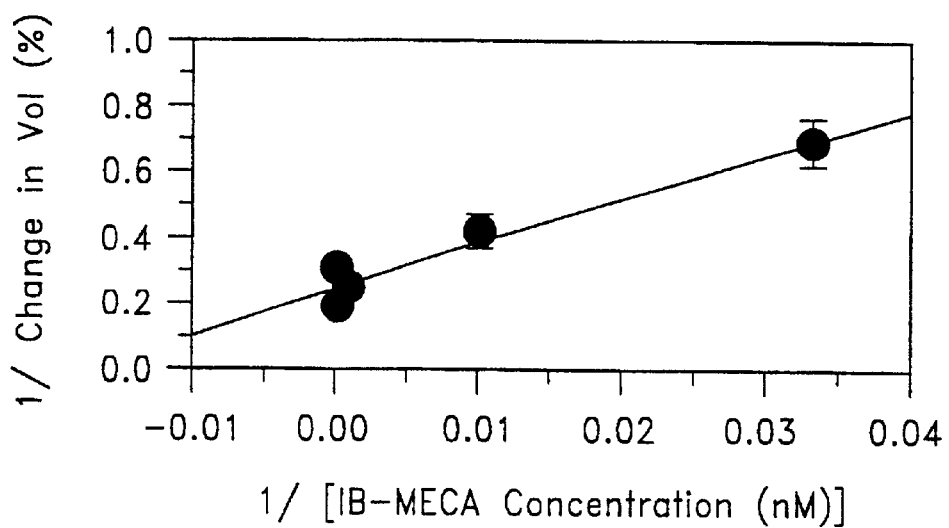
Figure 2D:
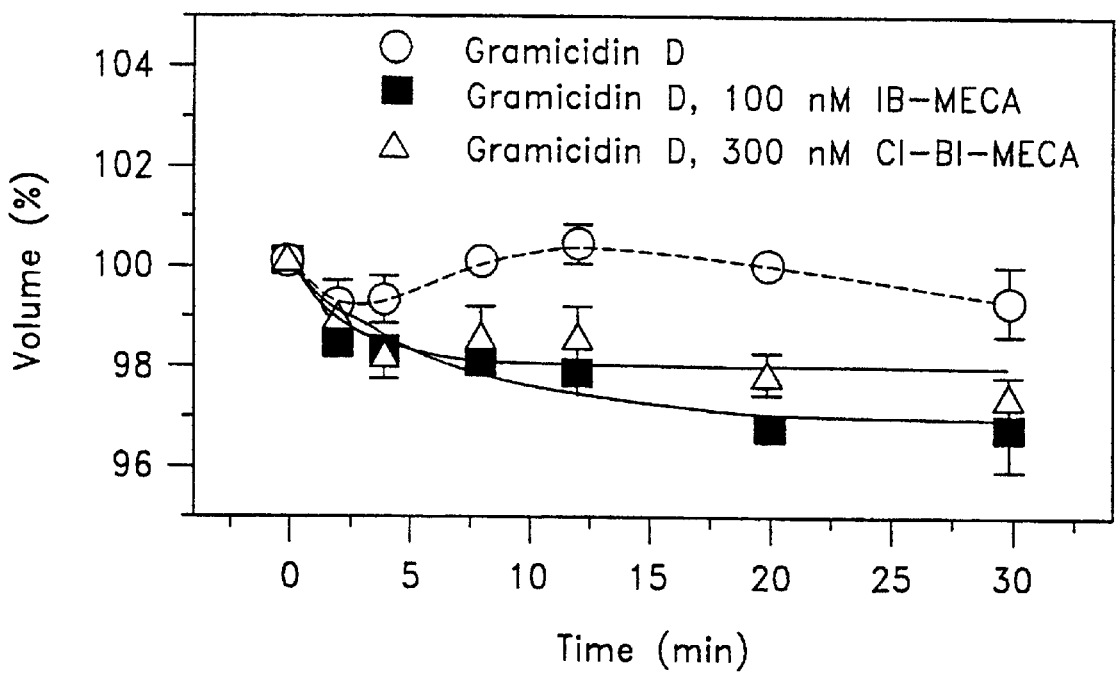

In the presence of gramicidin, the $A_3$ agonist IB-MECA caused the cells to shrink in a concentration-dependent manner (FIGS. 2A–2B). Least-squares analysis of the linearized Lineweaver-Burk plot generated from monoexponential fits of these data indicates that the apparent $K_d$ for the IB-MECA-induced shrinkage was 55±10 nM (FIG. 2C). IB-MECA is a highly selective agonist for the $A_3$ receptor; the $K_i$ for the $A_3$ receptor is 50 times lower than it is for $A_1$ or $A_{2A}$ receptor (Gallo-Rodrigez et al, *J. Med. Chem.* 37:636–646, 1994; Jacobson et al., supra., 1995; Jacobson et al., *FEBS Lett.* 336:57–60, 1993)). Cl-IB-MECA is even more specific for $A_3$ receptors, with a $K_i$ for $A_3$ receptors 2500 times lower than for $A_1$ receptors and 1400 times lower than for $A_{2A}$ receptors. The ability of Cl-IB-MECA to induce cell shrinkage (FIG. 2D) further strengthens the hypothesis that stimulation of $A_3$ receptors stimulates Cl⁻ channels.

Figure 3A:
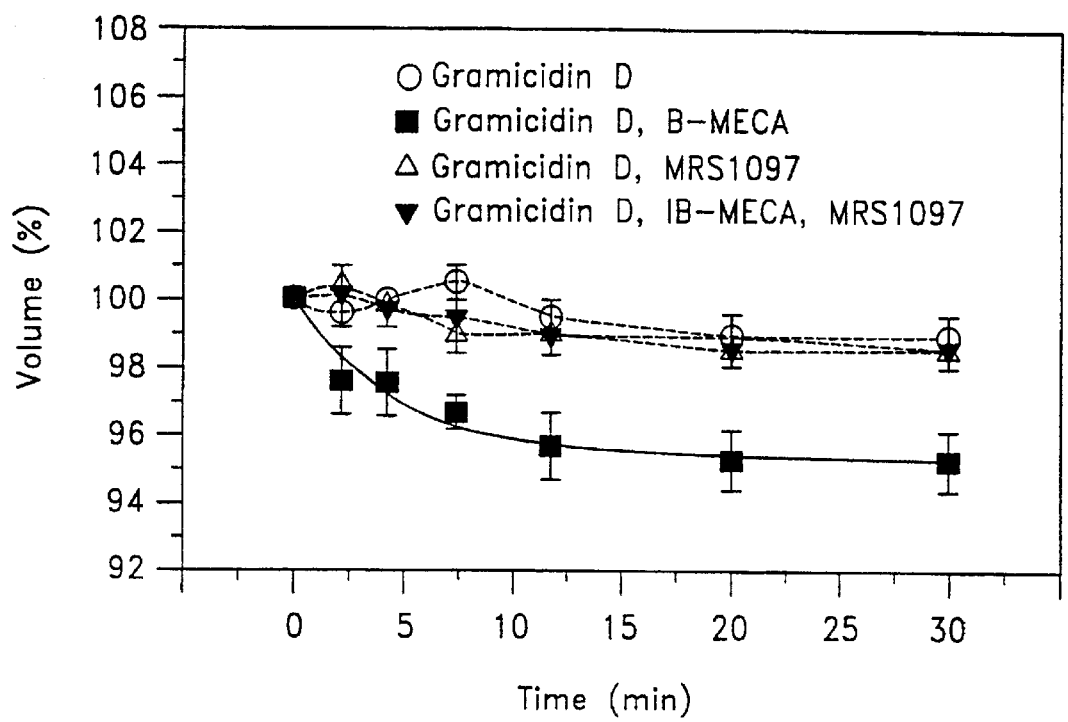
FIGS. 3A–3B show the effect of $A_3$ antagonists on the IB-MECA-stimulated isotonic shrinkage of NPE cells.
Figure 3B:
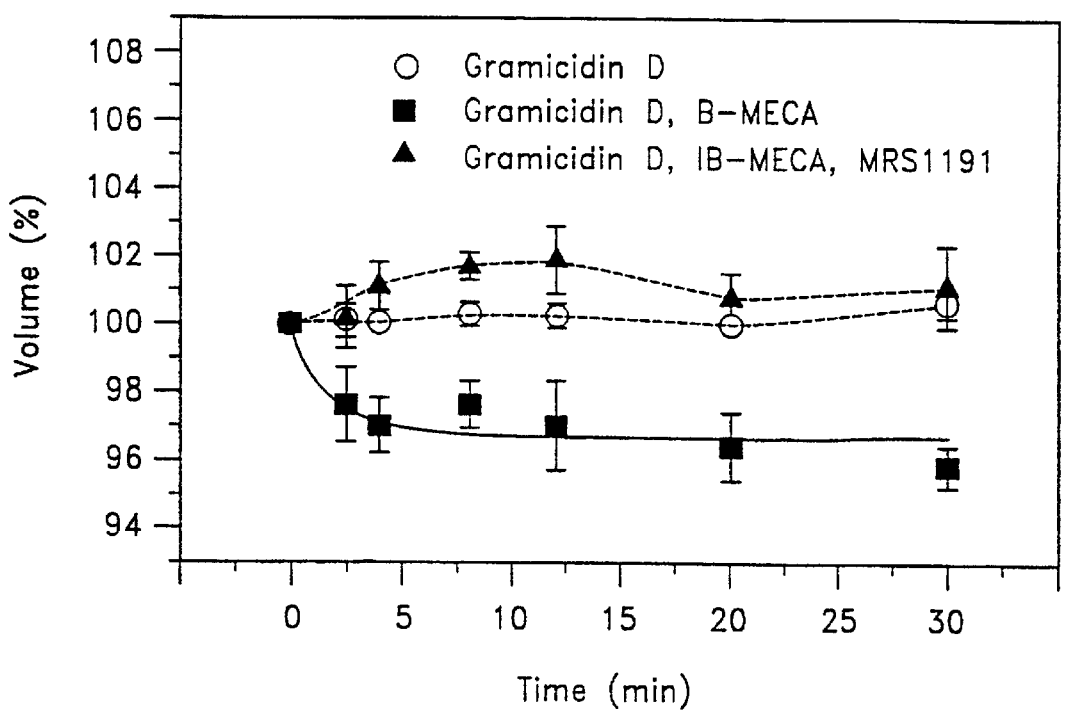

It was also determined whether $A_3$-selective antagonists could prevent the putative $A_3$-mediated shrinkage produced by IB-MECA. Parallel aliquots of suspensions were preincubated with MRS 1097, a selective $A_3$-selective antagonist with $K_i$ values for the binding (in nM) to human $A_1/A_2/A_3$ receptors of 5,930/4,770/108 (Jacobson et al. *Neuropharmacol.* 36:1157–1165, 1997). Preincubation for 2 min with 300 nM MRS 1097 blocked the isoomotic shrinkage characteristically triggered by 100 nM IB-MECA (FIG. 3A). A second highly selective $A_3$ antagonist, MRS 1191, (Jlang et al., *J. Med. Chem.* 39:4667–4675, 1996), with $K_i$ values for the binding (in nM) to human $A_1/A_2/A_3$ receptors of 40,100/>100,000/31.4 (Jacobson et al., supra.) was also used. Preincubation for 2 min with 100 nM MRS 1097 also prevented the subsequent response to 100 nM IB-MECA (FIG. 3B). There was an indication in the results of FIG. 3B that MRS 1191 might actually produce a small amount of cell swelling. This was not a constant finding (FIG. 4B), and may have reflected variations in the background level of $A_3$-receptor occupancy.

The physiologic agonist reaching the adenosine receptors is likely to be the nucleoside adenosine itself, arising from release of ATP by the ciliary epithelial cells and ecto-enzyme activity (Mitchell et al., 1998, supra.). Adenosine triggers isoosmotic shrinkage of cultured human NPE cells with an $EC_{50}$ of 3–10 μM (Civan et al., supra., 1997). In this concentration range, adenosine acts as a nonselective agonist of all four subtypes of the adenosine receptor (Fredholm et al., supra., 1994; Fredholm et al., supra., 1997). As illustrated in FIG. 4, a 2 min preincubation with either 100 nM of the $A_3$-selective antagonist MRS 1191 (FIG. 4B) or 300 nM of the $A_3$-selective antagonist MRS 1097 (FIG. 4A) blocked the shrinkage characteristically produced by 10 μM adenosine. MRS 1523, an $A_3$ antagonist with $K_i$ values for the binding (in nM) to human $A_1/A_2/A_3$ receptors of 15,600/2,050/19 (Li et al., *J. Med. Chem.* 41:3186–3201, 1998) also eliminated the actions of adenosine.

Figure 5A:
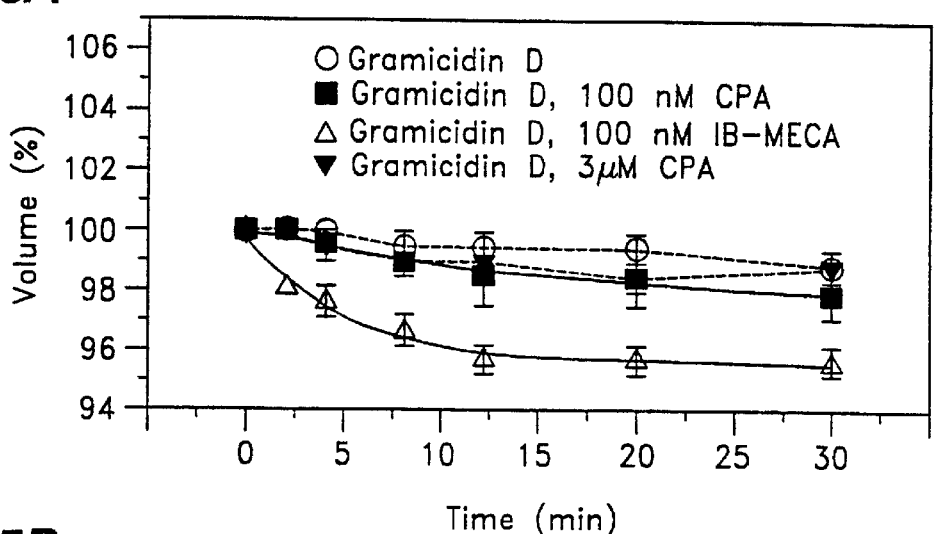
FIGS. 5A–5C show the effects of adenosine-receptor agonists on isoosmotic volume of NPE cells.
Figure 5B:
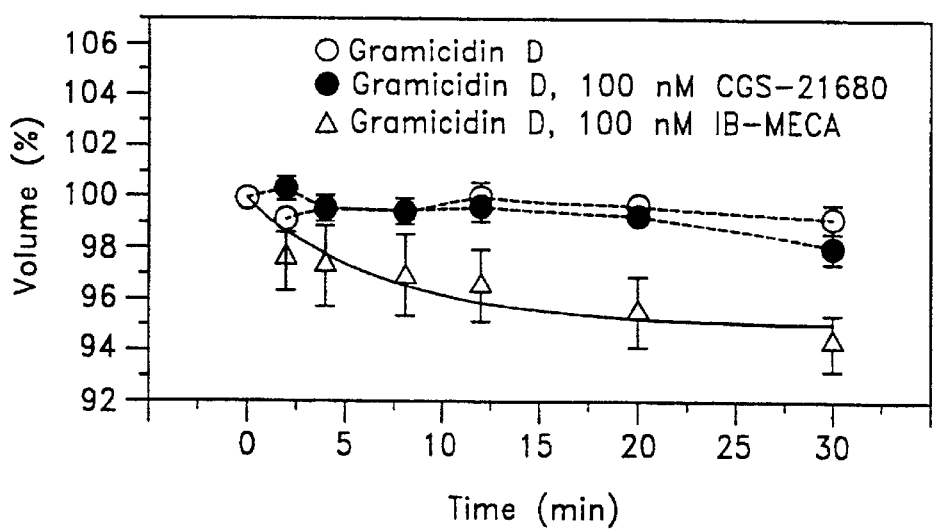
Figure 5C:
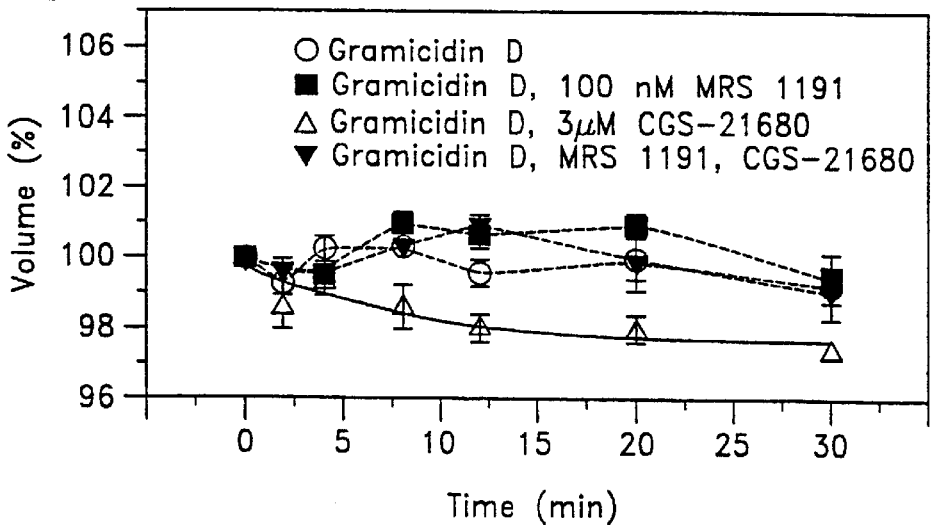

The ability of specific $A_3$ antagonists to inhibit the response to the non-specific adenosine suggests that the contribution of the other receptors to Cl⁻ channel activation was minimal. To test this further, the effect of $A_1$ and $A_{2A}$ agonists were tested. CPA is an $A_1$-selective agonist for $K_i$ and the $A_1$-receptor of 0.6 nM. However, CPA produced no significant shrinkage at 30 nM and 1 μM (data now shown, N=3) and 3 μM (FIG. 5A). A small slow effect of uncertain significance was detected at the intermediate concentration of 100 nM (FIG. 5A). Some cross-reactivity with $A_3$ receptors might be expected, given the $K_i$ of CPA for the $A_3$-subtype of 43 nM (Klotz et al., supra.). CGS-21680 is a widely used $A_{2A}$ agonist with an $IC_{50}$ value of 22 nM for the $A_{2A}$ receptor (Hutchinson et al., *J. Pharmacol. Exp. Ther.* 251:47–55, 1989, Jarvis et al., *J. Pharmacol Exp.* 251:888–893, 1989). CGS-21680 had no detectable effect at 100 nM concentration (FIG. 5B), but did trigger isoosmotic shrinkage at the 30-fold higher concentration (3 μM) (FIG. 5C). However the $K_i$ for the GS-21680 at the $A_3$ receptor is 67 nM (Klotz et al., supra.) and thus CGS-21680 could have been acting through either $A_{2A}$ receptors or $A_3$ receptors at the higher concentration. To distinguish between these possibilities, we preincubated parallel aliquots of suspensions with the antagonist 100 nM MRS 1191. MRS 1191 prevented this shrinkage produced by the high concentration of CGS-21680 (FIG. 5C, P <0.01, F-test), indicating that the shrinkage observed was mediated by cross-reactivity with $A_3$ receptors. As there are presently no high-affinity $A_{2B}$ agonists (Klotz et al., supra), the contribution of $A_{2B}$ receptor stimulation was not pursued, although the ability of $A_3$ antagonists to inhibit the response to 10 μM adenosine (FIG. 5) argues against a role for the $A_{2B}$ receptor. For example, MRS 1191 at 10 μM did not displace radioligand binding to recombinant human $A_{2B}$ receptors, thus it is a truly selective $A_3$ antagonist.

EXAMPLE 3

Effects of IB-MECA on Free Intracellular Calcium Levels

In other cells, stimulation of the $A_3$-receptor can lead to an elevation of intracellular $Ca^{2+}$ (Kohno et al., supra.), so intracellular $Ca^{2+}$ was monitored in HCE cells to provide an additional physiologic assay for the presence of $A_3$ receptors. HCE cells grown on coverslips for 24–48 hrs were loaded with 1–5 µM fura-2 AM for 30–45 min at room temperature. The cells were subject to a post-incubation interval of 20–40 minutes at room temperature before recording began. The coverslips were mounted on a Nikon Diaphot microscope and visualized with a ×40 oil-immersion fluorescence objective. The emitted fluorescence (510 nm) from 10–12 confluent cells was acquired at a sampling frequency of 1 Hz following excitation at 340 nm and 380 nm, and the ratio was determined with a Delta-Ram system and Felix software (Photon Technology International Inc., Princeton, N.J.).Cells were perfused with an isotonic solution consisting of (in mM) 105 NaCl, 6HEPES (acid), 4HEPES ($Na^+$), 2 $CaCl_2$, 1 $MgCl_2$, 4 KCl, 5 glucose and 90 mannitol, at an osmolality of 327 mOsm, pH 7.4. The ratio of light excited at 380 nm vs. 340 nm was converted into $Ca^{2+}$ concentration using the following equation (Grynkiewicz et al., *J. Biol. Chem.* 260:3440–3550, 1985):

$$[Ca^{2+}] = K_d * \left(\frac{(R - R\ min)}{(R\ max - R)}\right)\left(\frac{S_2 f}{S_2 b}\right) \quad \{2\}$$

where $R_{min}$ and $R_{max}$ are the ratio of fluorescence at 340 nM vs. 380 nM in the absence of $Ca^{2+}$, and in the presence of saturating $Ca^{2+}$, respectively. R is the ratio measured experimentally. The $S_2 f$ and $S_2 b$ are the fluorescence emitted at 380 nM in the $Ca^{2+}$ free and $Ca^{2+}$ bound states respectively. An in situ $K_d$ value for fura-2 of 350 nM was used (32). $R_{min}$ was obtained by bathing cells in a $Ca^{2+}$ free isotonic solution containing 10 mM EGTA and 10 µM ionomycin. $R_{max}$ was obtained by bathing the cells in isotonic solution with 10 mM $Ca^{2+}$ and 10 µM ionomycin. Both calibration solutions were maintained at pH 8.0 to facilitate $Ca^{2+}$ exchange through ionomycin. Background fluorescence obtained from confluent HCE cells in the absence of Fura-2 was subtracted from all traces. Mean values of $R_{min}$ and $R_{max}$ were used to obtain the mean responses for a set of experiments. Data were analyzed using a one-sided unpaired t-test.

Figure 6:
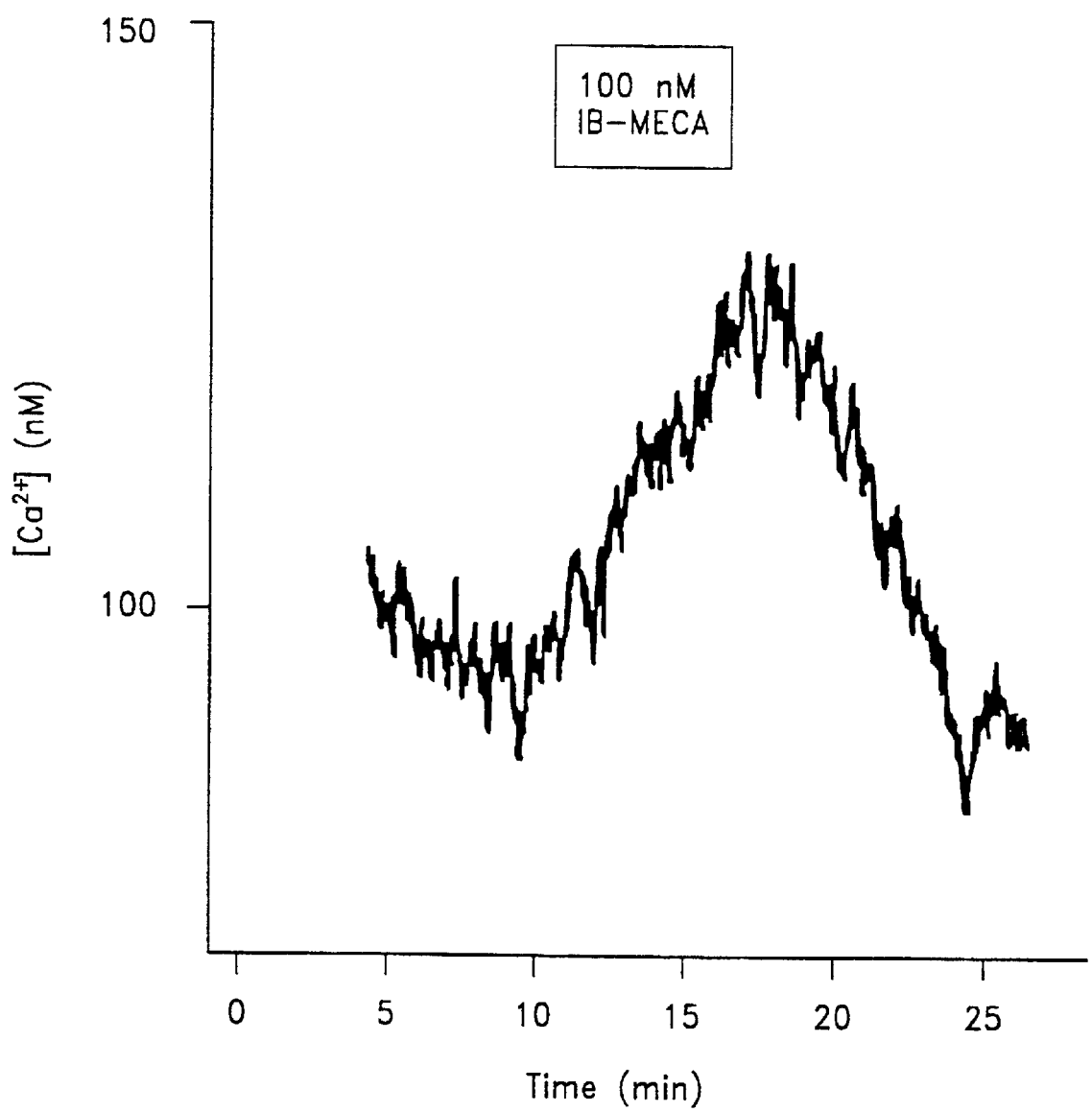

Superfusion of HCE cells with 100 nM IB-MECA produced a sustained, repeatable and frequently reversible increase in the intracellular $Ca^{2+}$ concentration (FIG. 6). The increase in $Ca^{2+}$ was dependent upon concentration, with 100 nM IB-MECA leading to a mean rise of 17±5 nM $Ca^{2+}$ ((p<0.01, N=8) while 1 µM IB-MECA in intracellular $Ca^{2+}$ by 22±6 nM (p<0.05, N=3). Although these changes were relatively small, they w suggesting that these increases in $Ca^{2+}$ could be responsible for physiologic effects occurring on a time scale of minutes to hours.

EXAMPLE 4

Reverse Transcriptase (RT)-PCR Assays

RT-PCR amplifications of RNA from the human and rabbit NPE cells were conducted using primers for the human $A_3$-type adenosine receptor. RNA was isolated from the HCE human NPE cell line using Trizol Reagent (Gibco BRL). Template was synthesized in vitro from the total RNA using an RNA-PCR kit (Gene AMP, Perkin Elmer, Emeryville, Calif.). The reaction mixture contained MuLV reverse transcriptase, an antisense primer specific for the $A_3$ subtype of adenosine receptor, and 1–5 µg of total RNA. Primers for the human $A_3$ receptor (Accession No. X76981) were selected according to the Primer Select program (DNASTAR Inc., Madison, Wis.). The forward (sense) primer (nucleotides 914–937) was: 5'-GCGCCATCATCTTGACATCTTTT-3' (SEQ ID NO: 1). The reverse (antisense) primer (nucleotides 1373-1355) was: 5'-CTTGGCCCAGGCATACAGG-3' (SEQ ID NO: 2). The cDNA was amplified by annealing the set of oligonucleotide primers (0.2 µM) in a final volume reaction of 100 µl in an Omnigene Thermal Cycler (#480, HYBAID, Franklin, Mass.). The PCR reaction was conducted for 35 cycles, each cycle comprising 1 min at 95° C., 1 min at 55° C., and 1 min at 72° C. The final extension was prolonged by 7 min at 72° C. The PCR product was reamplified using the touchdown PCR method with fresh primers and TAQ polymerase, using an annealing temperature ranging from 58° C. to 48° C. The resulting PCR product was size-fractionated by electrophoresis on 1% agarose gel. To sequence the PCR product, a band of the expected size (462 bp) was extracted from low melting-point agarose gel using a Qiaex II Agarose Gel Extraction kit (Qiaex, Calif.). The purified reaction product was directly sequenced on an ABI100 sequencer by the DNA Sequencing Facility at the Cell Center of the University of Pennsylvania and compared with the predicted sequence using a DNASTAR program.

The RT-PCR assay of rabbit A3 message was conducted in the same way with the following changes. RNA was obtained from the tips of New Zealand White rabbit ciliary processes using Trizol Reagent, and was reverse transcribed using 3–6 µg total RNA, MuLV reverse transcriptase and oligo-dT primers. The reaction was carried out at 42° C. for 30 minutes, followed by 5 minutes at 95° C. The PCR reaction and reamplification steps were performed using Amplitaq Gold (Perkin-Elmer, Foster City, Calif.) and 10% glycerol was included in the reamplification step. Specific primers for the rabbit A3 receptor were selected from the rabbit A3 sequence (Accession No. U90718); the forward primer (nucleotides 147–167) was 5'-CAACCCCAGCCTGAAGACCAC-3' (SEQ ID NO: 3) while the reverse primer (nucleotides 608–587) was 5'-TGAGAAGCAGGGGGATGAGAAT-3' (SEG ID NO: 4). Both PCH amplification and reamplification were performed for 35 cycles, each cycle consisting of 1 min at 95° C., 1 min at 58.5° C. and 1 min at 72° C. A final extension cycle of 7 minutes at 72° C. minutes completed the reaction.

The product of the PCR reamplification of rabbit tissue was cloned into the PCR-TOPO vector using the TOPO TA cloning kit (Invitrogen Corporation, Carlsbad, Calif.) following the manufacturer's directions. After transformation, plasmids were isolated using the Wizard Plus Miniprep DNA Purification System (Promega Corporation, Madison, Wis.). The cloned plasmid was cut with EcoR I restriction nuclease, and a band of approximately the expected size (479 bp) was identified by running the cut product on an agarose gel. The plasmid was sequenced from the Sp6 promoter site 80 base pairs proximal to the PCR product. The sequence was compared to the expected rabbit $A_3$ sequence using a DNASTAR program.

From the RT-PCR amplifications of human NPE cells using primers for the human $A_3$ receptor, a fragment of the expected 462-bp size was obtained, and was enhanced by direct PCR amplification of the product. The sequence obtained from the reamplified product was compared to the sequences of known human adenosine receptors using the DNASTAR program. The results displayed a 97.4% similarity to the published base sequence for the $A_3$ receptor, whereas the similarity indices for the other known adenosine-receptor subtypes were all <40% 137.9% for A, (Accession No. 68485), 35.0% for $A_{2A}$ (Accession No. 68486), and 36.7% for $A_{2B}$ (Accession No. 68487) was detected when reverse-transcriptase was excluded from the initial reaction mixture.

RT-PCR amplification was also conducted with rabbit ciliary processes, using primers for the rabbit $A_3$-type adenosine receptor. The RT-PCR product was reamplified, cloned and sequenced. The sequence displayed a 97.4% similarity with the published base sequence for the rabbit $A_3$ receptor There was only 27.9% homology between rabbit $A_1$(Accession No. L01700) and $A_3$ receptors. Sequences are not yet available for the remaining $A_{2A}$- and $A_{2B}$-subtypes of adenosine receptors in the rabbit. Our rabbit product also displayed 75.1% similarity to the human $A_3$ receptor but only <30% similarity indices for the other human adenosine-receptor subtypes (28.2% for $A_1$, 27.7% for $A_{2A}$ and 29.5% for $A_{2B}$). No product was detected when reverse-transcriptase was excluded from the reaction mixture.

EXAMPLE 5

Transepithelial Measurements

Adult male Dutch belted rabbits weighing 1.8–2.4 kg (Ace Animals, Boyertown, Pa.) were anesthetized with pentobarbital and sacrificed (Carre et al., J. Membr. Biol. 146:293–305, 1995). After enucleation, the iris-ciliary body (I-CB) was isolated as previously described (Carre et al., 1995, supra.). The experiments were in accordance with the Resolution on the Use of Animals in Research of the Association for Research in Vision and Ophthalmology.

The pupil and central iris were occluded with a Lucite disc, and the iris-ciliary body was mounted between the two halves of a Lucite chamber (1). The annulus of exposed tissue provided a projected surface area of 0.93 cm². Preparations were continuously bubbled with 95%$O_2$–5%$CO_2$ for maintenance of pH 7.4 in a Ringer's solution comprising (in mM): 110.0 NaCl, 10.0HEPES (acid), 5.0HEPES ($Na^+$), 30.0 $NaHCO_3$, 2.5 $CaCl_2$, 1.2 $MgCl_2$, 5.9 KCl, and 10.0 glucose, at an osmolality of 305 mOsm. $BaCl_2$ (5 mM) was added to the solution to block $K^+$ currents. The transepithelial potential was fixed at 0 mV, corrected for solution series resistance, and the short-circuit current was monitored on a chart recorder. Data were digitally acquired at 10 Hz via a DigiData 1200A converter and AxoScope 1.1 software (Axon Instruments, Foster City, Calif.). Automatic averaging was performed with a reduction factor of 100 to achieve a final sampling rate of 6/min.

Figure 7:
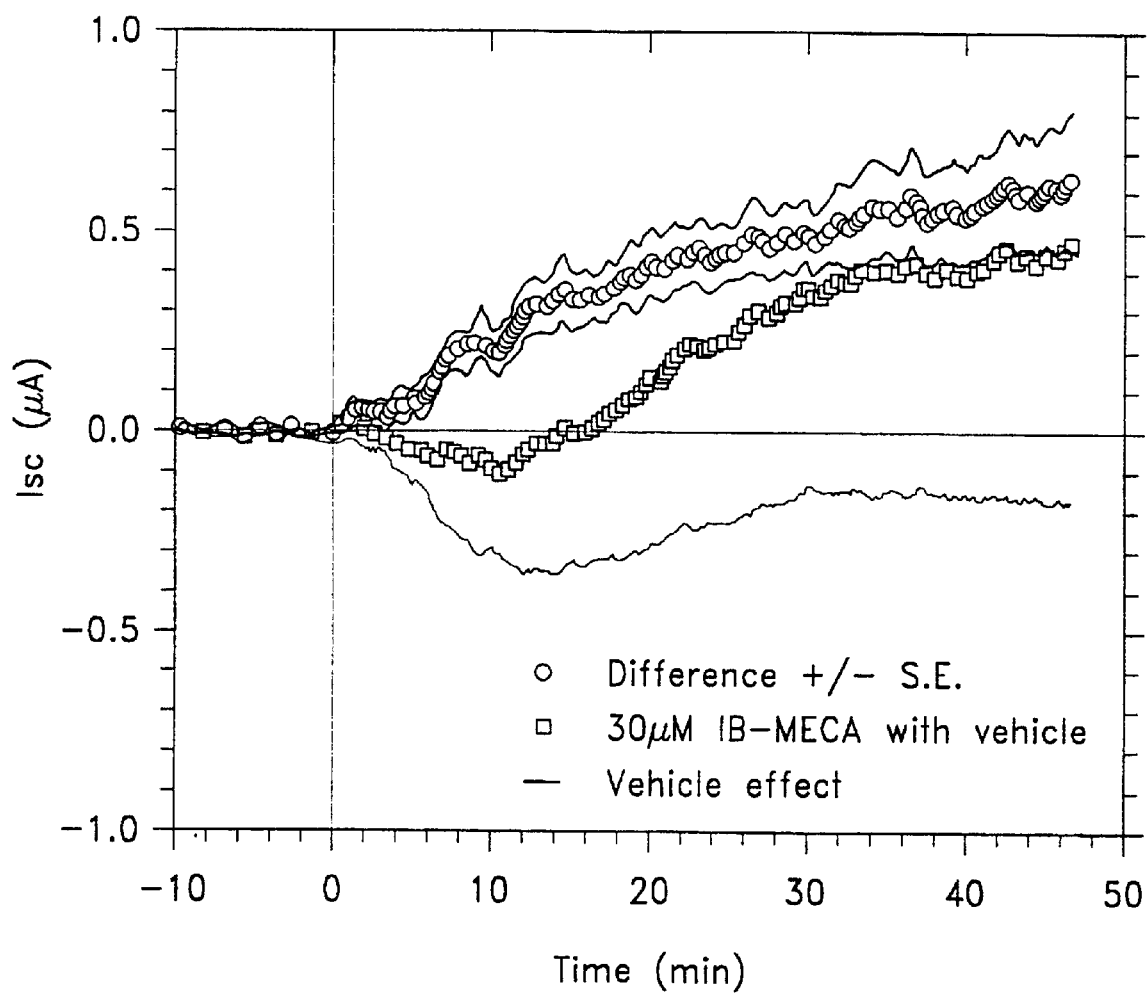

Adenosine in high concentration (100 μM) has been found to increase the short-circuit current across the rabbit ciliary body (Carre et al., supra., 1997). We therefore tested whether a high concentration (30 μM) of the $A_3$ agonist IB-MECA also affected short-circuit current. At this concentration, the vehicle (dimethylformamide) itself exerts significant effects (FIG. 7, lowest trajectory). We corrected for the solvent effect in the following way. Solvent alone was initially introduced (to 0.1%), followed by the same volume of solvent (to 0.2%) containing agonist, and ending with addition of a third identical volume of solvent alone (to a final concentration of 0.3%). The reduction in short-circuit current following the first addition of solvent was always greater than the third. In each of four experiments, we averaged the time courses of the first and third additions to estimate the effect of raising the solvent concentration without agonist from 0.1% to 0.2% during the experimental period. FIG. 7 presents the mean trajectory for the averaged solvent effect, the uncorrected mean time course following exposure to IB-MECA, and the mean trajectory ±1 SE for the solvent-corrected response. The experiments were performed in the presence of 5 mM $Ba^{2+}$ to minimize the contribution of $K^+$ currents. IB-MECA produced a significant increase in the short-circuit current; an increase in short-circuit current in the presence of $Ba^{2+}$ suggests that the effect is mediated by activating a $Cl^-$ conductance on the basolateral membrane of the NPE cells. The sustained nature of the stimulation is consistent with the time course of the cell shrinkage in response to $A_3$ stimulation.

EXAMPLE 6

Volumetric Measurements and Analysis

The volume of PE cells was measured as the movement of fluid that underlies a change in PE cell volume, this is thought to be the same as the movement of fluid which underlies the reabsorption of aqueous humor (FIG. 1).

After harvesting a single T-75 flask by trypsinization (Yantorno et al., supra.), a 0.5-ml aliquot of the bovine cell suspension in DMEM (or in $Cl^-$-free medium, where appropriate), described in Example 1 was added to 20 ml of each test solution. The standard test solution contained (in mM) 110.0 NaCl, 15.0HEPES [4-(2-hydroxyethyl)-1-piperazineethanesulfonic acid], 2.5 $CaCl_2$, 1.2 $MgCl_2$, 4.7 KCl, 1.2 $KH_2PO_4$, 30.0 $NaHCO_3$, and 10.0 glucose, at a pH of 7.4 and osmolality of 298–305 mOsm. The $Cl^-$ free solution comprised: 110.0 sodium methanesulfonate, 15.0HEPES, 2.5 calcium methanesulfonate, 1.2 $MgSO_4$, 4.7 potassium methanesulfonate, 1.2 $KH_2PO_4$, 30.0 $NaHCO_3$, and 10.0 glucose, at a pH of 7.4 and osmolality of 294–304 mOsm. Parallel aliquots of cells were studied on the same day. One aliquot usually served as a control, and the others were exposed to different experimental conditions at the time of suspension. The same amount of solvent vehicle (dimethylformamide, DMSO or ethanol) was always added to the control and experimental aliquots. The sequence of studying the suspensions was varied to preclude systematic time dependent artifacts (Civan et al., 1994).

Cell volumes of isoosmotic suspensions were measured with a Coulter Counter (model ZBI-Channelyzer II). using a 100-μm aperture (Civan et al., 1992). As previously described (Yantorno et al., supra.), the cell volume ($v_C$) of the suspension was taken as the peak of the distribution function. Cell shrinkage was fit as a function of time (t) to the simple exponential function:

$$v_C = (v_0 - v_\infty) - (e^{-t/\tau}) + v_\infty \qquad (1)$$

where $v_\infty$ is the steady-state cell volume, $v_0$ is cell volume at t=0, and τ is the time constant of of the shrinkage. For purposes of data reduction; the data were normalized to the first time point, taken to be 100% isotonic volume. The baseline isotonic value was 248±203 fl (mean±SE, N=15). Fits were obtained by nonlinear least-squares regression analysis, permitting both $v_\infty$ and τ to be variables (Carré et al., supra., 1997).

Figure 8A:
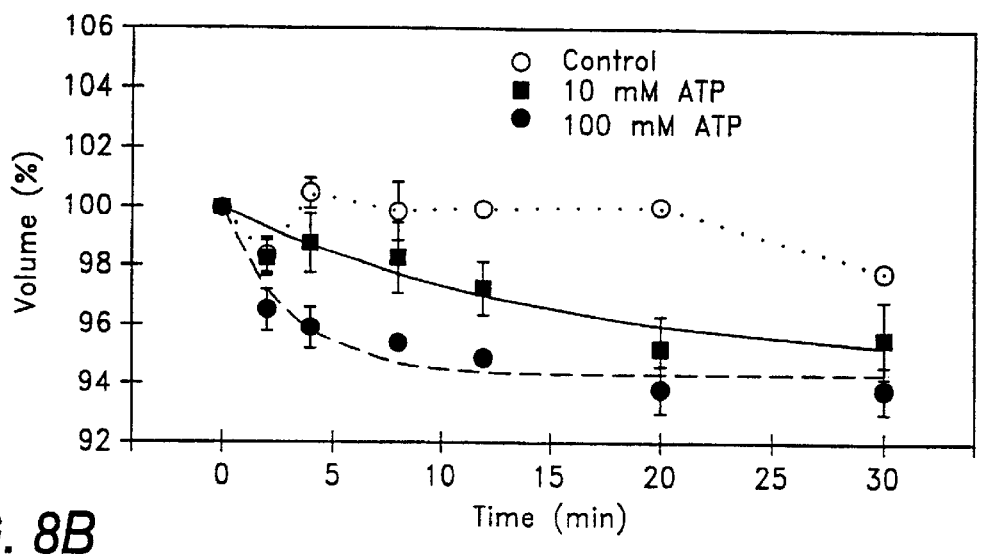
FIGS. 8A–8C show the dependence of PE cell volume on ATP concentration. In all figures, the volumes are normalized to the initial values. The nonlinear least square fits are presented as uninterrupted or interrupted curves, and data points displaying no significant shrinkage are connected by dotted lines.

In approximately 15% of the volumetric studies, ATP produced shrinkage of the PE cells in suspension. As shown in FIG. 8A, the shrinkage was faster and larger after exposure to 100 μM than to 10 μM ATP. In contrast to the results displayed in FIGS. 8A and 9A–C, ATP alone exerted very little effect on cell volume in ~85% of the PE cell-suspensions studied over the concentration range 100 μM–10 mM (FIGS. 10A, 13A, 13C, 14A–C).

Figure 8B:
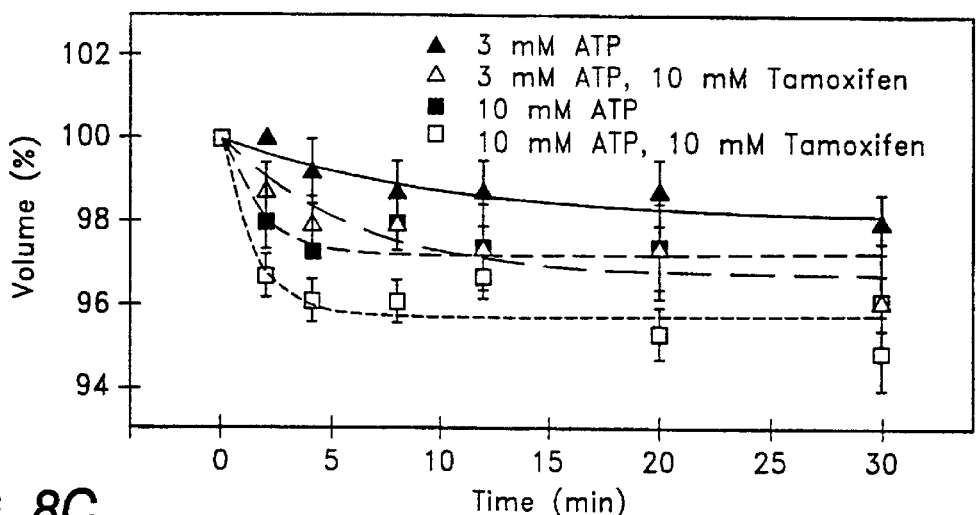

The clinically important, nonsteroidal antiestrogen tamoxifen triggered no consistent response in cell volume over a 30-min period of observation (FIGS. 10A–B). However, in the presence of tamoxifen, the response to ATP was strongly enhanced. The effect was most striking in those preparations which displayed little or no shrinkage when exposed to 100 μM ATP (FIGS. 13A, 13C, 14A–C) or to 10 mM ATP (FIG. 10A). However, the volumetric response to ATP was also enhanced in cell preparations responsive to ATP alone (FIG. 8B). No such interactive response was observed between the corresponding nucleoside adenosine and tamoxifen (FIG. 10B).

Figure 8C:
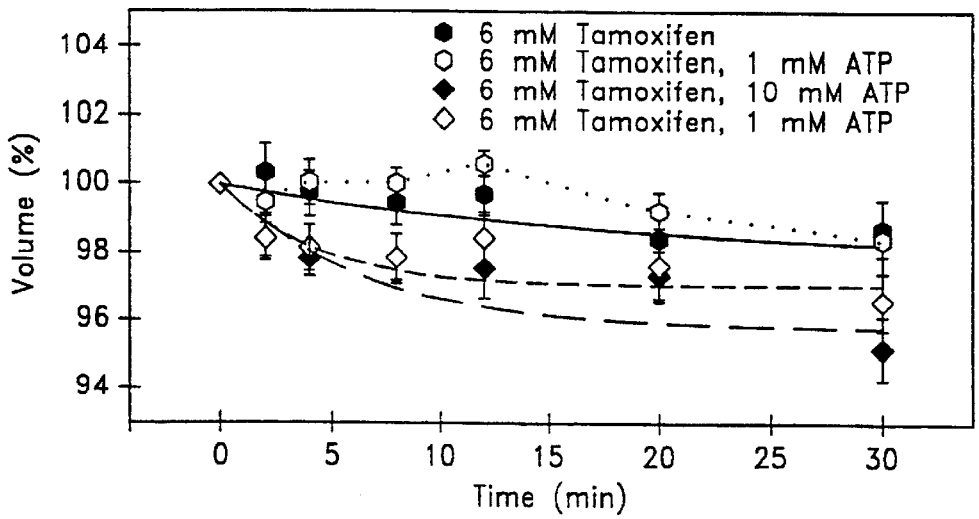

At a constant tamoxifen concentration, ATP triggered detectable shrinkage at 10 μM, but not at 1 μM (FIG. 1C). At 3 μM ATP, the shrinkage was about half that noted with 10 μM ATP (both in the presence of tamoxifen, FIG. 8B). The effects of ATP were comparable at 10 μM and 1 mM (FIG. 8C). A concentration of 100 μM ATP was used in all of the subsequent experiments to ensure that the concentration of ATP was not limiting the rate of shrinkage. The choice of a tamoxifen concentration of 6–10 μM was based on two considerations: 10 μM is the concentration used in probing Cl$^-$ channels in other cells (Wu et al., supra., 1996), and the concentration needed to produce a minimum detectable effect on the response to swelling the current bovine PE cells is >2 μM and ≦6 μM (Mitchell et al., Invest. Ophthalmol. Vis. Sci. 38 (Suppl.):S1042, 1997).

Several observations suggest that the ATP, tamoxifen-activated shrinkage involved Cl$^-$ release. First, the synergism occurred even when gramicidin was present to provide a constant pathway for K$_+$ release (Civan et at., supra., 1994) (FIG. 11A), suggesting that the reduction in volume prompted by ATP and tamoxifen was due to the activation of an anionic conductance. Second, removal of Cl$^-$ from the preincubation and test solutions abolished the synergistic response (FIG. 11A). Third, the Cl$^-$-channel blockers NPPB (100 μM) (Wangemann et al., supra., 1986) and DIDS (500 μM) (Cabantchik et al., Am. J. Physiol., 262: C803–C827, 1992) both inhibited the volume reduction (FIG. 11B).

The synergistic stimulatory effect of tamoxifen in shrinking PE cells was unexpected, given its inhibition of swelling-activated Cl$^-$ channels in many cells (Valverde et al., supra.; Zhang et al., supra.; Nilius et al., supra.), including NPE cells (Wu et al., supra, 1996), and the absence of any effect on swelling-activated Cl$^-$ channels in PE cells (Mitchell et al., supra., 1997). Therefore, we reexamined the effect of tamoxifen on the swelling-activated Cl$^-$ channels of the immortalized human NPE cells we have previously characterized (FIG. 12). After hypotonic swelling, the cell volume spontaneously fell (the regulatory volume decrease, RVD), reflecting the release of KCl$^-$ and secondarily water (Civan, et al., supra., 1994). Addition of tamoxifen 10 min later, after the conclusion of the RVD, did not affect cell volume, but addition 5 min after hypotonic suspension reduced the magnitude of the RVD. Inclusion of tamoxifen at the time of the initial hypotonic suspension completely abolished the RVD, consistent with the earlier report (Wu et al., supra., 1996) that tamoxifen blocks swelling-activated Cl$^-$ channels of NPE cells. Tamoxifen also markedly slowed the rate of hypotonic swelling (FIG. 12), raising the possibility that the antiestrogen also blocks the aquaporin-1 (AQP1) water channels of the NPE cells (Stamer et al., Invest. Ophthalmol. Vis. Sci. 35: 3867–3872, 1994; Lee et al., Current Topics in Membranes 45:105–134, 1998.

The block of RVD in NPE cells by tamoxifen suggested that tamoxifen would reduce efflux of aqueous humor from NPE cells in addition to its action of stimulating reabsorption from PE cells. Thus, tamoxifen could reduce aqueous humor production by two separate mechanisms.

EXAMPLE 7

Ruptured-patch Whole-cell Recording

Harvested cultured PE cells were resuspended and permitted to settle and attach to glass coverslips, which were then transferred to a perfusion chamber (Carré et al., supra., 1997). Solutions were designed to isolate any Cl$^-$ current activated by ATP. Thus both internal and external solutions were devoid of K$^+$, and the cation reversal potential was >95 mV. The perfusate contained (in mM): 105.0 NaCl, 6.0HEPES acid, 4.0HEPES Na$^+$, 1.3 CaCl$_2$, 0.5 MgCl$_2$ and 90.0 mannitol (pH 7.4, 316 mOsm) and the micropipette-filling solution contained (in mM): 40.0HCl, 135.0 NMDG-OH, 95.0 CH$_3$SO$_4$ acid, 2.0 MgATP, 0.05 GTP, 1.1 EGTA and 0.55 CaCl$_2$ (pH 7.2, 275 mOsm). Supplementary experiments were also conducted with freshly-dissected bovine PE cells prepared by the method of Jacob et al. (Am. J. Physiol., 261:C1055–C1062, 1991), as previously described (Carré et al., supra., 1997). Cells were patched while still round, usually one day after dissociation. The perfusate contained (in mM): 105.0 NaCl, 6.0HEPES acid, 4.0HEPES Na$^+$, 1.3 CaCl$_2$, 0.5 MgCl$_2$, 8.0 sucrose and 70.0 mannitol (pH 7.4, 305 mOsm) and the micropipette-filling solution contained (in mM): 105.0 NMDG-Cl, 10.0HEPES acid, 70.0 mannitol, 2.0 MgATP, 0.01 GTP, 1.1 EGTA and 0.55 (CaCl$_2$ (pH 7.2, 286 mOsm). Cells were perfused with Na$_2$ATP dissolved directly into isotonic solution (1.0) or serially diluted (100 μM and 10 μM), while NPPB was diluted 1000:1 from a 100 mM stock in DMSO.

Data were acquired at 1 kHz using Axopatch-1B electronics and associated headstage (Axon Instruments, Foster City, Calif.) and filtered at 500 Hz with a Bessel filter. The micropipettes were double-pulled from Corning No. 7052 glass, coated with Sylgard and fire polished. The membrane potential was held without series-resistance compensation at 0 mV and stepped to voltages over the range from –100 to +100 mV in 20 mV increments for 200 msec periods. The mean current measured between 150–200 msec was used to obtain the patch-clamp data used here. The data presented in FIG. 2 was obtained at –60 mV [the approximate membrane potential (Green et al., Invest. Ophthalmol. Vis. Sci., 26:371–381, 1985)] to facilitate comparison with the volumetric data.

Figure 9A:
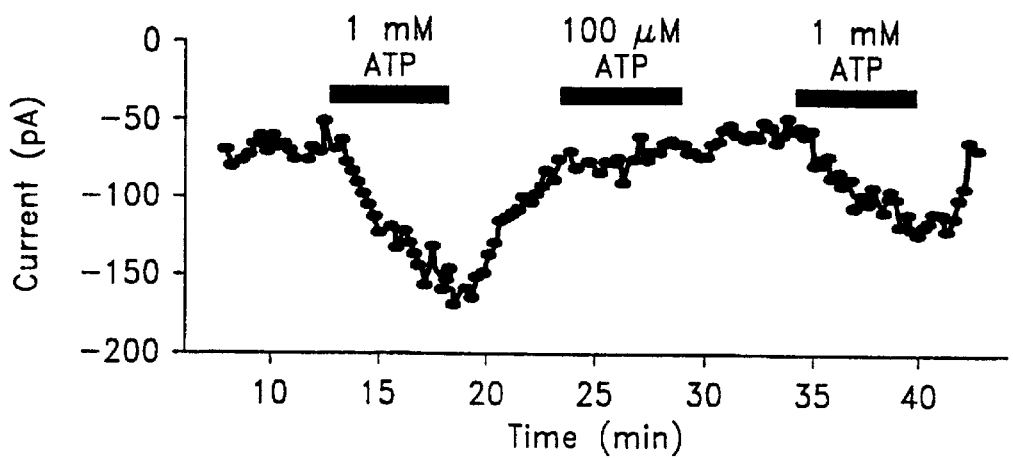
FIGS. 9A–9C show the effects of ATP and NPPB on whole-cell currents of PE cells. The solid bars above show the time period of drug application.
Figure 9B:
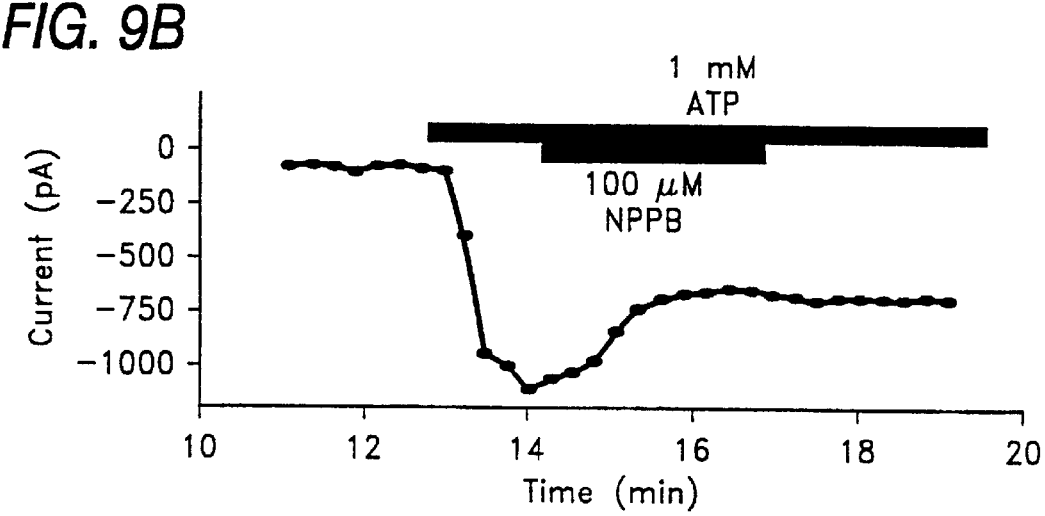
Figure 9C:
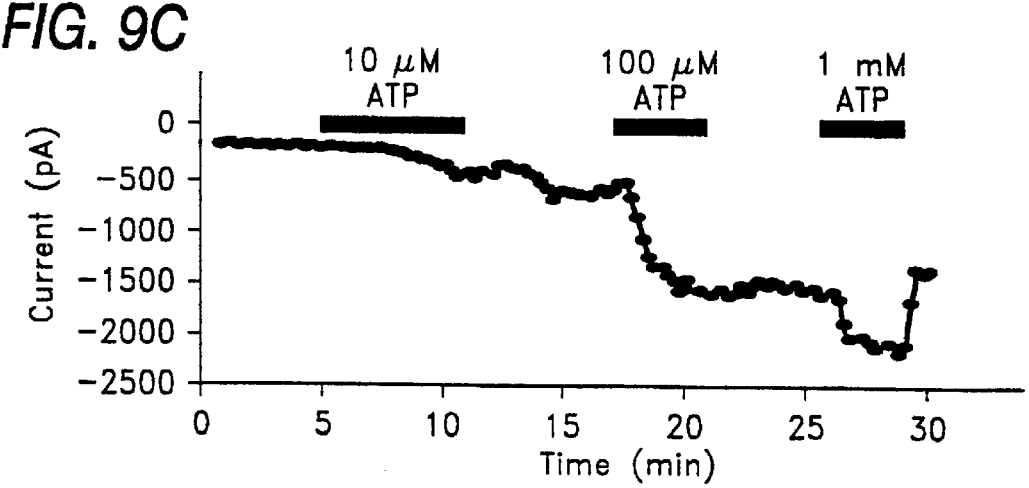

ATP increased the current (FIG. 9A). The activated currents were likely carried by Cl$^-$ as solutions were chosen to minimize cationic currents, and the Cl$^-$-channel blocker NPPB (100 μM) (Wangemann et al., Pflügers Archiv. 407 (Suppl. 2):S128–S141, 1986) reduced the ATP-enhanced currents at –60 mV by 56±11% (FIG. 9B, N=3). The activation of Cl$^-$ channels was not restricted to the PE cell line, for ATP also stimulated currents in fresh bovine PE cells (FIG. 9C) cells. Although current was activated in both fresh and cultured cells, both cell types contained a heterogeneous population with cultured cells responding in 10/17 trials and fresh cells activated in 3/9 trials. Thus, ATP alone can activate Cl$^-$ curents directly, but only in half the cells.

EXAMPLE 8

Measurements of Intracellular Ca$^{2+}$

Bovine PE cells grown on coverslips for 2–4 days were loaded with 5 μM fura-2 μAM for 30–45 min at room temperature, and then rinsed and maintained in fura-free solution before beginning data acquisition. The coverslips were mounted on a Nikon Diaphot microscope and visualized with a x40 oil-immersion fluorescence objective. The emitted fluorescence (510 nm) from 10–12 confluent cells was sampled at 1 Hz following excitation at 340 nm and 380 nm, and the ratio determined with a Delta-Ram system and Felix software (Photon Technology International Inc., Princeton, N.J.). The ratio of light excited at 340 nm to that at 380 nm was converted into Ca$^{2+}$ concentration using the method of Grynkiewicz et al. (*J. Biol. Chem.* 260:3440–3450, 1985). An in situ $K_d$ value for fura-2 of 350 nM was used (Negulescu et al., *Meth. Enzymol.* 192:38–81, 1990). $R_{min}$ was obtained by bathing cells in a $Ca^{2+}$ free isotonic solution of pH 8.0 containing 10 mM EGTA and 5 μM ionomycin. $R^{max}$ was obtained by bathing the cells in isotonic solution with 1.3 mM $Ca^{2+}$ and 5 μM ionomycin. Calibration was performed separately for each experiment. Baseline levels from PE cells in the absence of fura-2 were subtracted from records to control for autofluorescence. Experiments were performed predominantly at room temperature, but several trials were performed at 37° C. using a temperature control unit from Warner Instrument Corp., (Hamden, Conn.). Cells were perfused with an isotonic solution containing (in mM) 105 NaCl, 6HEPES (acid), 4HEPES (Na$^+$), 1.3 CaCl$_2$, 1 MgCl$_2$, 4 KCl, 5 glucose and 90 mannitol, at an osmolarity of 317 mOsm, pH 7.4. Tamoxifen was stored as a 10 mM stock in ethanol for 2 days. In comparing the effects of ATP and of ATP+tamoxifen, 0.1% ethanol was also added to the solutions containing ATP alone.

EXAMPLE 9

Interaction with Histamine and Muscarinic Receptors

In addition to its actions on nuclear estrogen receptors (Klinge et al., supra.) and swelling-activated Cl$^-$ channels (Valverde et al., supra.; Zhang et al., supra.; Nilius et al., supra.; Wu et al., supra.), tamoxifen has been reported to produce multiple other effects. Experiments were conducted in order to address the possibility that one or more of the following known actions of tamoxifen may be involved in ATP, tamoxifen-activated shrinkage: interaction with histamine and muscarinic receptors, antagonism of calcium/calmodulin, inhibition of protein kinase C, and antagonism of plasma- or nuclear membrane estrogen receptors.

The antiestrogens are known to interact with histamine (Brandes et al., supra) and muscarinic receptors (Ben-Baruch, et al., supra) in other preparations. FIG. 13A indicates that 10 μM histamine did not enhance the volumetric response to 100 μM ATP(N=4). The nonmetabolizable muscarinic agonist carbachol did trigger a prompt shrinkage in the presence of 100 μM ATP (FIG. 13A, N=4). However, carbachol triggered approximately the same response whether or not ATP was present, and 10 μM atropine abolished that response (FIG. 13B, N=3). In contrast, tamoxifen had little effect in the absence of ATP (FIGS. 8C, 10A and 10C), and 10 μM atropine did not alter the response to the combined presence of tamoxifen and ATP (FIG. 13C, N-4). FIG. 13 indicates that the volumetric actions of tamoxifen cannot be mediated by either histamine or muscarinic receptors.

However, the results do show that carbachol can act alone to reduce PE cell volume. This suggests that carbachol, or similar agents, can stimulate fluid reabsorption by the PE cells and thus reduce the net production of aqueous humor.

EXAMPLE 10

Antagonism of Calcium/Calmodulin

Tamoxifen can inhibit calcium/calmodulin at the same concentration (10 μM) typically used to block Cl$^-$ channels in NPE cells (Lam, supra.; Wu et al., supra., 1996). In PE cells, trifluoperazine triggered a partial shrinkage of the bovine PE cells in the presence of ATP but this effect was not synergistic as similar effects were observed in the absence of ATP (FIG. 14). This suggests that although calcium/calmodulin can modulate cell volume, it does not mediate the synergistic action of tamoxifen. Thus, inhibitors of calcium/calmodulin can provide a separate additional route by which fluid efflux from the PE cells can be stimulated and the net production of aqueous humor reduced.

EXAMPLE 11

Protein Kinase C Inhibition

Tamoxifen can also inhibit protein kinase C (PKC), with a $K_i$ of 5–100 μM depending on the assay system (O'Brien et al., supra.). However, inhibiting PKC activity with the PKC inhibitor staurosporine produced a small, insignificant shrinkage in the presence of 100 μM ATP, substantially less that that produced by tamoxifen (FIG. 15). Activating PKC with DiC$_8$ in the presence of 100 μM ATP also had no significant effect on cells volume. Thus, the synergistic effect of tamoxifen cannot be mediated by its inhibition of baseline PKC activity.

EXAMPLE 12

Antagonism of Estrogen Receptors

In the presence of 100 μnM 17β-estradiol, the response to the combined application of ATP and tamoxifen was reduced, consistent with the known antiestrogen action of tamoxifen (FIG. 16A, N=4, P<0.05, F-distribution). The 17β-estradiol also reduced the synergistic shrinkage produced by ATP and tamoxifen in another series of four experiments (P<0.01, F-distribution, data not shown), whereas the inactive estrogenic isomer 17α-estradiol had no significant effect (P>0.05, F-distribution). In the absence of tamoxifen, the 17α- and 17β-estradiols exerted very small effects on cell volume (FIG. 16B, N=4). The data are consistent with the possibility that tamoxifen and estrogen compete for occupancy of the same population of receptors.

EXAMPLE 13

Potential Role of $Ca^{2+}$

Non-pigmented ciliary epithelial cells show a synergistic elevation in free intracellular $Ca^{2+}$concentration ($Ca^{2+}_i$) upon simultaneous presentation of certain drug pairs, and this synergism may involve the activation of the $G_i$ G-protein (Farahbakhsh et al., Exp. eye Res. 64:173–179, 1997). As ATP can activate $G_i$ in a variety of tissues (Murthy et al., *J. Biol. Chem.* 273:4695–4704, 1998), it was determined whether the signaling cascade for the synergistic shrinkage produced by tamoxifen and ATP could reflect a synergistic change in $Ca^{2+}_i$. Tamoxifen (10 μM) itself triggered no significant change (Δ) in $Ca^{2+}_i$ (Δ=7±6nM, N=4). Although $Ca^{2+}_i$ increased in response to both ATP a ATP+TMX, the comparison of the response was complicated by the attenuation of the $Ca^{2+}$ spike with repeated exposure, and the variation between preparations. A 3-min application of either 100 μM ATP or 100 μM ATP+10 μM TMX usually produced an elevation in $Ca^{2+}$, but it was difficult to elicit a response of similar magnitude to a second application 5 min later. Elevating the temperature to 37° C. did not eliminate the attenuation.

Nevertheless, it did prove possible to compare the magnitudes of successive $Ca^{2+}$ responses when each drug application was limited to periods of 20 sec (FIG. 17). Experiments were performed by alternating 20-sec exposures to 100 μM ATP+10 μM TMX with 20sec exposures to 100 μμM ATP alone (including 0.1% ethanol as a vehicle control for the TMX). Cells were washed in isotonic solution for 5 min between drug applications, and 4–5 applications were possible per trial (FIG. 17A). The order of drug application shown in FIG. 10A, beginning first with 100 μM ATP+10 μM TMX, is termed the T series. A parallel set of experiments termed the A series was performed which began with the application of ATP alone followed 5 min later by ATP+TMX.

To check for synergism while compensating for the attenuation, the responses to each application were compared for those experiments where ATP was first added (A series) with where ATP+TMX was first added (T series). Comparing the responses to successive applications of drugs, it is clear that there was no significant difference between the two series, whether ATP alone or ATP+TMX was added at a given point in time (FIG. 17B). The presence of TMX did not affect the size of the $Ca^{2+}$ response to ATP regardless of whether it was included in the first, second, third or fourth application ($P>0.05$ for applications 1–4, $N=3-4$). We conclude that ATP and tamoxifen di produce a synergistic elevation in the level of intracellular $Ca^{2+}$.

EXAMPLE 14

In Vivo Animal Model

A rabbit model is used to determine the ability of $A_3$ subtype adenosine receptor antagonists, antiestrogens and calmodulin antagonists to reduce intraocular pressure. Ten normal New Zealand White rabbits are used for the study, sedated, and their intraocular pressure is measured by standard optometric methods for several days at various times of the day to account for normal pressure variations. Once the average baseline pressure of each obtained, five rabbits are assigned to one of two groups. In the first group, one eye is administered vehicle (e.g., corn oil or dimethyl sulfoxide (DMSO)) in the form of liquid drops and the other eye is left as an untreated control. In the second group, one eye is administered vehicle plus test compound in the form of liquid drops, and the other eye is left as an untreated control. The test compound is administered at a concentration ranging from about 1 nM to 100 mM to see a dose response relationship of intraocular pressure reduction. Intraocular pressure is then measured several hours after the administration to determine reduction of intraocular pressure by the test compound.

EXAMPLE 15

Synthesis of MRS-1649 and Related $A_3$ Receptor Antagonists

Materials. Iodomethane was purchased from Fluka (Buchs, Switzerland). Iodoethane and 1-iodopropane were purchased from Aldrich (Milwaukee, Wis.). PBS (1xpH 7.4) was purchased from Biofluids, Inc. (Rockville, Md.). Starting 3,5-diacyl-2,4-dialkylpyridine and dihydropyridine derivatives were described previously (Li et al., *J. Mod. Chem.* 41:3186–3201, 1998; Li et al., *J. Med. Chem.* 42:706–721, 1999). All other materials were obtained from commercial sources.

Proton nuclear magnetic resonance spectroscopy was performed on a Varian GEMINI-300 spectrometer, and all spectra were obtained in $CDCl_3$. Chemical shifts (δ) relative to tetramethylsilane are given. Chemical-ionization (CI) mass spectrometry was performed with a Finnigan 4600 mass spectrometer, and electron-impact (EI) mass spectrometry with a VG7070F mass spectrometer at 6 kV. Elemental analysis was performed by Galbraith Laboratories, Inc. (Knoxville, Tenn.) and/or Atlantic Microlab, Inc. (Norcross, Ga.).

General Procedure for Preparation of Pyridinium Salt (10, 11, 14–23) by Quaternary Amination of 3,5-Diacyl-2,4-Dialkylpyridine Derivatives with Iodomethane: A mixture of a 3,5-diacyl-2,4-dialkylpyridine derivative (14 mg, 0.038 mmol) and iodomethane (59 mg, 0.38 mmol) in 2 mL of anhydrous nitromethane was sealed in a Pyrex tube and was heated at 80° C. for 2 days. After the mixture cooled to room temperature, the solvent and excess MeI were removed under reduced pressure to leave a yellow oil. It was applied to TLC separation [ethyl acetate: petroleum ether=1:4)v/v) for the first development; methanol: chloroform=1:5 (v/v) for a second development and ethyl acetate: petroleum ether=1:1 (v/v) for a third development] and 9.5 mg of the desired product (Pyridinium Salt, such as MRS 1649, 11) was afforded as a yellow solid (yield: 49%). If methanol or acetone was used as the solvent, the yield was much lower than with nitromethane.

HPLC results showed that 11 is free of the starting 2 (2,4-diethyl-3-(ethylsulfanylcarbonyl)-5-ethyloxy-carbonyl-6-phenylpyridine). The mobile phase used for the analysis consisted of methanol, acetonitrile and water (45:45:10). At a flow rate of 1.0 mL/min with a 4.6×250 mm (internal diameter) reverse-phase 300 Å C-18 column operated at ambient temperature, 11 had a retention time of 2.3 min (purity >99%). CHN analysis of 11: Calcd for $C_{22}H_{28}INO_3S$ C: 51.47%, H: 5.50%, N: 2.73%. Found: C: 51.42%, H: 5.14%, N: 2.43%. HR-MS (FAB, m-b): Calcd for $C_{22}H_{28}NO_3S$ ($M^+$-I): 386.1790. Found: 386.1776. UV spectra was measured using a Beckman DU 640 Spectrophotometer. In methanol at ambient temperature, 11 had a $\lambda_{max}=203$ nm, $\epsilon_{max}=6.65\times10^4$ lmol$^{-1}$cm$^{-1}$; $\lambda_{max}=224$ nm, $\epsilon_{max}=3.30\times10^4$ lmol$^{-1}$cm$^{-1}$; $\lambda_{max}=288$ nm, $\epsilon_{max}=9.62\times10^3$ lmol$^{-1}$cm$^{-1}$.

The water solubility of 11 was measured by the following method. 100 μL of de-ionized water was saturated with 5 mg 11 with heating. After cooling to room temperature and the disappearance of turbidity, 50 μL of the clear supernatant was withdrawn and lyophilized to give 1.1 mg of 11. The water solubility of 11 was calculated to be 42.8 mM at room temperature.

1-Methyl-2-methyl-4-ethyl-3-(ethylsulfanylcarbonyl)-5-ethyloxycarbonyl-6-phenylpyridinium Iodide (10)

$^1$H-NMR δ: 0.88 (t, J=6.9 Hz, 3H), 1.26 (t, J=7.5 Hz, 3H), 1.33 (t, J=7.5 Hz, 3H), 2.69 (s, 3H), 2.79 (q, J=7.5 Hz, 2H), 3.24 (q, J=7.5 Hz, 2H), 4.01 (q, J=6.9 Hz, 2H), 4.17 (s, 3H), 7.49–7.53 (m, 3H), 7.65–7.68 (m, 2H). MS (CI/NH$_3$): m/z 500 (MH$^+$), 358 (MH$^+$-Me-I), 297 (MH$^+$-Me-I-SEt). $K_i$(hA$_3$)=379 nM.

1-Methyl-2,4-Diethyl-3-(ethylsulfanylcarbonyl)-5-ethyloxycarbonyl-6-phenylpyridinium Iodide (MRS 1649, 11)

$^1$H-NMR δ: 0.86 (t, J=7.2 Hz, 3H), 1.32 (t, J=7.8 Hz, 3H), 1.41 (t, J=7.8 Hz, 3H), 1.44 (t, J=7.8 Hz, 3H), 2.84 (q, J=7.8 Hz, 2H), 3.22 (q, J=7.8 Hz, 2H), 3.44 (q, J=7.8 Hz, 2H), 3.98 (q, J=7.2 Hz, 2H), 4.22 (s, 3H), 7.56–7.62 (m, 3H), 7.72–7.75 (m, 2H). MS (CI): m/z 514 (MH$^+$), 372 (MH$^+$-Me-I). $K_i$(hA$_3$)=219 nM.

1-Methyl-2,4-diethyl-3-ethylsulfanylcarbonyl)-5-(2-fluoroethyloxycarbonyl)-6-phenyl pyridinium Iodide (14)

$^1$H-NMR δ: 1.20 (t, J=7.5 Hz, 3H), 1.39 (t, J=7.5 Hz, 3H), 1.46 (t, J=7.5 Hz, 3H), 2.79 (q, J=7.5 Hz, 2H), 2.99 (q, J=7.5

Hz, 2H), 3.27 (q, J=7.5 Hz, 2H), 4.20 (s, 3H), 4.28 (m, 2H), 4.30–4.40 (m, 2H), 7.47–7.50 (m, 3H), 7.64–7.67 (m, 2H). MS (CI/NH$_3$): m/z 390 (MH$^+$-Me-I). K$_i$(hA$_3$)=364 nM.

1-Methyl-2-ethyl-4-ethyl-3-(ethylsulfanylcarbonyl)-5-propyloxycarbonyl-6-phenylpyridinium Iodide (15)

$^1$H-NMR δ: 0.68 (t, J=7.8 Hz, 3H), 1.25 (t, J=7.8 Hz, 3H), 1.39 (m, 2H), 1.49 (t, J=7.8 Hz, 3H), 1.57 (t, J=7.8 Hz, 3H), 2.97 (q, J=7.8 Hz, 2H), 3.28 (q, J=7.8 Hz, 2H), 3.38 (q, J=7.8 Hz, 2H), 4.07 (t, J=6.9 Hz, 2H), 4.21 (s, 3H), 7.69–7.76 (m, 5H). MS (CI/NH$_3$): m/z 386 (MH$^+$-Me-I). K$_i$(hA$_3$)=483 nM.

1-Methyl-2-ethyl-4-propyl-3-(ethylsulfanylcarbonyl)-5-propyloxycarbonyl-6-phenylpyridinium Iodide (16)

$^1$H-NMR δ: 0.67 (t, J=7.8 Hz, 3H), 1.04 (t, J=7.8 Hz, 3H), 1.40 (m, 2H), 1.48 (t, J=7.8 Hz, 3H), 1.55 (t, J=7.8 Hz, 3H), 1.74 (m, 2H), 2.87 (t, J=7.8 Hz, 2H), 3.27 (q, J=7.8 Hz, 2H), 3.42 (q, J=7.8 Hz, 2H), 4.05 (t, J=7.8 Hz, 2H), 4.20 (s, 3H), 7.62–7.74 (m, 5H). MS (CI/NH$_3$): m/z 558 (M$^+$+NH$_4$), 525 (M$^+$-I-Me), 414 (M$^+$-I), 369 (M$^+$-1-I-Me-Et). K$_i$(hA$_3$)=2.02 μM.

1-Methyl-2-ethyl-4-propyl-3-(3-fluoropropylsulfanylcarbonyl)-5-propyloxycarbonyl-6-phenylpyridinium Iodide (17)

$^1$H-NMR δ: 0.68 (t, J=7.8 Hz, 3H), 1.04 (t, J=7.8 Hz, 3H), 1.41 (m, 2H), 1.55 (t, J=7.8 Hz, 3H), 1.73 (m, 2H), 2.16 (m, 2H), 2.88 (m, 2H), 3.35 (q, J=7.8 Hz, 2H), 3.41 (t, J=6.9 Hz, 2H), 4.06 (t, J=6.9 Hz, 2H), 4.22 (s, 3H), 4.55 (t, J=6.0 Hz, 1H), 4.71 (t, J=6.0 Hz, 1H), 7.68–7.75 (m, 5H). MS (CI/NH$_3$): m/z 432 (MH$^+$-Me-I). K$_i$(hA$_3$)=465 nM.

1-Methyl-2-ethyl-4-(2-acetylthioethyl)-3-(ethylsulfanylcarbonyl)-5-propyloxycarbonyl-6-phenylpyridinium Iodide (18)

$^1$H-NMR δ: 0.66 (t, J=7.5 Hz, 3H), 1.37 (m, 2H), 1.39 (t, J=7.8 Hz, 3H), 1.45 (t, J=7.2 Hz, 3H), 2.35 (s, 3H), 2.89–3.02 (m, 4H), 3.11 (m, 2H), 3.28 (q, J=7.2 Hz, 2H), 4.00 (t, J=6.9 Hz, 2H), 4.23 (s, 3H), 7.53.7.55 (m, 3H), 7.67–7.70 (m, 2H). MS (CI/NH$_3$): m/z 460 (MH$^+$-Me-I). K$_i$(hA$_3$)=538 nM.

1-Methyl-2-ethyl-4-(2-phthalimidoethyl-3-(ethylsulfanylcarbonyl)-5-ethyloxycarbonyl-6-phenylpyridinium Iodide (19)

$^1$H-NMR δ: 0.94 (t, J=6.9 Hz, 3H), 1.34 (t, J=7.2 Hz, 3H), 1.48 (t, J=7.2 Hz, 3H) 2.94 (q, J=6.9 Hz, 2H), 3.15 (t, J=7.8 Hz, 2H), 3.24 (q, J=7.2 Hz, 2H), 4.01 (t, J=7.8 Hz, 2H), 4.21 (s, 3H), 4.25 (q, J=7.2 Hz, 2H), 7.51 (m, 3H), 7.65 (m, 2H), 7.78 (m, 2H), 7.89 (m, 2H). MS (CI/NH$_3$): m/z 517 (MH$^+$-Me-I). K$_i$(hA$_3$)=1.25 μM.

1-Methyl-2-butyl-4-ethyl-3-(ethylsulfanylcarbonyl)-5-ethyloxycarbonyl-6-phenylpyridinium Iodide (20)

$^1$H-NMR δ: 0.90 (t, J=7.5 Hz, 3H), 1.04 (t, J=7.5 Hz, 3H), 1.29 (t, J=7.5 Hz, 3H), 1.34–1.43 (m, 2H), 1.46 (t, J=7.5 Hz, 3H), 1.84 (m, 2H), 2.76 (q, J=7.5 Hz, 2H), 2.88 (t, J=7.5 Hz, 2H), 3.16 (q, J=7.5 Hz, 2H), 4.05 (q, J=7.5 Hz, 2H), 4.26 (s, 3H), 7.52–7.55 (m, 3H), 7.69–7.72 (m, 2H), MS (CI/NH$_3$): m/z 400 (MH$^+$-Me-I). K$_i$(hA$_3$)=436 nM.

1-Methyl-2-cyclobutyl-4-ethyl-3-(ethylsulfanylcarbonyl)-5-ethyloxycarbonyl-6-phenyl pyridinium Iodide (21)

$^1$H-NMR δ: 0.99 (t, J=7.5 Hz, 3H), 1.29 (t, J=7.5 Hz, 3H), 1.45 (t, J=7.5 Hz, 3H), 1.88–1.97 (m, 1H), 1.97–2.07 (m, 1H), 2.18–2.32 (m, 2H), 2.53–2.65 (m, 2H), 2.71 (q, J=7.5 Hz, 2H), 3.13 (q, J=7.5 Hz, 2H), 3.81 (m, 1H), 4.01 (q, J=7.5 Hz, 2H), 4.23 (s, 3H), 7.54–7.56 (m, 3H), 7.73–7.75 (m, 2H), MS (CI/NH3): m/z 398 (MH$^+$-Me-I). K$_i$(hA$_3$)=1.41 μM.

1-Methyl-2-(2-benzyloxylethyl)-4-propyl-3-(ethylsulfanylcarbonyl)-5-propyloxycarbonyl-6-phenylpyridinium Iodide (22)

$^1$H-NMR δ: 0.69 (t, J=7.2 Hz, 3H), 1.02 (t, J=7.2 Hz, 3H), 1.44 (t, J=7.2 Hz, 3H), 1.45 (m, 2H), 1.68 (m, 2H), 2.71 (m, 2H), 3.17 (q, J=7.2 Hz, 2H), 3.24 (t, J=7.2 Hz, 2H), 3.99 (t, J=7.2 Hz, 2H), 4.02 (q, J=7.2 Hz, 2H), 4.25 (s, 3H), 4.58 (s, 2H), 7.29–7.35 (m, 5H), 7.53–7.56 (m, 3H), 7.68–7.71 (m, 2H). MS (CI/NH$_3$): m/z 648 (MH$^+$), 506 (MH$^+$-Me-I), 445 (MH$^+$-Me-I-SEt). K$_i$(hA$_3$)=348 nM.

1-Methyl-2,4-diethyl-3-(ethylsulfanylcarbonyl)-5-ethyloxycarbonyl-6-cyclopentylpyridinium Iodide (23)

$^1$H-NMR δ: 1.10 (t, J=7.5 Hz, 3H), 1.32 (t, J=7.5 Hz, 3H), 1.41 (t, J=7.5 Hz, 3H), 1.44 (t, J=7.5 Hz, 3H), 1.66 (m, 2H), 1.95 (m, 7H), 2.62 (q, J=7.5 Hz, 2H), 2.81 (q, J=7.5 Hz, 2H), 3.97 (q, J=7.5 Hz, 2H), 4.28 (s, 3H), 4.40 (q, J=7.5 Hz, 2H). MS (CI/NH$_3$): m/z 364 (MH$^+$-Me-I). K$_i$(hA$_3$)=695 nM.

1-Ethyl-2,4-diethyl-3-(ethylsufanylcarbonyl)-5-ethyloxycarbonyl-6-phenylpyridinium Iodide (12)

$^1$H-NMR δ: 0.89 (t, J=7.5 Hz, 3H), 1.28 (t, J=7.5 Hz, 3H), 1.39 (t, J=7.5 Hz, 3H), 1.44 (t, J=7.2 Hz, 3H), 2.79 (q, J=7.5 Hz, 2H), 2.94 (t, J=7.5 Hz, 2H), 3.11 (q, J=7.5 Hz, 2H), 3.34 (q, J=7.5 Hz, 2H), 4.02 (q, J=7.2 Hz, 2H), 5.20 (q, J=7.5 Hz, 2H), 7.52–7.58 (m, 3H), 7.68–7.71 (m, 2H). MS (CI/NH$_3$): m/z 372 (MH$^+$-Et-I). K$_i$(hA$_3$)=577 nM.

1-Propyl-2,4-diethyl-3-(ethylsulfanylcarbonyl)-5-ethyloxycarbonyl-6-phenylpyridinium Iodide (13)

$^1$H-NMR δ: 0.91 (m, J=7.2 Hz, 6H), 1.29 (t, J=7.5 Hz, 3H), 1.39 (t, J=7.5 Hz, 3H), 1.43 (t, J=7.2 Hz, 3H), 2.44 (t, J=7.2 Hz, 2H), 2.79 (q, J=7.2 Hz, 2H), 3.07 (q, J=7.5 Hz, 2H), 3.38 (q, J=7.2 Hz, 2H), 4.01 (q, J=7.2 Hz, 2H), 4.29 (q, J=7.2 Hz, 2H), 5.22 (q, J=7.2 Hz, 2H), 7.51–7.54 (m, 3H), 7.68–7.71 (m, 2H), MS (CI/NH$_3$): m/z 372 (MH$^+$-Pr-I). K$_i$(hA$_3$)=1.35 μM.

General Procedure for Preparation of 1-Methyl Dihydropyridines (24 and 25) by Alkylation of 3,5-Diacyl-2,4-Dialkyl-1,4-Dihydropyridine Derivatives with Iodomethane (Scheme 1): A solution of the appropriate DHP (2,4-diethyl-3-(ethylsulfanylcarbonyl)-5-ethyloxycarbonyl-6-phenyl-1,4-dihydropyridine, 15 mg, 0.04 mmol) in 2 mL of anhydrous THF was treated with NaH (60%, 2 mg, 0.08 mmol) at room temperature under stirring for 5 min. Then iodomethane (28 mg, 0.2 mmol) was added, and the reaction mixture was stirred for another 10 min (monitor by TLC). At completion the reaction mixture was applied to TLC separation (ethyl acetate: petroleum ether=1: 19 v/v), and 11 mg of 24 was obtained (yield: 71%).

1-Methyl-2,4-diethyl-3-(ethylsulfanylcarbonyl)5-ethyloxycarbonyl-6-phenyl-1,4-dihydropyridine (24)

$^1$H-NMR δ: 0.85 (t, J=7.2 Hz, 3H), 0.93 (t, J=7.2 Hz, 3H), 1.20 (t, J=7.2 Hz, 3H), 1.29 (t, J=7.2 Hz, 3H), 2.74 (q, J=7.2 Hz, 2H), 2.85 (s, 3H), 2.92 (q, J=7.2 Hz, 2H), 3.07 (q, J=7.2 Hz, 2H), 3.87 (q, J=7.2 Hz, 2H), 4.02 (t, J=7.2 Hz, 1H), 7.20 (m, 2H), 7.38–7.41 (m, 3H). MS (CI/NH$_3$): m/z 388 (MH$^+$).

1-Methyl-2,4-diethyl-3-(ethylsulfanylcarbonyl)-5-ethyloxycarbonyl-6-cyclopentyl-1,4-dihydropyridine (25)

$^1$H-NMR δ: 0.78 (t, J=7.8 Hz, 3H), 1.11 (t, J=7.8 Hz, 3H), 1.28 (t, J=7.8 Hz, 3H), 1.32 (t, J=7.8 Hz, 3H), 1.46 (m, 2H), 1.60–1.78 (m, 7H), 2.10 (m, 2H), 2.60–2.67 (m, 1H), 2.89 (q, J=7.8 Hz, 2H), 3.01–3.13 (m, 1H), 3.15 (s, 3H), 4.10 (t, J=6.0 Hz, 1H), 4.13–4.26 (m, 2H). MS (CI/NH$_3$): m/z 380 (MH$^+$), 318 (M$^+$-SEt, base).

Chemical Transformation of 24 to 11 through Oxidation with Iodine (Scheme 1): A solution of 24 (5 mg, 0.013 mmol) in 0.5 mL of dry nitromethane was treated with iodine (10 mg, 0.040 mmol) at room temperature with stirring for 1 day (monitor by TLC). At completion the reaction mixture was applied to TLC separation (ethyl acetate:petroleum ether=1:4 v/v for the first development then 1:1 for a second development), and 2 mg of a yellow solid was obtained (yield: 30%), with $^1$H-NMR and MS data consistent with those of compound 11.

Oxidation of a 1-Methyl-1,4-Dihydropyridine Derivative in the Presence of Rat Brain Homogenate (Bodor et al., *J. Med. Chem.* 26:528–534, 1983; Wu et al., *J. Med. Chem.* 32:1782:1788, 1989).

The rat brain homogenate was prepared by the following method. One rat (1 kg) was killed and the brain (weighing 2.26 g) was removed, and homogenized in 12 mL PBS (Biofluids, Inc., 1×pH 7.4). The homogenate was centrifuged at 12,000×rpm, and the supernatant was used. 5 mg of 24 dissolved in 0.2 mL of DMSO was mixed with 10 mL of brain homogenate (initial concentration of 1.27 mM), which was previously equilibrated to 37° C. in a water bath incubator, and shaking was continued at that temperature. Aliquots of 500 μL were withdrawn at 2, 4, 8, 16, 32, 64, 128, 256, 768 min (2×each) from the test medium, added immediately to 3 mL of ice-cold ethyl ether, shaken vigorously, and placed in a freezer. When all samples had been collected, and the ether layer of each sample was separated. After evaporation of the ether, each residue was dissolved in 200 μL methanol, filtered through Whatman 1 filter paper and analyzed by HPLC.

Pyridinium salt 11 could be generated through oxidation of the corresponding reduced precursor, 1-methyl-2,4-diethyl-3-(ethylsulfanylcarbonyl)-5-ethyloxycarbonyl-6-phenyl-1,4-dihydropyridine, 24. The conversion of 24 to 11 by chemical means (iodine in nitromethane) and during incubation at 37 C with rat brain membranes, to simulate in vivo conditions, was studied. The chemical conversion occurred readily, and the time course of the biochemical oxidation was recorded. At regular time points, aliquots were removed from the incubation mixture, extracted with ether, and both the precursor and the pyridinium salt were assayed in the evaporated organic phase using HPLC. The oxidation occurred cleanly with a t$_{1/2}$ of approximately 47 min.

The 1-methyl dihydropyridine 24 (precursor of MRS 1649) was found to bind selectively to human A$_3$ adenosine receptors. At human A$_3$ receptors, the K$_i$ value was 379±122 nM (n =4). The K$_i$ value at rat A$_1$ receptors was 28.4±2.5 μM (n=3). At rat A$_{2A}$ receptors, the percent displacement of specific radioligand binding was 48±7% at 100 μM. Therefore to demonstrate the prodrug principle, ie. an inactive prodrug that could be converted to a selective adenosine antagonist, the corresponding 6-cyclopentyl dihydropyridine 25 was prepared. The 6-cyclopentyl analogue, 1-methyl-2,4-diethyl-3-(ethylsulfanylcarbonyl)-5-ethyloxycarbonyl-6-cyclopentyl-1,4-dihydro pyridine (25), was shown to increase affinity at human A$_3$ receptors upon oxidation to the corresponding pyridinium salt (23). Compound 25 had a K$_i$ value at human A$_3$ receptors of 6.40±0.78 μM, while 23 was an order of magnitude more potent (K$_i$ of 695 nM), suggesting a prodrug scheme. At rat A$_1$ receptors, both the precursor, compound 25 (34 ±1% displacement at 100 μM) and the oxidized product, 23 (K$_i$ value 11.5 μM) bound only weakly.

Thus, in the present study, one reduced precursor, 25, was found to be clearly less potent than the corresponding pyridinium salt, 23, in binding to adenosine receptors, especially the A$_3$ subtype, and another precursor, 24, was found to have the identical human A$_3$ receptor affinity before and after oxidation. Thus, depending on the structure of the pyridine substitutents, one can determine the degree to which the antagonist requires pre-activation of a prodrug form in order to acheive antagonism of A$_3$ receptors.

EXAMPLE 16

Pharmacology

Adenylate cyclase assay. Adenylate cyclase assays were performed with membranes prepared from Chinese hamster ovary (CHO) cells stably expressing either the human A$_1$ receptor or human A$_3$ receptor by the method of Salomon et al., (*Anal. Biochem.* 58:541–548, 1974) as described previously with the following modifications (Jacobson et al., *Neuropharmacol.*, 36:1157–1165, 1997). 4-(3-Butoxy-4-methoxybenzyl)-2-imidazolidinone (Ro 20–1724, 20 μM, Calbiochem, San Diego, Calif.) was employed to inhibit phosphodiesterases rather than papaverine, and the NaCl concentration in the assay was 25 mM. Membranes were pretreated with 2 units/mL adenosine deaminase, and the antagonist 11 (10 μM) at 30 C for 5 min prior to initiation of the adenylate cyclase assay. Adenylate cyclase was stimulated with forskolin (1 μM). Concentration response data for the inhibition of adenylate cyclase activity by IB-MECA (human A$_3$ receptor) were obtained. Maximal inhibition of adenylate cyclase by IB-MECA at the human A$_3$ receptor correlated to ~60% of total stimulation, respectively. IC$_{50}$ values were calculated using InPlot (GraphPad, San Diego, Calif.). K$_B$ values were calculated as described. (Alunlakshana et al., *Brit. J. Pharmacol. Chemother.* 14:48, 1959).

Responses for agonist alone (0) or in combination with the A$_3$ adenosine antagonist 11 (10 μM) were measured. IC$_{50}$ values were 41.4±14.9 nM (IB-MECA alone), 1.08±0.19 μM (+11). Compound 11 effectively antagonized the effects of an agonist in a functional A$_3$ receptor assay, ie. inhibition of adenylate cyclase in CHO cells expressing cloned human A$_3$ receptors. [814] In this functional assay, IB-MECA inhibited adenylate cyclase via human A$_3$ receptors with an IC$_{50}$ of 41.4±14.9 nM In=3). In the presence of 10 μM of 11, the concentration response curve was shifted 26-fold to the right, with an IC$_{50}$ of 1.08±0.19 μM (n=3). From a Schild analysis (Alunlakshana et al., supra.), a K$_B$ value obtained for antagonism by 11 was 399 nM, i.e. approximately 1.8-times the K$_i$ value obtained in binding to human A$_3$ receptors.

Radioligand binding studies. Binding of [$^3$H]R-N$^6$-phenylisopropyladenosine ([$^3$H]R-PIA) to A$_1$ receptors from rat cerebral cortex membranes and of [$^3$H]-2-[4-[(2-carboxyethyl)phenyl]ethylamino]-5'-N-ethylcarbamoyladenosine ([$^3$H]CGS 21680) to A$_{2A}$ receptors from rat striatal membranes was performed as described previously (Schwabe et al., *Naunyn Schmiedeberg Arch.*

Pharmacol. 313:179–187, 1980; Jarvis et al., *J. Pharmacol. Exp. Ther.* 251:888–893, 1989) Adenosine deaminase (3 units/mL) was present during the preparation of the brain membranes, in a pre-incubation of 30 min at 30° C., and during the incubation with the radioligands. Nonspecific binding was determined in the presence of 10 $\mu$M ($A_1$ receptors) or 20 $\mu$M ($A_{2A}$ receptors)2-chloroadenosine.

Binding of [$^{125}$I] $N^6$-(-4-amino-3-iodobenzyl)-5'-N-methylcarbamoyladenosine ([$^{125}$I]AB-MECA)$^{24}$ to membranes prepared from human embryonic kidney (HEK-293) cells stably expressing the human $A_3$ receptor (Salvatore, et al., *Proc. Natl. Acad. Sci. U.S.A.* 90:10365–10369, 1993), close HS-21a (Receptor Biology, Inc., Beltsville, Md.) or to membranes prepared from Chinese hamster ovary (CHO) cells stably expressing the rat $A_3$ receptor (Zhou, et al., *Proc. Natl. Acad. Sci. U.S.A.* 89:7432–7436, 1992) was performed as described at 4° C. (Olah et al., *Mol. Pharmacol.* 45:978–982, 1994). The assay medium consisted of a buffer containing 10 mM $Mg^{2+}$, 50 mM Tris, 3 units/mL adenosine deaminase, and 1 mM EDTA, at pH 8.0 (4° C.). The glass incubation tubes contained 100 $\mu$L of the membrane suspension (0.3 mg protein/mL, stored at −80° C. in the same buffer), 50 $\mu$L of [$^{125}$I] AB-MECA (final concentration 0.3 nM), and 50 $\mu$L of a solution of the proposed antagonist. Nonspecific binding was determined in the presence of 100 $\mu$M $N^6$-phenylisopropyladenosine (NECA).

All non-radioactive compounds were initially dissolved in DMSO, and diluted with buffer to the final concentration, where the amount of DMSO never exceeded 1%. Incubations were terminated by rapid filtration over Whatman GF/B filters, using a Brandell cell harvester (Brandell, Gaithersburg, MD). The tubes were rinsed three times with 3 mL buffer each.

At least five different concentrations of competitor, spanning 3 orders of magnitude adjusted appropriately for the $IC_{50}$ of each compound, were used. $IC_{50}$ values, calculated with the nonlinear regression method implemented in the InPlot program (Graph-PAD, San Diego, Calif.), were converted to apparent $K_i$ values using the Cheng-Prusoff equation (Cheng et al., *Biochem. Pharmacol.* 22:3099–3108, 1973) and $K_d$ values of 1.0 nM ([$^3$H]R-PIA); 15.5 nM ([$^3$H]CGS 21680); 0.59 nM and 1.46 nM ([$^{125}$I]AB-MECA at human and $A_3$ receptors, respectively).

What is claimed is:

1. A method for reducing intraocular pressure in an individual with an ocular disorder, comprising the step of administering to said individual an effective intraocular pressure-reducing amount of a pharmaceutical composition comprising an $A_3$ subtype adenosine receptor antagonist.

2. The method of claim 1, wherein said $A_3$ subtype receptor antagonist is a dihydropyridine, pyridine, pyridinium salt or triazoloquinazoline.

3. The method of claim 1, wherein said As subtype receptor antagonist is selected from the group consisting of MRS-1097, MRS-1191, MRS-1220, MRS-1523 and MRS-1649.

4. The method of claim 1, wherein said pharmaceutical composition is administered topically, systemically or orally.

5. The method of claim 1, wherein said pharmaceutical composition is an ointment, gel or eye drops.

6. The method of claim 1, wherein said ocular disorder is glaucoma.

7. A method for reducing intraocular pressure in an individual with an ocular disorder, comprising the step of administering to said individual an effective intraocular pressure-reducing amount of a pharmaceutical composition comprising an antiestrogen.

8. The method of claim 7, wherein said antiestrogen is tamoxifen.

9. The method of claim 7, wherein said pharmaceutical composition is administered topically, systemically or orally.

10. The method of claim 7, wherein said pharmaceutical composition is ointment, gel or eye drops.

11. The method of claim 7, wherein said ocular disorder is glaucoma.

12. A method for reducing intraocular pressure in an individual with an ocular disorder, comprising the step of administering to said individual an effective intraocular pressure-reducing amount of a pharmaceutical composition comprising a calmodulin antagonist.

13. The method of claim 12, wherein said calmodulin antagonist is trifluoperazine.

14. The method of claim 12, wherein said pharmaceutical composition is administered topically, systemically or orally.

15. The method of claim 12, wherein said pharmaceutical composition is ointment, gel or eye drops.

16. The method of claim 12, wherein said ocular disorder is glaucoma.

17. A method for reducing intraocular pressure in an individual with an ocular disorder, comprising the step of administering to said individual an effective intraocular pressure-reducing amount of a pharmaceutical composition comprising a prodrug which is converted into a $A_3$ subtype adenosine receptor antagonist after said administering step.

* * * * *